United States Patent
Musin

(10) Patent No.: US 11,925,463 B2
(45) Date of Patent: Mar. 12, 2024

(54) METHOD AND MULTISENSORY DEVICE FOR NON-INVASIVE BLOOD GLUCOSE LEVEL MONITORING

(71) Applicant: "INTERCELLULAR SUBSTANCE TECHNOLOGIES LABORATORY R&D INTERCELL" LIMITED LIABILITY COMPANY ("R&D INTERCELL" LLC), Moscow (RU)

(72) Inventor: Ramil Faritovich Musin, Moscow (RU)

(73) Assignee: LCM Biosensor Technologies, Inc., East Setauket, NY (US)

( * ) Notice: Subject to any disclaimer, the term of this patent is extended or adjusted under 35 U.S.C. 154(b) by 706 days.

(21) Appl. No.: 16/303,371

(22) PCT Filed: Aug. 19, 2016

(86) PCT No.: PCT/RU2016/000561
§ 371 (c)(1),
(2) Date: Nov. 20, 2018

(87) PCT Pub. No.: WO2017/204677
PCT Pub. Date: Nov. 30, 2017

(65) Prior Publication Data
US 2020/0060584 A1    Feb. 27, 2020

(30) Foreign Application Priority Data
May 23, 2016 (RU) ............................ RU2016119799

(51) Int. Cl.
*A61B 5/145* (2006.01)
*A61B 5/00* (2006.01)
(Continued)

(52) U.S. Cl.
CPC ........ *A61B 5/14532* (2013.01); *A61B 5/0006* (2013.01); *A61B 5/015* (2013.01);
(Continued)

(58) Field of Classification Search
None
See application file for complete search history.

(56) References Cited

U.S. PATENT DOCUMENTS

| | | | |
|---|---|---|---|
| 6,918,874 B1* | 7/2005 | Hatch | A61B 5/00 600/309 |
| 2009/0209828 A1* | 8/2009 | Musin | A61B 5/0531 600/301 |
| 2012/0010477 A1* | 1/2012 | Amano | A61B 5/0075 600/301 |

FOREIGN PATENT DOCUMENTS

| | | | | |
|---|---|---|---|---|
| RU | 2 396 897 | | 8/2010 | |
| TW | 201315991 A | * | 4/2013 | ......... G01N 21/8483 |

OTHER PUBLICATIONS

English translation of TW 201315991, patents.google.com, 10 pages, printed on Mar. 8, 2023 (Year: 2023).*

(Continued)

*Primary Examiner* — Matthew Kremer
(74) *Attorney, Agent, or Firm* — Nixon & Vanderhye PC

(57) ABSTRACT

The present invention allows for non-invasive monitoring of the blood sugar levels in diabetic patients. At least one heat and waterproof applicator is applied to the skin surface by a dosage pressure. Temporal dynamics of physiological parameters of the local tissue region are measured under the applicator. Temporal dynamics of climatic parameters of the environment are measured simultaneously or before the beginning of measurement of physiological parameters in the monitoring mode. Further, enthalpy of tissue is calculated with account for the influence of climatic parameters. Magnitude of thermal effect of metabolism of the local area (Continued)

of living tissue is calculated on the basic thermodynamics equation, connecting enthalpy of tissue with variables of thermodynamic state. Relative changes in the level of glucose are calculated in blood, proportional to the value of the thermal metabolism of the local area of living tissue.

60 Claims, 18 Drawing Sheets

(51) Int. Cl.
    *A61B 5/01*     (2006.01)
    *A61B 5/0205*     (2006.01)
    *A61B 5/0533*     (2021.01)

(52) U.S. Cl.
    CPC ........ *A61B 5/02055* (2013.01); *A61B 5/0533* (2013.01); *A61B 5/4866* (2013.01); *A61B 5/6831* (2013.01); *A61B 2562/0271* (2013.01); *A61B 2562/029* (2013.01); *A61B 2562/063* (2013.01)

(56) References Cited

OTHER PUBLICATIONS

International Search Report for PCT/RU2016/000561, dated Feb. 9, 2017, 4 pages.
Hamlin Shannan K. et al., "Monitoring Tissue Perfusion and Oxygenation", 2014, p. 353, 354.
Musin R.F., et al., "Natural Water Diffusion Through the Stratum Corneum of the Human Body Epidermis and its Electrical Properties", Academy of Sciences of the USSR, the Institute of Radioengineering and Electronics, 1984, pp. 63-67.
Musin R.F., et al., "Membrane Mechanisms of Water Transport in Epidermis", Water and Ions in Biological Systems, 1988, pp. 167-172.
Smith John L., The Pursuit of Noninvasive Glucose: "Hunting the Deceitful Turkey", 2015, 192 pages.
Stroitelnaia fizika (Transl: Structure Physics), Vlagosoderzhanie, 2011, p. 14.03.

\* cited by examiner

METHOD AND MULTISENSORY DEVICE FOR NON-INVASIVE BLOOD GLUCOSE LEVEL MONITORING

This application is the U.S. national phase of International Application No. PCT/RU2016/000561 filed 19 Aug. 2016, which designated the U.S. and claims priority to RU Patent Application No. 2016119799 filed 23 May 2016, the entire contents of each of which are hereby incorporated by reference.

PRIOR ART

The present group of inventions relates to the medicine and medical technology and more particularly to methods and devices for monitoring blood glucose level by measuring a calorimetric method of a thermal effect and metabolic rate of a local area of living tissue. Using a group of inventions allow for non-invasive monitoring of the blood sugar levels of diabetic patients.

BACKGROUND OF THE INVENTION

Diabetes is one of the biggest global threats. According to the forecast of the International Diabetes Federation (IDF), the number of patients with diabetes by 2035 will increase to 592 million from 371 million in 2012. Global healthcare spending on diabetes treatment will rise to $936 billion by 2035, from $586 billion in 2012. According to the American Diabetic Association, about 6% of the US population, i.e. about 16 million persons suffer from diabetes mellitus. According to the reports of the same Association, diabetes is the sevenths main diseases resulting in lethal outcome in the USA. The number of deaths caused by diabetes is about 200,000 annually. Diabetes is a chronic disease the method of treating which are currently still at the development stage. Diabetes often leads to the development of complications such as blindness, renal disorders, nervous diseases and cardiovascular diseases. Diabetes is a leading disease resulting in blindness at the age of 20 to 74 years. Approximately from 12,000 to 24,000 persons annually loss vision because of diabetes. Diabetes is a leading cause of renal diseases in about 40% of new cases. About 40 to 60% of patients with diabetes are predisposed to different forms of nervous diseases, which can result in amputation of limbs. Patients with diabetes are approximately 2 to 4 folds more predisposed to cardiac diseases, in particular myocardial infarction.

Diabetes is a disease associated with insufficient production or inefficient use of insulin by cells of the body. In spite of the fact that causes of the disease are not completely understood, some factors such as genetic, environmental, viral have been identified.

There are two main forms of diabetes: type 1 and type 2.

Type 1 diabetes (known as insulin-dependent diabetes) is an autoimmune disease wherein insulin production completely terminates; and it most often develops in childhood and youth. Patients with type 1 diabetes need daily insulin injections. Type 2 diabetes is a metabolic disease caused by that the body cannot produce a sufficient amount of insulin or utilization thereof is inefficient. Patients with type 2 diabetes make up about 90 to 95% of a total amount of diabetics. Morbidity of type 2 diabetes in the USA approaches an epidemiologic threshold, mainly due to increase in the number of elderly Americans and a significant prevalence of a sedentary lifestyle leading to obesity.

Insulin promotes glucose penetration into a cell with subsequent cleavage thereof to obtain energy for all metabolic processes. In diabetics, glucose cannot penetrate into a cell, it accumulates in blood and cells experience energetic hunger.

Patients with type 1 diabetes inject to themselves insulin using a special syringe and a cartridge. Continuous subcutaneous injection of insulin through an implanted pump is also possible. Insulin is typically prepared from swine pancreas or it is synthesized chemically. Generally accepted medical methods of diabetes treatment prescribe patients taking insulin to carry out independent monitoring of blood sugar. Knowing blood sugar level, patients can adjust insulin dose in subsequent injection.

Adjustment is necessary, since because of different reasons, blood sugar level fluctuates during a day and from day to day. In spite of the importance of such monitoring, several conducted studies showed that a portion of patients who carry out such monitoring at least once daily, diminishes with age. This fall occurs mainly because the currently used method of monitoring is associated with invasive drawing a blood sample from a finger. Many patients consider drawing a blood sample from a finger to be a more painful procedure that insulin injection.

Creation of a non-invasive (bloodless) method for monitoring blood sugar in diabetic patients and on its basis a medical device capable of replacing industrial invasive glucometers is one of the topical unsolved problems of modern medicine and public health.

Methods and devices for measuring blood sugar level are known: [28, 19-27]. The proposed method and device for embodiment thereof allow determining blood sugar level by measurement using a microcalorimetric method of thermal effect (heat production) of a local tissue metabolism and correction of measurement errors due to the influence of external physical and climatic factors on the characteristics of living tissue. Existence of the functional relationship between sugar absorption rate by tissue cells and blood level thereof is indicated in the works [2,8,9].

Method of calorimetry is known to be widely used in biology for the study of thermal processes at the molecular and cellular levels [1, 29]. The microcalorimetry method is also successfully used to study thermal processes (heat release and absorption) in separate organs, in particular, in active muscles and nerve fibers.

Increased activity over the past decade in studies aimed at creating the microcalorimetry method for studying in physiological conditions in vivo, the thermal processes associated with the metabolism of a local area of human living tissue, is largely due to the work on the development of a noninvasive method for monitoring blood sugar (non-invasive glucometer) based on monitoring of heat production of a local area of human tissue. The scientific and technical problem of the development of a non-invasive glucometer, a device for bloodless blood sugar monitoring, is today one of the unresolved topical problems of modern medicine [28], which involves significant financial and intellectual resources.

The following methods: direct calorimetry and indirect calorimetry are the known methods of physiological calorimetry [16].

Method of direct calorimetry contemplates immediate determination of a total amount of irradiated heat using a calorimetric chamber for live objects.

Method of indirect calorimetry allows for determining an amount of irradiated heat in an indirect way based on accounting respiratory gas exchange dynamics using respiratory chambers and different systems. Two possible modifications of the indirect calorimetry method are distinguished: a method of a complete gas analysis (accounting absorbed $O_2$ and evolved $CO_2$) and a method of incomplete gas analysis (accounting absorbed $O_2$).

The close to the claimed object by chemical essence and achievable result is the method of the basal metabolic rate of the human body using a whole-body calorimeter (a direct calorimetry) described in [26]. (Determination of the basal metabolic rate of humans with a whole-body calorimeter. U.S. Pat. No. 4,386,604). By change in air temperature and a total water amount evaporating from the whole-body surface, a total whole-body heat irradiation is determined and the basal metabolic rate is calculated.

Another closest to the claimed object by chemical essence and achievable result is the method of measurement described in [25] (Whole body calorimeter, U.S. Pat. No. 5,040,541). The main drawbacks of the mentioned methods consist in that for embodiment thereof, cumbersome, stationary and expensive whole-body calorimetric chambers are required. Furthermore, the direct calorimetry method is characterized by a low accuracy.

The measurement method described in [27], wherein the measurement of heat effect and a rate of metabolism of a local tissue site determine the blood sugar content is the closest in technical essence to the claimed objects (Method and device for microcalorimetric measurement of the rate of local metabolism of tissue, water content of intercellular tissue, concentration of biochemical components of blood and pressure in the cardiovascular system. The patent of the Russian Federation for the invention Jo 2396897).

The metabolic rate is determined by measuring the total amount of water evaporating during an insensible perspiration from the surface of a local area of the skin and measuring the temperature and humidity of the ambient air.

Method of measurement makes it possible to realize a high accuracy in laboratory conditions with controlled parameters of a microclimate (temperature and humidity of the room) wherein the measurement is carried out, with constant values of climatic parameters of the environment (temperature and humidity of the environment, atmospheric pressure).

The main disadvantage of this method, limiting its practical application, is that the results of measurements depend on the physic-and-climatic factors of the environment; in each case, a new calibration of the measuring channel is required when the climatic factors change, with constant values of the microclimate parameters of the room where measurements are taken.

DISCLOSURE OF THE INVENTION

The purpose of this group of inventions is to develop a method and device for monitoring blood glucose levels using the microcalorimetry method for studying the thermal processes of metabolism of an arbitrary local area of human living tissue under controlled parameters of not only the microclimate of the room where measurements are taken, but also considering the climatic parameters of the external environment.

The technical result achieved by a group of inventions is to increase the accuracy of measuring the thermal effect of metabolism by considering measurement errors from the influence of external conditions, and also by considering measurement errors caused by physiological fluctuations of the measured parameters of the subject.

The technical result is achieved by the fact that the method for monitoring blood glucose level is characterized by the sequence of steps: value of the thermal metabolism of a local part of living tissue of the effect or intensity of metabolism of a local area of living tissue is calculated as follows: at least one heat and waterproof applicator is placed on the skin surface with a metered pressure, forming a closed system in the local area of tissue under the applicator; measure the temporal dynamics of the physiological parameters of the local tissue area under the applicator, namely, at least the amount of water in the intercellular space of tissue under the applicator; temperature of the deep layer of $T_{skin}$ tissue under the applicator; the temporal dynamics of the elastic pressure of tissue is measured under the applicator, while the temporal dynamics of the environmental climatic parameters are measured simultaneously or before the beginning of the measurement of the physiological parameters in the monitoring mode, namely, at least the room temperature $T_{room}$ and the relative humidity of the air $RH_{room}$ in the room where the measurement is performed, atmospheric pressure $P_{atm}$, measure the external heat flow through the enclosing structure between the room and the external environment or the temperature of the outside environment $T_{ext}$; further, the enthalpy of tissue is calculated taking into account the influence of climatic parameters, after which the value of the thermal effect of the $\Delta Q_{MET}$ metabolism of a local area of living tissue is calculated using the basic equation of thermodynamics that relates the enthalpy of tissue to the variables of the thermodynamic state and calculates the relative changes in blood glucose level proportional to the value of thermal metabolism a local area of living tissue.

In this case, the calibration procedure is performed to calculate the magnitude of heat effect of metabolism of a local area of living tissue and calculate blood glucose level proportional to the value of the thermal metabolism of a local area of living tissue, and the calibration parameters are determined in order to determine the constant coefficients.

Calibration parameters are determined individually for each patient by invasive measurements of blood glucose level. The calibration procedure involves measuring a continuous glucose level in the blood under conditions of the glucose tolerance test and determining the sensitivity of tissue to insulin.

In addition, the temporal dynamics of the temperature of the deep layer of tissue under the $T_{skin}$ applicator is determined by measuring the temporal dynamics of the skin surface temperature under the applicator and heat flux through the epidermis to the surface or by radio thermometry.

Temporal dynamics of the amount of water and its equilibrium content in the intercellular space of the lower layers of skin and subcutaneous tissues under the applicator is determined from the change in amount of water in the local area of tissue under the applicator.

In this case, change in the amount of water in the local area of tissue under the applicator is determined by measuring the electrical characteristics of the stratum corneum of the epidermis or the spectral characteristics of the stratum corneum of the epidermis or the thermophysical characteristics of the stratum corneum of the epidermis.

The local area of living tissue can be located on the hand or any other arbitrary area on the surface of the stratum corneum.

The intensity of heat formation in the process of metabolism of a local area of living tissue, the intensity of the metabolism of the local area of living tissue, including basal metabolism of the local area of living tissue, is calculated additionally.

Measure additional physiological and biochemical parameters that characterize the metabolism of the local area of living tissue.

When the physiological parameter is selected from the group including electrophysiological parameters, as well the electroencephalogram, electromyogram, skin-galvanic reaction, electrocardiogram. While the additional parameter is also selected from the group including the biochemical parameters of the blood, partial pressure of oxygen and/or carbon dioxide in the blood, heart rate and blood pressure. Biochemical parameter of blood is the acidity of blood, concentration of lactate in blood, glucocorticoid hormone.

In this case, concentration of the biochemical parameter in blood is calculated by measuring the dynamics of the biochemical parameter in the stratum corneum of the epidermis, including measuring the dynamics of the biochemical parameter in the sweat solution in the sweat gland under the applicator.

In addition, the measured values of the basal metabolism intensity of the local tissue site and additional physiological and biochemical parameters are compared with the interval of indices characterizing the normal physiological state of tissue, after which the deviation of the values of parameters obtained by measurements from the interval of indices characterizing the normal physiological state of tissue, and the magnitude of the deviation determines the nature of the deviation and assesses the degree of the pathological condition of tissue.

In addition, the dependence of the change in the amount of water in the intercellular space of tissues under the applicator on the effect of an external physical factor is measured, and the amount of water that ensures the swelling of the intercellular substance in its native state is measured.

The external physical factor is selected from the group consisting of external pressure, local decompression, heating, cooling, exposure to electric current and magnetic field.

Measure the additional parameters, determining the state of the intercellular substance selected from the group consisting of blood pressure, acidity, and elastic pressure are measured. Further, measured amount of water that provides swelling of the intercellular substance in its native state is compared, and additional parameters with an interval of parameters characterizing the normal physiological state of tissue determine the deviation of the values of the parameters obtained by measurements from the range of parameters characterizing the normal physiological state of tissue and by the magnitude of the deviation determine the nature of the deviation and evaluate the degree of the pathological state of the intercellular tissue.

In addition, method and mode of external physical influence on the living tissue site are determined depending on the state of the intercellular tissue, external physical action is carried out, and the effectiveness of the effect is controlled by re-measuring the parameter characterizing tissue site state.

For method introduction, blood glucose monitoring device is provided comprising a heat and a waterproof applicator having an upper and an inner surface and configured to be applied to the skin at a metered pressure, physiological sensors, climatic parameters sensors, a device for creating the calibration effect on tissue site under the applicator, an installation platform for fixing the sensors of climatic parameters, fixed over the applicator, sensors of the climatic parameters are located on the installation platform, and the sensors of the physiological parameters are located under the applicator, the signals from the above sensors being applied in series to the inputs of the amplifier and/or analog-digital converter unit installed on the upper surface of the applicator; the information processing unit; block of information display.

In addition, device for imposing a calibration action on the tissue site is a source of thermal power in the form of a resistor or Peltier element; source of electric current or voltage; source of electromagnetic radiation; device for creating a metered pressure on the surface of the applicator.

As sensors of physiological parameters, at least one sensor of the amount of water in the intercellular space of tissue in the local volume under the applicator is used; a skin surface temperature sensor under the applicator, a gauge of elastic pressure of tissue under the applicator.

At least an air temperature sensor, a relative air humidity sensor in the room, a heat flow sensor is used as sensors of climatic parameters through the enclosing structure between the room and the external environment.

In addition, sensor of the amount of water in the intercellular space of tissue in the local volume under the applicator is an electrometric sensor or a spectral sensor or a sensor based on measuring the thermophysical characteristics of the stratum corneum, or sensor is based on the measurement of tissue pressure or osmotic pressure of the intercellular substance, or a sensor based on the measurement of hydraulic pressure in the microcirculation system, or a sensor based on the measurement of the elastic pressure.

Electrometric sensor includes at least one basic and at least one measuring electrodes, a device for creating a metered pressure of the electrodes on the skin surface, a power supply and a measuring unit, and at least one of the electrodes is made as a dry waterproof electrode. The area of base electrode exceeds the area of the measuring electrode, while the area of one of the electrodes, measuring, satisfies the condition: $S$ $(mm^2)>2P$ $(mm)\times 0.4$ $(mm)$.

Working surface of the base electrode may be dry or provided with means for increasing the conductivity of the skin at the point of contact and more particularly to an electrically conductive paste.

Electrodes can be made in the form of combined disks with a total area determined by a large diameter. In addition, electrodes design is possible in the co-axial disks form.

Measuring unit is designed as a device for measuring the transverse electrical conductivity of the stratum corneum of the epidermis at a constant current or low frequencies, or a dielectric constant of the stratum corneum of the epidermis at low frequencies.

Heat and waterproof applicator can take the form of a measuring capsule, forming closed cavity with diffusion and thermal contact with the surface of the skin.

Closed cavity of the measuring capsule is hermetically sealed, and the working surface of said cavity contacting the skin is made in the form of a rigid membrane, permeable or semi-permeable to water and heat.

In addition, closed cavity of the measuring capsule, applied to the surface of the skin, does not have mechanical contact with the surface of the skin.

Cavity of the measuring capsule includes at least a material that absorbs water, which serves as a sensing element of a water amount sensor.

Water quantity sensor may be in the form of a water vapor pressure sensor or in the form of a water vapor concentration sensor based on spectroscopic methods or as a sensor for thermophysical characteristics of water vapor or as a heat capacity or thermal conductivity sensor for water vapor.

The dosage pressure of applicator is created by device build upon the basis of pneumatic, mechanical, piezoelectric, electromagnetic, vacuum or hydraulic principle.

Device further comprises sensors for measuring physiological parameters characterizing the metabolism of an organism selected from the group consisting of blood biochemical parameters sensors, oxygen partial pressure sensors and/or carbon dioxide gas sensors, acid-base state sensors.

By the sensor that characterizes the acid—base state of the body is a lactate sensor in the blood or a blood acidity sensor.

Blood cortisol sensor or heart rate sensor is an additional sensor of the physiological parameter.

Living tissue located directly under the in vivo controlled area of the skin surface (horny layer of the skin) is understood as a "local area of living tissue".

Metabolism of the controlled area of living tissue located directly under the applicator is understood as the metabolism of a local area of living tissue. Volume of controlled area is defined as mathematical product of the area of applicator applied to the skin surface and controlled length (depth), which corresponds to the length (determined as a distance from the surface of stratum corneum (SC) into the depth), where the local thermodynamic equilibrium of tissue is established after the applicator is applied to SC surface. Length L (from the surface of applicator to the depth) on which the local thermodynamic equilibrium of tissue is being established after imposition of applicator on SC surface is determined by diameter D of the applicator: L<D.

The controllable length L (depth) can be estimated—as it is approximately (by the order of magnitude) equal to the diameter of the applicator, and in the case of the laboratory scale sensor, with which the measurements were taken, is L<D=2-3 cm (20-30 mm). Wherein, the thickness of the epidermis, as is well known, is d=0.5 mm, and the thickness of the skin (epidermis+dermis) is 1-2 mm.

An important feature for practical application of this method is its effectiveness in measuring the intensity of metabolism deep in tissue at a controlled depth level L<D, where thermodynamic equilibrium is established after the applicator placement, despite the intensity of metabolism in the skin only.

BRIEF DESCRIPTION OF THE DRAWINGS

The accompanying drawings, which are incorporated in and constitute a part of this specification, illustrate embodiments of the inventive group and, together with a general disclosure of the group of the invention and the following detailed disclosure of the embodiments, serve to explain the principles of the present invention.

FIG. 14 (b). Multi-sensor device circuit for measurements in the "microcalorimeter" mode for measuring the thermal effect and metabolic rate of a local tissue part.

FIG. 14 (c). Estimated size and design of the appearance of the commercial version of the multi-touch device connected by wireless communication with a smartphone.

FIG. 15 (b) A photo of a prototype measuring head of a multi-sensor microcalorimeter for bloodless measurement of blood sugar. Applicator with microcalorimeter sensors is installed on hand surface and attached by straps provided with "Velcro"

Figure 1:
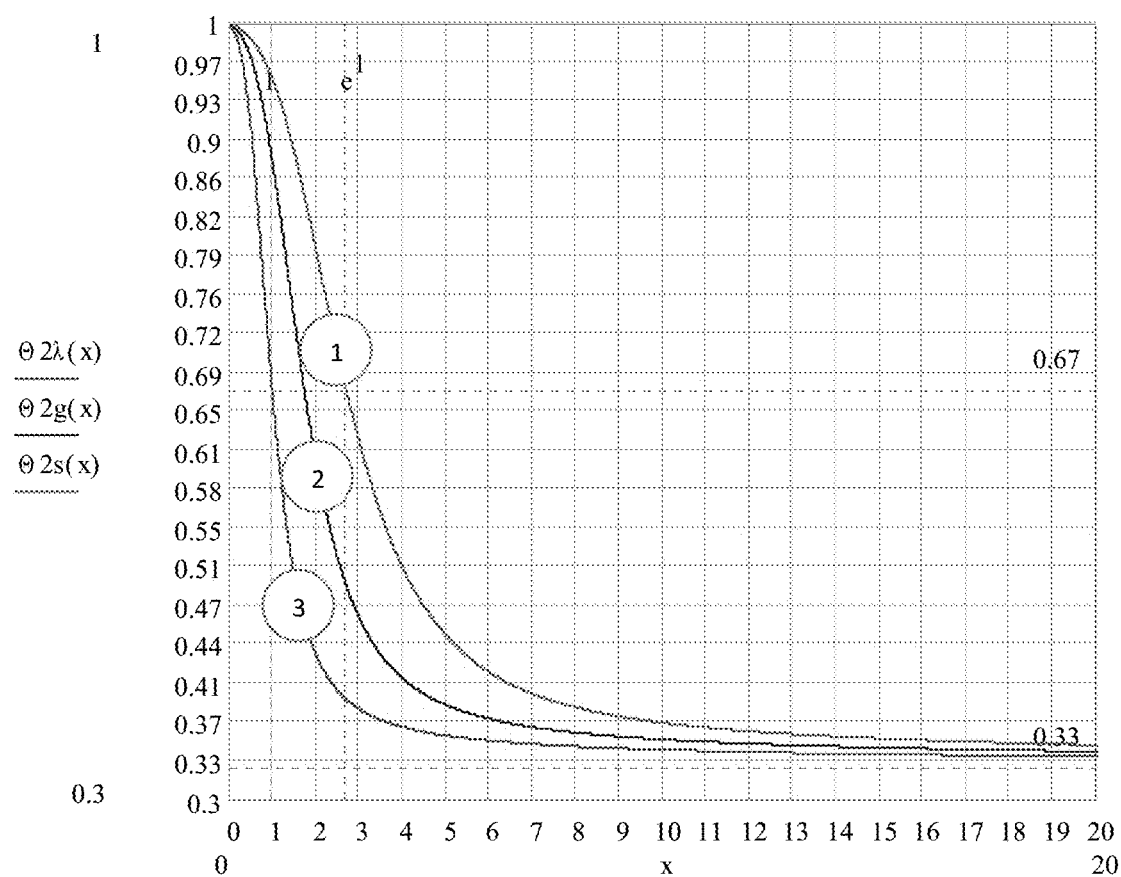
FIG. 1. The dependence graphs of the volume of intercellular substance on the concentration of glucose C in units of the dimensionless parameter $\alpha=C/C_0$ for different values of the external pressure $P_0$, where $C_0$ is the glucose concentration corresponding to the zero value of the osmotic pressure. Curves 1, 2 and 3 correspond to different values of the external pressure $P_{01}$, $P_{02}$, $P_{03}$, satisfying the condition: $P_{01}<P_{02}<P_{03}$.

X-axis represents the time in seconds, the Y-axis shows the meter reading in mmol/liter. Calibration pulses (at times 200, 500, 1000, 2000) are imposed on the time dynamics of the instrument readings.

The results of invasive measurements in mmol/liter are shown by circles: 52 (350); 53 (1200); 54 (2100).

Time in seconds (from the start of recording) is indicated in parentheses.

Values of air parameters inside the room (humidity H, temperature T, atmospheric pressure P) at the time of the first invasive measurement: HTP=25.6/21.5/1007.7

Climatic parameters: −1, 85%, 754, 3.0 m/s, at the beginning of the experiment; −1, 88%, 757, 2.0 m/s, at the end of the experiment.

FIG. 17 (b). Monitoring blood sugar of a healthy patient (58 years, male) during the day. Temporal dynamics of blood sugar after 1 hour after breakfast.

X-axis represents the time in seconds, the Y-axis shows the meter reading in mmol/liter. Calibration pulses (at times 200, 500, 1000, 2000) are imposed on the time dynamics of the instrument readings. The results of invasive measurements in mmol/liter are shown by circles: 7.7 (350); 7.0 (1200); 6.7 (2100). Time in seconds (from the start of recording) is indicated in parentheses.

Values of air parameters inside the room (humidity H, temperature T, atmospheric pressure P) at the time of the first invasive measurement:

HTP=23.8/22.2/1009.1

Climatic parameters:

−2.85%, 756; 6.0 m/s, at the beginning of the experiment

−3.84%, 756; 5.0 m/s, at the end of the experiment

FIG. 17 (c). Monitoring the blood sugar of a healthy patient (58 years, male) during the day. Temporal dynamics of blood sugar after 1 hour after lunch.

X-axis represents the time in seconds, the Y-axis shows the meter reading in mmol/liter.

Calibration pulses (at times 200, 500, 1000, 2000) are imposed on the time dynamics of the instrument readings.

The results of invasive measurements in mmol/liter are shown by circles: 7.7 (300); 8.9 (1200); 9.2 (2100). Time in seconds (from the start of recording) is indicated in parentheses.

Values of air parameters inside the room (humidity H, temperature T, atmospheric pressure P) at the time of the first invasive measurement:

HTP=23.8/22.3/1010.2

Climatic parameters:

−3/84/757/3.0 m/s, at the beginning of experiment

−3/78/757/3.0 m/s, at the end of experiment

FIG. 17 (d). Monitoring blood sugar of a healthy patient (58 years, male) during the day. Temporal dynamics of blood sugar after 2.5 hours after lunch.

X-axis represents the time in seconds, the Y-axis shows the meter reading in mmol/liter.

Calibration pulses (at times 200, 500, 1000, 2000) are imposed on the time dynamics of the instrument readings. The results of invasive measurements in mmol/liter are shown by circles: 6.2 (350); 6.4 (1200); 6.1 (2100). Time in seconds (from the start of recording) is indicated in parentheses.

Values of air parameters inside the room (humidity H, temperature T, atmospheric pressure P) at the time of the first invasive measurement:

CHTP=23.0/21.7/1011.6

Climatic parameters:

−3/78/757/4.0 m/s, at the beginning of experiment

−3/78/757/4.0 m/s, at the end of experiment

Figure 18A:
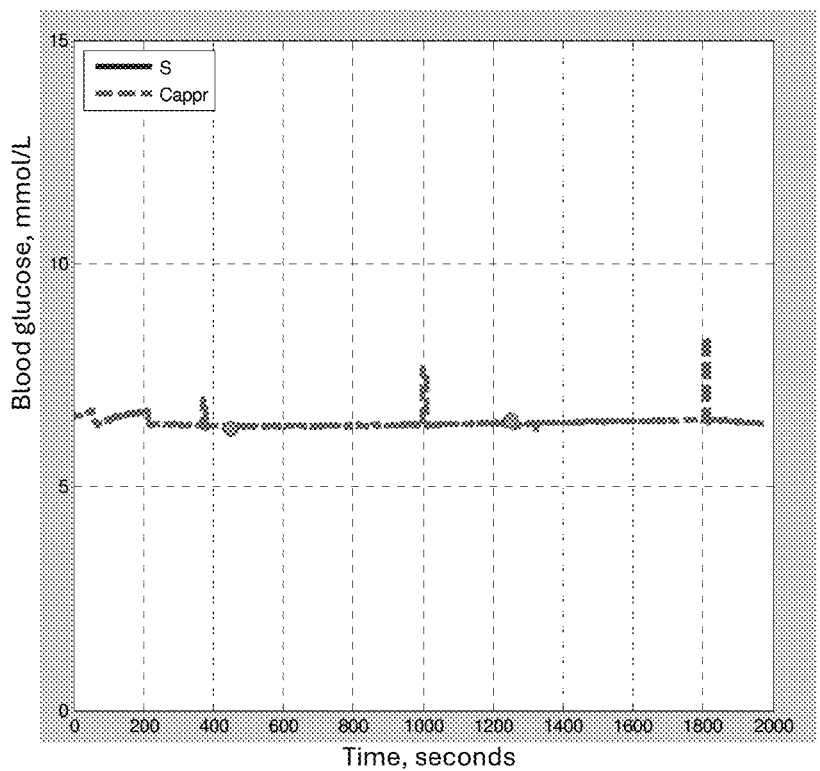

FIG. 18 (a). Temporal dynamics of the blood sugar of patient D with type 2 diabetes (68 years old, male) before lunch.

X-axis represents the time in seconds, the Y-axis shows the meter reading in mmol/liter. Calibration pulses (at times 400, 1000, 1800) were superimposed on the temporal dynamics of the device readings. The results of invasive measurements in mmol/liter are shown by circles: 6.3 (450); 6.5 (1250). Time in seconds (from the start of recording) is indicated in parentheses.

Values of air parameters inside the room (humidity H, temperature T, atmospheric pressure P) at the time of the first invasive measurement:

CHTP=30.3/26.3/720.0

FIG. 18 (b). Temporal dynamics of the blood sugar of patient D with type 2 diabetes (68 years old, male) 1 hour after lunch.

X-axis represents the time in seconds, the Y-axis shows the meter reading in mmol/liter. Calibration pulses (at times 200, 650, 1000) were superimposed on the temporal dynamics of the device readings. The results of invasive measurements in mmol/liter are shown by circles: 9.9 (250); 11.0 (1300). Time in seconds (from the start of recording) is indicated in parentheses.

Values of air parameters inside the room (humidity H, temperature T, atmospheric pressure P) at the time of the first invasive measurement:

CHTP=29.3/26.5/718.0

Figure 19:
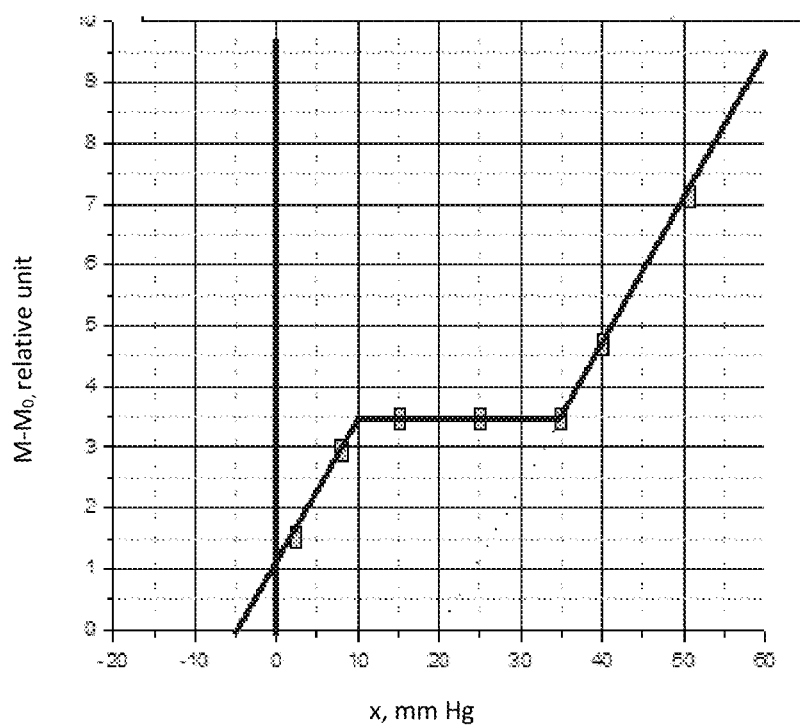

FIG. 19. Dependence of water content in intercellular tissue from external pressure on the surface of the stratum corneum of epidermis.

DETAILED DESCRIPTION OF THE INVENTION

Physical Basis of Heat Exchange of Living Tissue with the Environment.

Heat exchange is a spontaneous and irreversible process of heat transfer caused by temperature gradient. The following forms of heat exchange are distinguished: heat conductivity, convection, radiant heat exchange, heat exchange in phase conversions.

Heat transfer is heat exchange between the body surface and a medium (liquid, gas) contacting therewith.

Evaporative cooling is heat exchange between tissue and the environment caused by evaporation of water delivered to the epidermis from deep tissue layers. Heat flow density is determined by product of evaporation heat (steam generation heat) by water flow density evaporating from the surface.

Radiant heat exchange (radiation heat exchange, radiant transfer) is energy transfer from one body to another caused by the processes of emission, propagation, scattering and absorption of electromagnetic radiation. Each of these processes adhere to definite regularities.

Thus, under the conditions of equilibrium heat radiation emission and absorption adhere to the Plank's law of radiation, to the Stephan-Boltzmann law, to the Kirgoff law of radiation.

Essential difference of radiant heat exchange from the other forms of heat exchange (convection, heat conductivity) consists in that it can occur in the absence of a material medium separating surfaces of heat exchange, as electromagnetic radiation also propagates under vacuum.

The Plank's law of radiation establishes relation between radiation intensity, spectral distribution and temperature of the black body. In elevation of temperature, radiation energy rises. Radiation energy depends on wavelength. A total energy irradiated by the black body and measurable by a contact-less infrared thermometer is a total energy irradiated at all wavelengths. It is proportional to the Plank's equation integral by wavelengths and it is described in physics by the Stephan-Boltzmann's law.

The Stephan-Boltzmann's radiation law asserts a fourths degree proportionality of the absolute temperature T of the full volume density p of the equilibrium radiation: $\rho = \alpha \times T^4$, wherein "$\alpha$" is a constant, and a full emission capability W associated therewith:

$W = \beta \times T^4$, wherein "$\beta$" is the Stephan-Boltzmann's constant.

Radiant heat exchange between tissue surface and the environment is determined by the ratio:

$$\Delta W = \beta \times (T_{tissue}^4 - T_{air}^4) = W_0 \times (4\Delta T/T) = W_0 \times [4(T_{tissue} - T_{air})/T_{tissue}]$$

$$\Delta T \ll T_{tissue}$$

$T_{tissue}$ is skin surface temperature,
$T_{air}$ is ambient air temperature.

$$W_0 = \beta \times T_{tissue}^4.$$

$\Delta W$ is heat radiation from tissue surface to the environment.

Heat conductivity is one of the forms of heat transfer from more heated body parts to less heated parts. Heat conductivity results in leveling temperature. In heat conductivity, energy transfer is effected as a result of direct energy transfer from particles having a greater energy to particles with a lower energy. If relative change in T at an average free run distance length of particles is small, then the main heat conductivity law (the Fourier's law) is fulfilled: heat flow density q is proportional to temperature gradient T:

$$Q = -\lambda \text{ grad } T,$$

wherein $\lambda$ is heat conductivity coefficient of heat conductivity independent on grad T. The $\lambda$ coefficient depends on aggregate sate of a substance, molecular structure, temperature, pressure, composition thereof etc.

Convection is heat transfer in liquids and gases by substance flows. Convection results in leveling substance temperature. In stationary heat delivery to the substance, stationary convection flows occur therein. Intensity of convection depends on difference of temperatures between layers, heat conductivity and viscosity of medium.

Evaporative cooling is heat exchange between tissue and the environment caused by evaporation of water delivered to the epidermis surface from deep tissue layers through intercellular water transfer (by intercellular space). Heat flow density is determined by the product of steam heat (steam generation heat) by flow density of water evaporating from the surface.

In a comfortable temperature zone under normal conditions, water transport by sweating is known to be practically absent and the main contribution into evaporative cooling process is determined by water transport to the body surface. In physiology and medicine, this process is known as insensible (non-perceivable) perspiration [16].

Intercellular insensible perspiration is observed under so called "thermal comfortable conditions":

Ambient air temperature: 18-25° C.
Atmospheric pressure: 740-760 mm Hg.

Intensity of evaporative cooling process under thermal comfortable conditions is known to make up 400 to 700 mL/day or $10^{-8}$ to 10–7 g/second×cm². This corresponds to values of heat flows 1 to 10 mW/cm².

It is known that the physiological process of intercellular insensible perspiration has a high sensitivity towards the external heat fluxes [10-15]. Threshold of the process sensitivity to heat fluxes is 0.1 mW/cm², which is equivalent to sensitivity of the process to ambient temperature equal to 0.005 degrees.

An important consequence of high sensitivity of the physiologic process to an insensible perspiration towards external heat fluxes practical importance is dependence of the physical characteristics of the human skin epidermis on external physic-and-climatic factors, in particular, on the temperature and humidity of the environment and atmospheric pressure. In particular, the results for measurements of the physiological parameter of human skin epidermis—speed of imperceptible perspiration, with constant values of microclimate of the room, which is used for measurements, are dependent on the physic-and-climatic factors of the environment (temperature and humidity of the environment, atmospheric pressure). Low-frequency fluctuations in the temperature of the outside air within even one degree, with constant parameters of the microclimate of the room, which is used for measurements, lead to significant low-frequency fluctuations of the measured physiological parameter and, as a result, increase in measurement error.

Physical mechanisms of the process for transfer of water to the surface of body, thus maintaining heat balance of the local tissue site, are discussed below in the section "Physics of intercellular substance: transport of water through the epidermis".

Physiological and Biochemical Basis of Heat Production of Human Living Tissue

Oxidation of glucose which is one of the main energy suppliers in the body, occurs in accordance with the equation that may be presented in the following form:

$$Glucose + Oxygen => CO_2 + H_2O.$$

Change in a standard free energy in this reaction under physiologic conditions equals to:

$$\Delta G = -686,000 \text{ calories/mol.}$$

For comparison, a male weighing seventy kilograms who goes upstairs for an hour, expends about 1,000,000 cal. From this, it is clear that 686,000 calories, mentioned above are a vast amount of energy. Work done by man is of course much less than energy expended during this work as in irreversible process, not all change in free energy is converted into work. Real efficacy of this conversion (as will be described below) is not higher than 40%. Moreover, food is not "burned" immediately in oxygen releasing energy in the form of heat and this release occurs in steps and includes a number of rather complex chemical conversions each of which gives a small "portion" of energy.

Glucose is oxidized in the body forming carbon dioxide and water; this is one of the most universal processes underlying respiration and digestion processes.

In breaking each glucose molecule accompanied by lowering free energy, energy is released that is sufficient to form 93 ATP molecules by binding of phosphate groups to ADP molecules. Not all 93 molecules appear to be actually formed. At the same time, all the process includes a large number of enzymatic reactions. Nutrients (carbohydrates, fatty acids and amino acids) enter into a series of reactions forming the Krebs cycle (or the cycle of tricarboxylic acids) during which carbonic backbone of molecules is broken down with formation of $CO_2$ but ATP is not formed here. On the following reaction steps transfer of electrons using special enzymes (respiratory chain) occurs. At these steps, ATP is synthesized and the last step on the way of a long process of electron transfer consists in binding thereof to molecular oxygen. Generally, electron transfer process along the respiratory chain resulting in accumulation of energy in ATP molecules is called oxidative phosphorylation. As a result of this process, 38 molecules of ATP as calculated per every consumed glucose molecule are formed. Efficacy of such transformation equals to 38/93=40%.

A value of heat production or heat power of the body can be quantitatively assessed originating from the following simple considerations. An energetic value of human nutrition is about 2,400 kilocalories/daily. In a first approximation, 2,400 kilocalories=$10^4$ J, 1 day (24 hours)=86,400 seconds=$10^5$ seconds.

Then energy consumed by human body per one second will be $10^4/10^5$=0.1 kJ×s$^{-1}$ or 100 J×s$^{-1}$, or 100 W; thus, heat power of a man is approximately equal to power of an electric bulb having power 100 W.

In muscular contraction, ATP which is energy donor for muscular contraction process, during reaction with myosin, allows for obtaining at most 50 J×g$^{-1}$ energy. This means that an ideal muscular system (i.e. with efficiency equal to 100%) for lifting a load weighing 1 kg to a 5 m height, would require expenditure of $2 \times 10^{-3}$ mole ATP. Actually, muscular efficiency is about 30-40% and the rest portion is released in the form of heat.

Under normal conditions of the body's vital activity, glucose is a main energetic substrate. Normal human blood plasma glucose concentration depending upon nutrition conditions is maintained within the limits of 50 to 120 mg %. Postprandial glucose concentration in the portal vein system during absorption phase can achieve more than 270 m %. Elevation of blood glucose level always causes increase in insulin secretion.

In resting human body, fasting glucose metabolism rate averages 140 mg/hour per 1 kg body mass, 50% glucose being consumed by the brain, 20% by muscles, 20% by red blood cells and kidneys, and only 10% glucose are left for the rest tissues.

Glucose utilization rate (metabolism rate) in healthy man is a linear function of blood plasma glucose concentration. A mathematical relationship between glucose utilization and blood concentration thereof in normal humans is expressed by the equation:

$$R_u = 0.02554C + 0.0785,$$

And in patients with non-ketotic diabetes:

$$R_u = 0.004448C + 2.006,$$

wherein $R_u$ is glucose utilization rate in mg/min per 1 kg body mass, and C is blood plasma glucose concentration in mg % [Reichard G. A. et al., 1963; Forbath N., Hetenui C., 1966; Moorhouse J. A., 1973; Moorhouse J. A., et al., 1978; Hall S. E., et., 1979, [2,8,9]. The term glucose "utilization" in physiological sense means the rate of glucose transport from blood into a general fund of tissue glucose and exit from it during metabolism. From biochemical point of view, glucose utilization rate is determined by transport through cytoplasmic membrane and by intracellular oxidative phosphorylation of glucose. The terms "turnover rate", "assimilation" and "consumption" of glucose which are widely spread in the literature are synonyms of the notion glucose "utilization" and they are in any respect equivalent.

Under physiologic conditions, practically in all tissues glucose transport from intercellular medium into a cell is a first limiting reaction in glucose utilization by cells as in the absence of insulin, flow of transportable glucose is always less than glucose phosphorylation rate. Equilibrium between glucose transport and phosphorylation rates is achieved only at high glucose concentrations (400 to 500 mg %). In further increase in glucose concentration, phosphorylation becomes a limiting reaction [2]. In other words, glucose transport rate from intercellular medium through cytoplasmic membrane into intracellular medium is a process limiting glucose utilization rate by a live tissue.

Originating from the above consideration, it appears logical and completely reasoned to draw a conclusion that heat production as well as glucose utilization rate is a linear function of blood glucose concentration and measurement of local heat production value allows for determining blood glucose level.

Phenomenological Equation of Heat Balance of Human Living Tissue

In the dynamically balanced (stationary) natural state of living tissue, heat balance between the produced heat (heat production) $W_{MET}$, and heat released to the environment, ensuring a constant temperature of tissue, is generally described by a phenomenological equation:

$$\Delta H / \Delta t = W_{MET} - (J + W_R + W_C + W_T) = W_{MET} - J - W_{SKIN}, \qquad (5)$$

where
$W_{MET}$—heat production;
$W_{SKIN} = W_R + W_C + W_T$;
$W_R$—heat emission by radiation (radiant heat transfer),
$W_C$—heat transfer by convection, $W_T$—heat transfer from the epidermis surface by thermal conductivity, J—convective heat transfer by evaporation in the process of imperceptible perspiration (steam cooling), H—enthalpy (heat content) of the surface layer of living tissue.

In equation (5), which has an experimental justification, it is taken into account that heat flux corresponding to the difference between the $W_{MET}$ heat production and heat transfer $J+W_{SKIN}$ is equal to the rate of change of heat content $\Delta H/\Delta t$ of the surface layer of living tissue corresponding to heat flux that is absorbed by the epidermis during heat transfer.

In the course of our research, we have experimentally studied the dependence of the process of thermoregulation of a local tissue site on physiological and physic-and-climatic parameters (state variables) and functional relationship (equation of state) was established, connecting parameters (state variables) that uniquely determine the thermodynamic behavior of living tissue.

It has been established experimentally [10-15] that the intercellular substance of living tissue is a kind of natural isothermal microcalorimeter of thermal power that provides heat balance of the local tissue site with the environment:

$$\Delta J = \Delta W \text{ at } C = C_0 = \text{const.}$$

The change (increase) in the power of heat flux of evaporative cooling $\Delta J$ (at a constant sugar level $C=C_0=$const) is equal to the change (increase) in heat flux $\Delta W$ caused by change in climatic factors of the environment.

Figure 12:
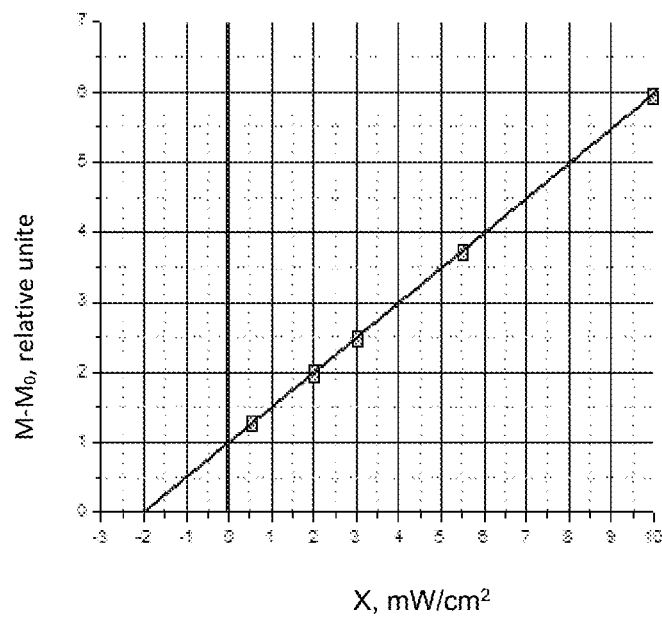
FIG. 12. The experimental dependence of the amount of water in epidermis (in relative units) on the value of external heat flux (mW/cm$^2$). The dashed line shows the linear approximation of this dependence in the region of physiological factor fluctuations that determine the threshold capacity.

The experimental dependence of evaporative cooling power J (relative units) on density of the external heat flux W (mW/cm$^2$), investigated in [10-15], using the highly sensitive non-invasive method for measuring micro streams of water in the process of insensible perspiration through the epidermis [10-15] is shown in FIG. 12.

Linear approximation of the experimental dependence in the region of intrinsic physiological fluctuations in the process of imperceptible perspiration makes it possible to determine the threshold sensitivity of the skin epidermis to heat fluxes, which turned out to be 0.1 mW/cm$^2$. The obtained threshold value of thermal sensitivity is equivalent to the value of evaporative cooling power about a picolitres per second from the square centimeter of the body surface ($10^{-12}$ liters/s×cm$^2$).

Fundamentally new opportunities and approaches that have made it possible to create a microcalorimetric method for measuring the thermal effect of living tissue metabolism by high-precision measurement of micro-flows of tissue fluid in the intercellular space of epidermis (method for monitoring the micro-hydrodynamics of intercellular substance), were opened due to fundamental research in the field of physics of intercellular substance and living tissue, carried out by the authors of the project, main provisions of which are described below.

It is quite obvious that the property of thermoregulation of a local section of living tissue, described above, is consistent with heat balance equation (5), which has an experimental justification, provided that the enthalpy of living tissue H(t) is a physiological thermodynamic parameter, which value remains constant with changes in external climatic thermal parameters and internal physiological parameters that determine the intensity of metabolism of the local area of living tissue.

Physics of Intercellular Substance: Physical Model.

Theoretical study was carried out in order to explain the features of thermodynamic behavior of living tissue observed in the experiment, in particular, high sensitivity of living tissue to external heat fluxes (due to variations in climatic factors of the environment) and the unique property of physical thermoregulation of the local area of living tissue.

Theoretical study was carried out within the framework of a physical model system that considers an intercellular substance (the main structural components of which are the polymeric molecular chain of hyaluronic acid, sea water and glucose) as a statistical system consisting of a large number of interacting particles. Physical model of intercellular substance, which allows one to describe thermodynamic behavior and calculate its statistical properties, can be formulated as follows:

an open system consisting of a polymeric molecular chain of hyaluronic acid localized in the sea water tank containing glucose bound to a thermostat and in thermal and diffusional contact with the atmosphere.

The main and only assumption of the model is the assumption that the intercellular substance of living tissue at normal physiological temperature and normal atmospheric pressure is near the stability boundary in the region of phase transition. Such an assumption, as it occurs, leads to predictions that are in good agreement with the experiment.

There were determined the thermodynamic behavior of the system near the stability boundary, determined by the critical order-disorder transition temperature, which in energy units is equal in order of magnitude to the characteristic energy of interaction between the particles of the system. In case under consideration, from the condition of phase transition it follows (proximity of the stability boundary) that the energy of interaction of not neighboring links of the molecular chain, which, despite the distance along the chain, are far from each other, but accidentally met in space as a result of chain bends, is equal to the quantum of thermal energy $k_B T$.

The assumption about the model that the intercellular substance of living tissue at normal physiological temperature and normal atmospheric pressure is in the region of phase transition near the stability boundary is equivalent, therefore, to the assumption that the physiological temperature corresponds to the critical temperature, which in energy units is equal in order of magnitude to the characteristic interaction energy between the links of polymer chain.

Volumetric interactions of non-neighboring chain links (spaced in the link far apart from each other), which result in bulk effects of the macromolecule, are described as conjugate biochemical reactions that occur with zero thermal effect and lead to the formation of crosslinks with binding energy $k_{BT}$ and volume change; in this case, the kinetics of chemical reaction is described as adsorption (binding to the thermal binding energy) of individual sodium ions and glucose molecules on "pseudo-nodes" having 4 binding sites.

Within the framework of statistical model under study, it was possible to obtain an exact solution for the energy of intermolecular interaction and to accurately calculate the statistical properties of the system, in particular, to determine the thermodynamic functions of tissue pressure (osmotic pressure of intercellular substance) and strain of elastic deformation of intercellular tissue (elastic pressure) depending on the macroscopic variables of the intercellular substance state: concentration of glucose in blood, external pressure and temperature.

Some results of our theoretical study are presented in the graphs of thermodynamic functions. In particular, here are presented the graphs of functions (without considering the analytical expression of the functions themselves) describing tissue (osmotic) pressure, volume, stress of elastic deformation and heat content of the intercellular substance depending on the condition variables—glucose concentration (C), temperature (T) and external pressure (P).

FIG. 1. shows the dependency graphs of the intercellular substance volume on the concentration of sugar C in units of dimensionless parameter $x=C/C_0$, for fixed values of the other two state variables (pressure $P=P_0$ and ambient temperature $T=T_0$) for different values of the external pressure P0, where $C_0$ is the glucose concentration corresponding to zero osmotic pressure. Curves 1, 2 and 3 correspond to different values of the external pressure $P_{01}$, $P_{02}$, $P_{03}$, satisfying the condition: $P_{01}<P_{02}<P_{03}$. As follows from the graph, with an increase in glucose concentration, the volume of the system decreases, due to the formation of cross-links between non-adjacent links of the chain, which are far apart along the chain.

Figure 2:
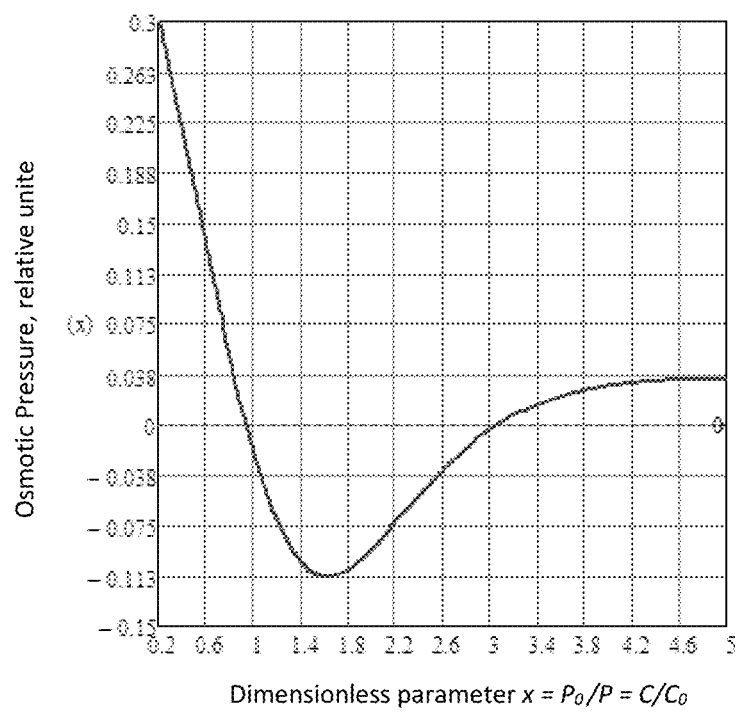
FIG. 2. A dependence graph of the osmotic pressure of the intercellular substance (tissue pressure) as a function of the dimensionless parameter $\alpha=C/C_0=P_0/P$, where C is the concentration of glucose in blood; $C_0$ is the glucose concentration corresponding to zero osmotic pressure; P—hydrostatic pressure in the capillary; $P_0$ is the pressure in the capillary corresponding to zero osmotic pressure.

FIG. 2. shows a plot of the osmotic pressure in the intercellular substance (tissue pressure) versus the dimensionless parameter $x=C/C_0=P_0/P$ for fixed values of the two other state variables (external pressure $P=P_0$ and ambient temperature $T=T_0$), where C—concentration of glucose in blood; $C_0$ is the glucose concentration corresponding to zero osmotic pressure; P—hydrostatic pressure in the capillary; $P_0$—is pressure in the capillary corresponding to zero osmotic pressure.

As it follows from the graph, with increasing glucose concentration, osmotic pressure of the substance decreases, which at the point $x=1$ ($C=C_0$) becomes zero and takes negative values in the concentration range [1, e].

Figure 3:
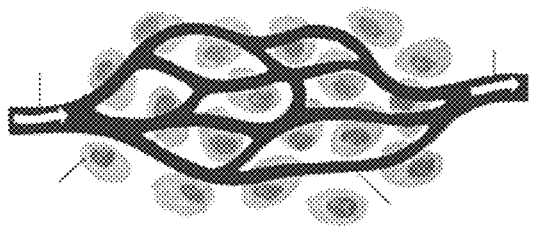
FIG. 3. Structural element of the local area of living tissue: main elements that form tissue structure are cells, intercellular substance and a system of blood capillaries and micro vessels that form a microcirculation system in the local tissue area.

FIG. 3. schematically shows an image of a characteristic structural element of the local area of living tissue, where cells are forms the main structural elements, intercellular substance and the system of blood capillaries and micro vessels forming a microcirculation system of the local area of living tissue. Physics of intercellular substance, based on the assumption that physiological temperature of tissue corresponds to the critical temperature, which in energy units is equal to the characteristic energy of interaction between the links of the polymer chain, allows describing the phenomena of energy and substance transfer (microcirculation, thermoregulation, cellular metabolism) forming a single physiological process self-organization (self-regulation) of the local volume of human flesh.

Figure 4:
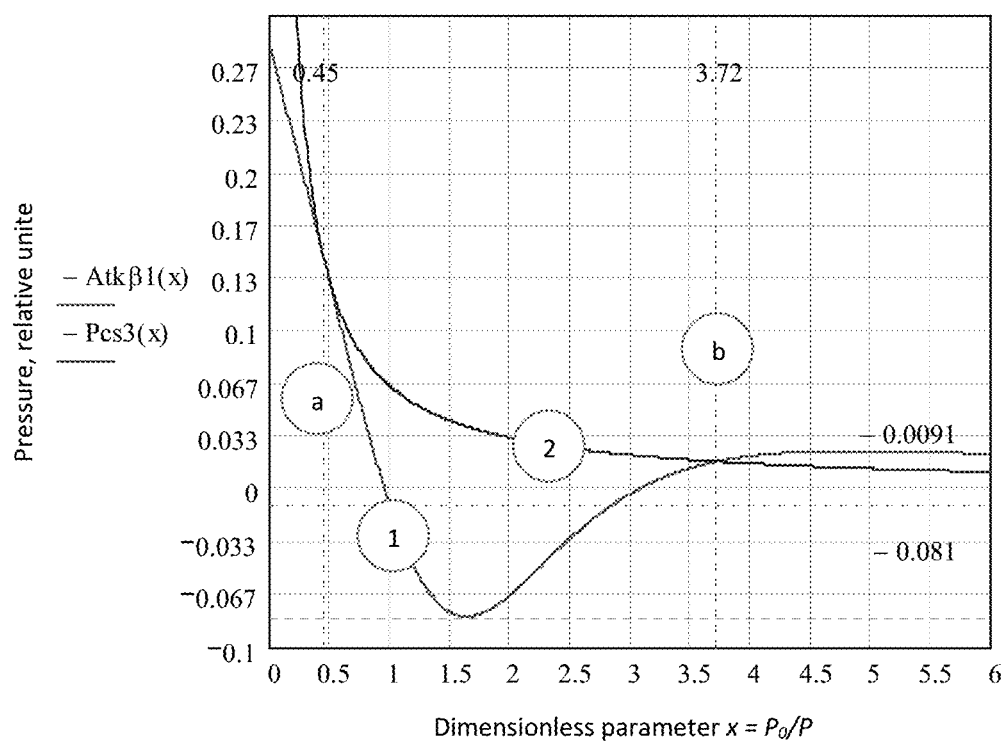
FIG. 4. The dependence graphs of the osmotic pressure of the intercellular substance (tissue pressure, curve 1) and the hydraulic pressure P in the capillary (curve 2) on the dimensionless parameter $\alpha=P_0/P$—the reciprocal of the reduced hydraulic pressure in the capillary, where $P_0$ is the capillary pressure at the zero flow point a capillary corresponding to zero osmotic pressure.
Figure 5:
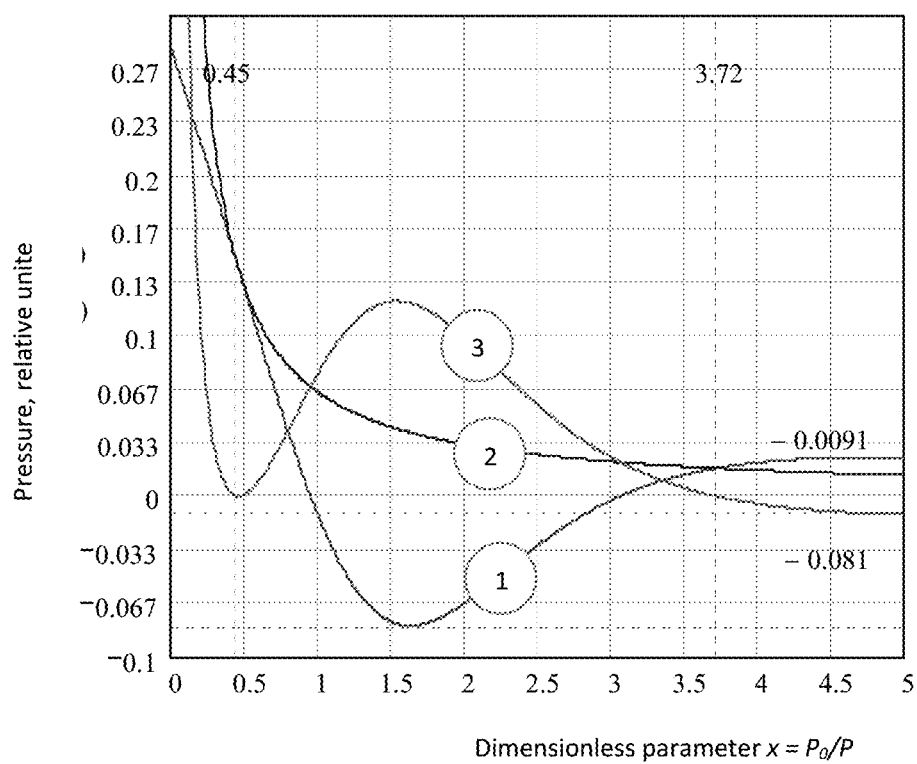
FIG. 5. A dependence graph of stress of elastic deformation of intercellular substance (elastic pressure, curve 3) and hydraulic pressure in the capillary in units of the dimensionless parameter $\alpha=P_0/P$ is the reciprocal of the reduced hydraulic pressure in the capillary, where $P_0$ is the capillary pressure at the point of the zero flow.
Figure 6:
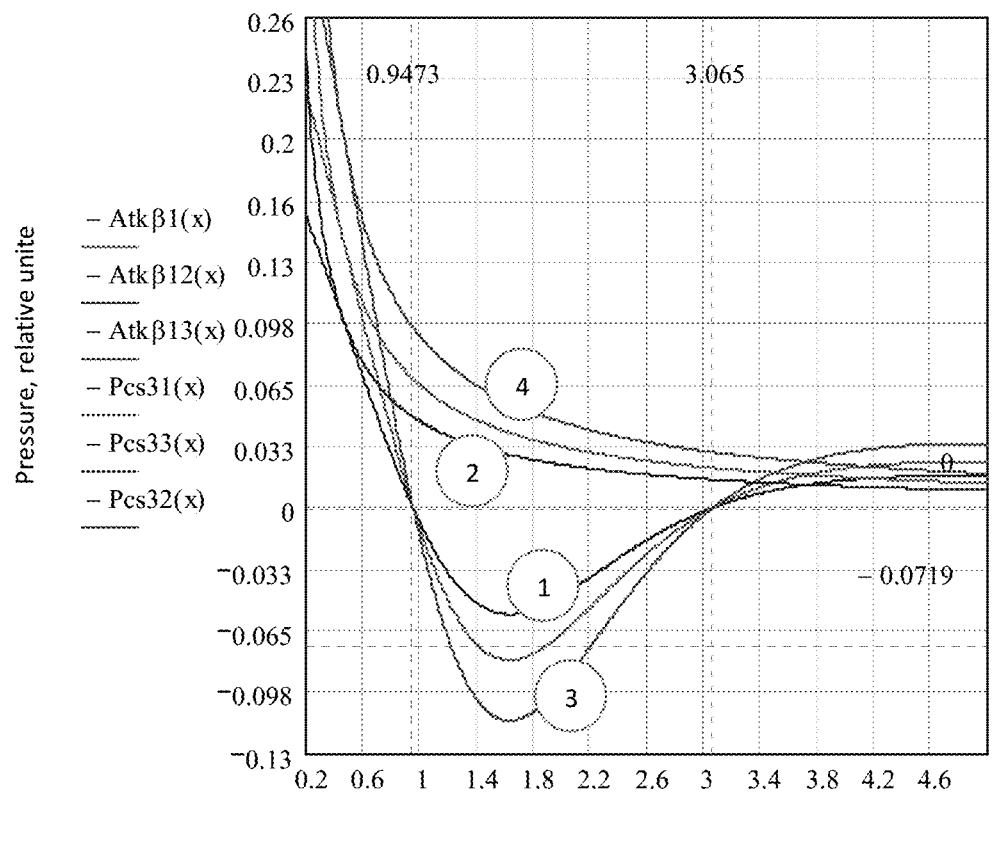
FIG. 6. The dependence graphs of the osmotic pressure of the intercellular substance and the hydraulic pressure in the capillary as a function of the reciprocal of the reduced pressure in the capillary (the dimensionless parameter $\alpha=P_0/P$) for different values of the glucose concentration in blood. Curves 1 and 2, and curves 3 and 4 correspond to different values of the glucose concentration, respectively, $C_1$ and $C_2$, which satisfies the condition $C_1>C_2$.

FIGS. 4-6. below show graphs of the main thermodynamic functions describing transport phenomena in the local volume of living tissue and more particularly to the phenomenon of microcirculation of blood and more particularly to tissue fluid flows between the capillary and the intercellular space.

FIG. 4. below show the graphs of the intercellular substance osmotic pressure (tissue pressure, curve 1) and hydraulic pressure P in the capillary (curve 2) from the dimensionless parameter $x=P_0/P$—the reciprocal value of the reduced hydraulic pressure in capillary, where P0 is the capillary pressure at the point of zero capillary flow corresponding to zero osmotic pressure value.

The graphs have two common points: "a" (the arterial end of the capillary) is the point of contact of two graphs; "v" (the venous end of the capillary) is the point of two graphs intersection. Pressure inside the capillary at points "a" and "v" is equal to tissue pressure (osmotic pressure of the intercellular substance). In the interval of external pressures [a, 1] (area of high pressures), tissue pressure has positive values. Swelling of the main substance and stretching of the intercellular tissue (volume increase) occurs in this pressure range. In the interval of external pressures [1, 3], tissue pressure has negative values. Dehydration and intercellular tissue compression (volume reduction) occurs within this range of external pressures.

In the interval of external pressures [3, v] (low pressure region), tissue pressure has positive values. Swelling of the main substance and stretching of the intercellular tissue occurs in this pressure range. Degree of swelling of intercellular substance is determined by the amount of water in the intercellular substance volume. Specific points wherein the internal pressure in capillary is equal to tissue pressure of the intercellular tissue, determine the range of pressures inside the capillary, between its inlet and outlet. Point "v" determines the value of the minimum (output) hydraulic pressure inside the capillary, and point "a" the value of maximum pressure or pressure at the capillary entrance. Such type of dependence of the intercellular substance tissue pressure on the magnitude of the external pressure (for a fixed glucose concentration) leads to the appearance of an uneven distribution of the strain of elastic deformation (elastic pressure) along the blood vessels and capillaries, in particular.

FIG. 5. Demonstrates the dependence of stress of elastic deformation of the intercellular substance (elastic pressure, curve 3) on hydraulic pressure in the capillary in units of the dimensionless parameter $x=P_0/P$ is the reciprocal of reduced hydraulic pressure in the capillary, where $P_0$—is capillary pressure at the point of zero capillary flow.

Dependence of osmotic and elastic pressures of intercellular tissue on the value of hydraulic pressure in the capillary has the following characteristic features:

1. Difference between capillary and tissue pressures is balanced by the elastic pressure (by the strain of elastic deformation of intercellular tissue). For this purpose, capillary is not a tube, which elastic shell balances the capillary pressure inside, but a tunnel in the intercellular tissue, which elastic deformation and tissue pressure balance the capillary pressure from inside.

2. The nonlinear nature of dependence of the elastic deformation stress in the vicinity of the point "a" (capillary entry) leads to narrowing in the "bottle neck" type. The lumen of the capillary increases toward its venous end, despite the decrease in hydraulic pressure inside it. Such constriction has the main hydraulic resistance to flow through the capillary, determines its throughput and leads to a significant drop in hydraulic pressure at the initial portion of capillary.

3. The area of high (arterial) pressures is located to the left of point "a", and the area of low (venous) pressures is located to the right of the point "v".

4. Mechanical equilibrium of the capillary membrane (tunnel wall) is determined by the steady state between hydraulic pressure in the capillary and osmotic, elastic pressure of the intercellular tissue.

The condition of mechanical equilibrium at point "a" has the form:

Tissue (osmotic) pressure=hydraulic pressure inside the capillary. Stress of elastic deformation (elastic pressure) =zero.

Change in sugar level of blood leads to violation of mechanical equilibrium and appearance of strain of elastic deformation, unbalanced inside the capillary hydraulic pressure.

An increase in the blood sugar level leads to a reduction in the area of the capillary (lumen) of the capillary at point "a" at the input, caused by the compression of the surrounding capillary of tissue, as a consequence of a decrease in osmotic pressure of the intercellular substance.

Reducing the capillary cross-section at the entrance leads to an increase in hydraulic resistance to the flow and, as a result, it increases pressure at the entrance to the capillary (at point "a"). Increase in pressure in the capillary caused by increase in the sugar concentration leads to transfer of intercellular substance to a state with a new value of osmotic pressure corresponding to the new values of equilibrium constants $C_0$ and $P_0$ that coincide with the values of concentration and pressure at the point x=1 (C=$C_0$, P=$P_0$). Mechanical equilibrium is established after equalizing tissue and capillary pressure at the capillary entrance. This process leads to a change in the equilibrium distributions of the hydraulic pressure in the capillary and elastic pressure of the intercellular tissue in the direction toward the venous end of the capillary. Achievements of mechanical balance at point "a" leads to the establishment of equilibrium along the entire length of the capillary.

FIG. 6. shows the dependency graphs of the equilibrium distribution of osmotic pressure of the intercellular substance and hydraulic pressure in the capillary as a function of the reciprocal value of the educed pressure in the capillary (dimensionless parameter x=$P_0$/P) for different values of blood glucose concentration. Curves 1 and 2, and curves 3 and 4 correspond to different values of the glucose concentration, respectively, $C_1$ and $C_2$, which satisfies the condition $C_1 > C_2$.

Peculiarity of the obtained dependences is that when the blood sugar level is raised, the position of points at which tension of the intercellular tissue elastic deformation is zero (points "a" and "v") remains unchanged on the abscissa axis. This means that proportional increase in pressure occurs inside the capillary at all points, from the entrance to the capillary outlet. The inlet pressure (maximum system pressure) and the outlet pressure (minimum pressure in the system), as well as the pressure at any other point inside the capillary, are linear functions of the blood sugar level, and the ratio $P_{max}/P_{min} = P_d/P_6 = 3.72/0.46 = 8.087$ thus remains constant.

Physics of Intercellular Substance:
Thermoregulation of Living Tissue

As it was shown above, thermoregulation property of a local area of living tissue is consistent with heat balance equation (5), provided that heat content of living tissue H(t) is a physiological parameter, which magnitude remains constant with changes in external climatic parameters of the environment and internal physiological parameters, determining the intensity of metabolism of a local area of living tissue.

The basic assumption of the studied model is that the intercellular substance of living tissue in its native state is in the region of the thermodynamic phase transition near the stability boundary, which is realized at a temperature equal to the energy units of interaction energy between the links of polymer chain and corresponds (at normal atmospheric pressure) the normal physiological temperature of living tissue.

Volumetric interactions of non-neighboring chain links (spaced far apart from each other), which result in bulk effects of the macromolecule, are described as conjugate biochemical reactions that occur with zero thermal effect and lead to the formation of "sugar" crosslinks with binding energy $k_{BT}$ and change volume; in this case, the kinetics of chemical reaction is described as adsorption (binding to the thermal binding energy) of individual sodium ions and glucose molecules on "pseudo-nodes" having 4 binding sites.

One of the important consequences arising from the basic assumption of the statistical model described above is the exact solution for the energy of the intermolecular interaction and enthalpy of the intercellular substance.

Figure 7A:
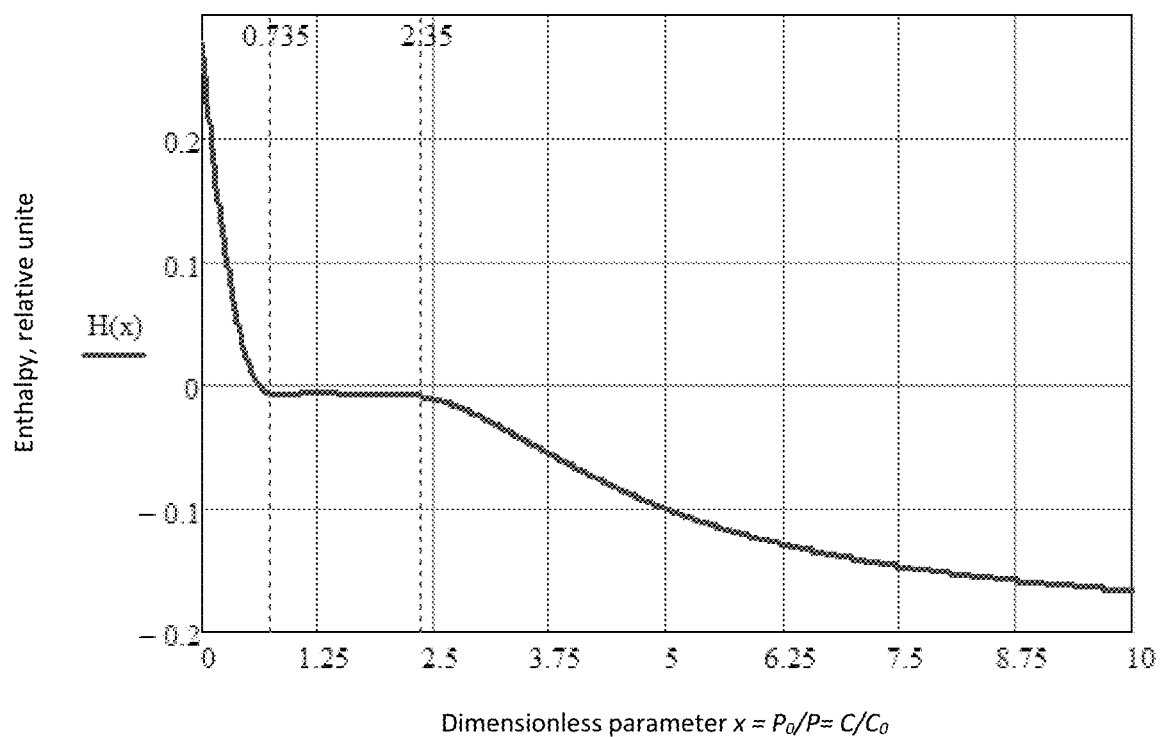
FIG. 7a. A dependence graph of thermal function (heat content, enthalpy) of the intercellular substance unit volume and glucose concentration and external pressure in units of the dimensionless parameter $\alpha=C/C_0=P_0/P$ at constant temperature (isotherm).

FIG. 7a. is a plot of heat function (heat content, enthalpy) of a single volume of intercellular substance from glucose concentration and external pressure in units of the dimensionless parameter x=C/$C_0$=$P_0$/P at constant temperature (isotherm). It should be noted that the processes of transfer of matter and energy in living tissue occur due to the redistribution of water between the circulatory system of microcapillaries and the intercellular space without changing the volume of living tissue, whose characteristic is the thermal function of a unit volume.

Characteristic feature of dependence of heat function on the state variables is the presence of a horizontal section in the range [0.735-2.15] of the dimensionless parameter x corresponding to the constant value of the enthalpy in this interval.

It should be noted that the curve of the dependence of heat content of a unit volume of living tissue at a constant temperature, shown in FIG. 7a, resembles a pressure-volume isotherm for a real gas with a predetermined amount of matter in the volume below the piston at a temperature wherein the liquid and gaseous forms can coexist at T<$T_{crit}$. As it is known, in the two-phase region of the liquid+gas system in the volume below the piston, the pressure is constant, but the volume can vary. At a certain predetermined temperature, there is only one value of pressure wherein liquid and its vapor are in equilibrium. If the piston is moved downward at this pressure, some gas condenses, but the pressure remains constant until all the gas is condensed.

Figure 7B:
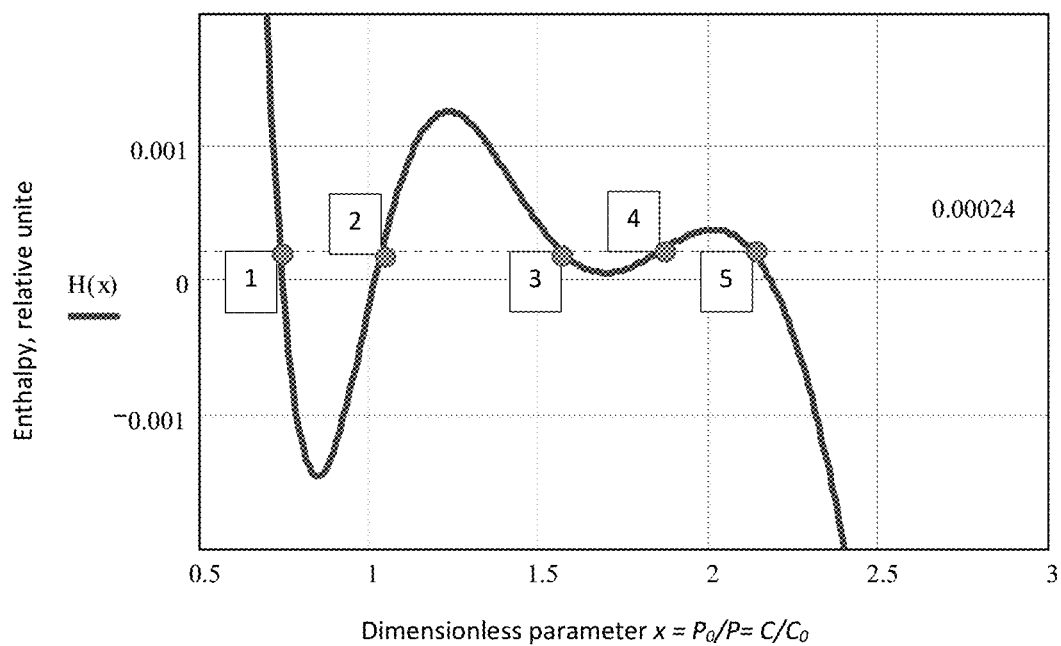
FIG. 7b. A graph for the horizontal section of three-phase region of the intercellular substance isotherm is presented with a higher resolution.

The horizontal portion of the total heat content curve of a living tissue shown in FIG. 7a corresponds to the three-phase gas+liquid+solid phase of the intercellular substance. The horizontal portion of the three-phase region of the intercellular substance isotherm is represented with a higher resolution in FIG. 7b. As can be seen from the graph, the horizontal section of the isotherm shown in FIG. 7a has a fine structure in the form of a wavy curve intersecting the horizontal line at points 1, 2, 3, 4, 5 corresponding to the solutions of the equation of state, of which only three 1, 3, 5 are physically feasible. Two other solutions 2, 4 are physically unworkable, since they are located on sections of the curve that contradict the stability condition of thermodynamic system $(\partial P/\partial V)_T < 0$.

It should be noted that the equilibrium isotherm of the intercellular substance, shown in FIG. 7, is consistent with the Maxwell rule, which has a theoretical justification for real gases, since the total area under the curve portions extending above the horizontal line is equal to the total area under the curve portions which extend below the horizontal line.

In the range of the dimensionless parameter 0<x<0.735 as x→0, the intercellular substance passes into a single-phase gaseous state (conglobulation). In the range of dimensionless parameter x>2.15, as x→∞, the intercellular substance passes into a single-phase state a solid phase (globule).

It is quite obvious that the phase states of the conglobulation and globule are incompatible with physic-and-chemical processes associated with metabolism of living tissue.

This implies understanding of the most important conclusions that native physiological state of living tissue can be realized exclusively in three-phase region of the thermal function, where all three phases of intercellular substance (conglobulation, liquid phase, globule) are in thermodynamic equilibrium. The normal physiological temperature and normal atmospheric pressure, at which physiological state of living tissue is realized, correspond to the triple point of intercellular substance, wherein thermodynamic equilibrium between all three phases of intercellular substance is realized.

Water is the closest physical analogue of the thermodynamic system at the triple point.

As is known, the triple point of water lies at 0.008° above the melting point at normal atmospheric pressure. Pressure at the triple point is much less than the atmospheric pressure and is approximately 4.58 mm Hg. art. The triple point for any substance is a completely determined quantity (in contrast to, for example, the boiling point, which depends on the pressure). This is connected with the fact that the triple point of water is the main reference point in the construction of the absolute thermodynamic scale of Kelvin temperatures, as well as the practical international temperature scale of Celsius. As it can be seen from the parameters of triple point of water, the equilibrium coexistence of ice, water vapor and liquid water under normal conditions is impossible. This circumstance seems to contradict ordinary observations—ice, water and steam are often observed all together. Nevertheless, there are no contradictions: the observed phase states of water are far from equilibrium and are put into practice only because of kinetic limitations of phase transitions.

Boundaries of three-phase region of the intercellular substance can be estimated from the average blood sugar values of 5 mmol/liter and capillary pressure of 20 mm Hg, characterizing the physiological norm: range the dimensionless parameter x [0.735-2.15] corresponds to the range of blood sugar values of 3,675-10.75 mmol/liter and the range of average capillary pressure of 14.7-43.0 mm Hg.

Property of thermoregulation of living tissue, well known from experience, and the high sensitivity of living tissue to external heat fluxes can be understood based on the analogy with the thermodynamic behavior of water at a triple point: heating water at a triple point leads to a phase transformation of ice into the liquid phase without changing its temperature; the amount of heat entering the system leads to a phase transformation of the ice into the liquid phase without changing its temperature.

Effect of external heat flux on the surface of living tissue (due to the variation in climatic thermal parameters) leads to its absorption and heating, which results in the breakage of the "sugar" crosslinks of the hyaluronic acid polymer chain with binding energy $k_B T$ and the increase in the volume of the intercellular space due to an increase in the mass fraction of water in the result of a phase transformation of intercellular substance, which leads to a change in the proportional relationships between the phases of the substance without changing its temperature.

Physics of Intercellular Substance:
Self-Organization of Microcirculation and Blood Circulation The intercellular substance isotherms shown in FIG. 7, allow us to understand the nature of self-regulation of micro streams of matter and energy in the spatial region, including the structural element of living tissue, schematically represented in FIG. 3.

As was shown above, the boundaries of three-phase region of intercellular substance can be estimated from the average blood sugar values of 5 mmol/liter and the capillary pressure $P_0=20$ mm Hg; article, characterizing the physiological norm:

to the interval [0.735-2.15] of the dimensionless parameter $x=P_0/P$ corresponds to hydrostatic pressure interval in the capillary [14.7-43.0] mm Hg. As known from experience, the average values of pressure at the inlet and outlet of the capillary are normal in the ranges [10-20] and [30-60] mm Hg; pillar; the average statistical values of capillary pressure at the outlet and inlet are respectively 15 mm Hg and 45 mm Hg. This implies an understanding of the important conclusion that the intercellular substance of living tissue surrounding the blood capillary along the entire length from the entrance to the exit (whose structural element is schematically represented in FIG. 3) is in a normal physiological condition in a three-phase region wherein all three phases of the intercellular substance coexist (conglobulation, liquid phase, globule).

Graphs presented in FIGS. 4-5. allow to understand the mechanism of the dependence of hydraulic pressure in the cardiovascular system on blood sugar level: increase in the concentration of blood sugar leads to an increase in the mass fraction of the liquid phase of the intercellular substance (swelling) in the initial section of the three phase region of the intercellular substance isotherm, which results in a decrease in the lumen of the capillary at the inlet (at point "Φ"). The lumen of capillary at the outlet (at point "v") decreases for a similar reason. Hydraulic resistance of the capillary of a local area of living tissue, determined by its lumen at the inlet and outlet, is thus a function of blood sugar (in the range of its regulation) and is the component that determines the resulting value of the hydraulic resistance of the circulatory system of the whole organism.

Increase in blood sugar leads to rise in the pressure gradient at the length of the capillary and, therefore, to a proportional increase in the mean arterial pressure due to the increase in arterial and venous pressures.

The mechanism described above also helps to explain the constancy of the volumetric flow of tissue fluid circulating in the intercellular space (microcirculation flow) and carrying the sugar transport to tissue cells and reverse transport of metabolic products to the microcirculation system.

Dependences shown on FIGS. 4-5 have singularities at the points "x=1" and "x=0.25": Elastic pressure at these points is equal to zero capillary pressure flow. Elastic pressure in the interval between these points is less than the capillary pressure of the zero flow and is zero at the point "x=0.46".

At a glucose concentration value of 4.5 mmol/liter, hydraulic pressure values are respectively:

25 mm Hg—at the point "x=1" (capillary pressure);

54.3 mm Hg—at the point "x=0,46" (pressure at the entrance to the capillary);

100 mm Hg—at the point "x=0.25" (the average arterial pressure);

6.7 mm Hg—at the point "x=3.72" (pressure at the outlet from the capillary).

Capillary pressure corresponding to the zero-flow pressure is numerically equal to colloid-osmotic (oncotic) pressure of the blood plasma, so when the blood sugar level increases and the average capillary pressure rises, the zero-point point shifts towards the venous end of the capillary. Such displacement of the point of zero flow leads to increase in the filtration area, growth of the filtration flow, and an increase in the resulting trans-capillary flow, which also appears to be linear function of the blood sugar level.

Thus, within the framework of the physical model under study, it is possible to obtain exact solutions for the dependence of the main parameters characterizing microcirculation and metabolism on blood sugar level and to explain the phenomenon of self-regulation of microcirculation flows.

As it is known [N. Amosov et al., (1969)], the power of contraction of heart ventricle varies directly in proportion to the average value of blood pressure (BP). The constancy of shock and minute volumes of heart is an essential feature of this dependence. The described dependence of the cardiac output power on the average pressure in the aorta is observed in rather wide, but limited limits, changes in blood pressure (approximately from 40-50 to 130-150 mm Hg). If these limits are exceeded, the effect of AD on the energy of contraction becomes diametrically opposite. BP is independent of the venous regulates the power of ventricle contraction. Heart-developed power changes under the influence of blood pressure exactly to the extent necessary to ensure the consistency of cardiac output. Due to this, heart can regulate the power of contraction within a wide range, retaining the shock volume predetermined by the influx.

Direct dependence of cardiac contraction on arterial resistance and venous inflow was first pointed out in his classic works by Starling (1914, 1918).

We have described the biophysical mechanism of self-regulation in the microcirculation system, which establishes a direct dependence of the hydraulic resistance and pressure in the microcirculation system on the blood sugar content, temperature and external pressure, makes it possible to explain the nature of the phenomenon known as self-regulation of the heart and vessels. Indeed, a change in the hydraulic resistance of capillary vessels, which occurs when the sugar content in blood changes (with constant ambient temperature and atmospheric pressure), leads to a change in pressure drop between the inlet and outlet of the capillary vessel and the change in blood pressure. Changes in blood pressure, in turn, lead to a change in cardiac output, in such a way that the shock and minute volumes of the heart remain constant.

Thus, change in the blood sugar level leads to proportional changes in pressure in the circulatory system—the average capillary pressure, pressure in the arterial and venous end of the capillary, arterial pressure and venous pressure change. Moreover, distribution of hydraulic pressure in the circulatory system is a unique function of the biochemical composition of the blood and more particularly to the sugar content in blood.

Physics of Intercellular Substance: Intercellular Microfluidics

Physics of the intercellular substance, the main points of which are discussed above, also make it possible to explain the mechanism of transport of tissue fluid in the intercellular space of living tissue, the main structural elements of which are cells, intercellular substance and a network of blood micro vessels (capillaries) that form the microcirculation system of the local area of living tissue. The specific structural element of the local area of living tissue is schematically represented in FIG. 3.

As it is known, the specific distance between the surfaces of neighboring cells is of the order of one micron. This implies the understanding of the obvious conclusion that the transport of tissue fluid from the capillary to the cell can be carried out through channels whose lumen is less than the characteristic intercellular distance.

Physical properties of the intercellular substance, considered above, allow us to explain the features of the transport of tissue fluid in the intercellular space.

The uneven distribution of hydraulic pressure (at a constant sugar concentration) along the capillary vessel (FIG. 5, curve 2) leads to an uneven distribution of osmotic pressure in the volume of tissue (FIG. 5, curve 1) and elastic pressure (FIG. 5, curve 3).

Gradients of pressure can be created both between adjacent capillaries, and within a single capillary. Such pressure gradients can lead to the formation in the intercellular substance of narrow channels, oriented along the pressure gradient, originating in the arterial region of the capillary and ending in the venous region. Transport of intercellular fluid is carried out through these channels, which are peculiar "microcapillaries" in the intercellular space. The driving force of the volumetric flow of tissue fluid through such a "microcapillary" is the difference in hydraulic pressures. In this case, distribution of tissue pressure along such channels, depending on the magnitude of the hydraulic pressure in the channel, obeys similar patterns describing the distribution of pressure in the capillary vessel.

Heat generated in the process of cellular metabolism is absorbed by intercellular water, which has a high heat capacity, and is transported along the intercellular space to the surface of the body and dissipates into the environment during evaporative cooling.

Specific feature of self-regulation of transport processes in the intercellular space is in the fact that magnitude of the volume flow of tissue fluid circulating in the intercellular space remains unchanged with changes in hydraulic pressure in the microcirculation system. The linear dependence of the rate of glucose uptake and the value of heat production on the concentration of sugar in the blood is a consequence of this property, since the density of glucose flow from the capillary to the cell is determined by the product of volume flow of the intercellular tissue fluid to the concentration of sugar in blood.

Physics of Intercellular Substance: Transport of Water Through the Epidermis

Physics of the intercellular substance, which main points were discussed above, makes it possible to explain the mechanisms of the process of heat and water transfer through the epidermis and more particularly to explain the high sensitivity of the epidermis of living tissue to external heat fluxes.

In natural (physiological) conditions, heat and water flows density in the process of evaporative cooling (with fixed climatic parameters of the environment) is determined by the gradients in the thickness of the epidermis of the physiological parameters characterizing the thermodynamic state of the intercellular substance—temperature, pressure and blood sugar concentration.

Figure 8:
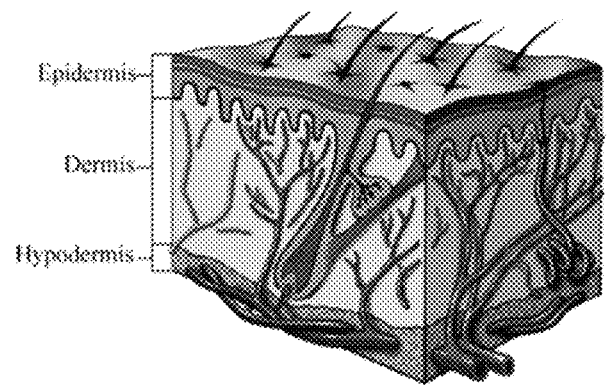
FIG. 8. Structure of the human skin surface.
Figure 8:
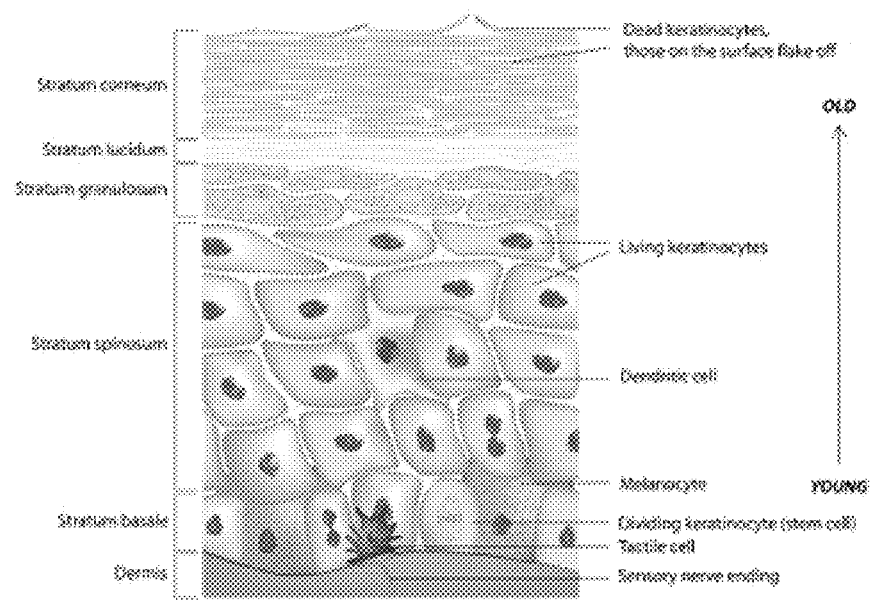

Based on the spatial structure of living tissue shown schematically in FIG. 8, it is understood that the mass fraction of water $M_{INTERCELL}$ in the intercellular space of a single tissue volume is much less than the mass fraction of water in this volume $M_0$:

$$N = M_{INTERCELL}/M_0 \ll 1.$$

Osmotic pressure of intercellular substance can be described through the mass fraction of water in the intercellular space of a unit volume of tissue, which can be considered as an effective concentration of intracellular water per unit volume.

The expression for osmotic pressure of the intercellular substance can be represented in a form that coincides formally with the Van't-Hoff equation for dilute solutions with a low concentration:

$$\Delta \pi = RT \times \Delta N = RT \times \Delta M / M_0, \qquad (10)$$

where $\Delta M = M_{INTERCELL}$,
T—temperature,
R—is the universal gas constant,
$M_0$—is the mass fraction of water in tissue volume.

On the other hand, as can be seen from the graphs 1 and 3 in FIG. 6, osmotic pressure of the intercellular substance is proportional to the concentration of sugar.

It follows that expression (10) for osmotic pressure can be represented in the form:

$$\Delta \pi(C) = RT \times \Delta N(C) = RT \times \Delta M(C) / M_0.$$

As it was shown above, heat generated in the process of cellular metabolism is absorbed by intercellular water, which has a high heat capacity (due to the high heat capacity of the water), is transported through the intercellular space to the surface of the body and dissipates into the environment during evaporative cooling.

In the dynamically equilibrium (stationary) natural state of living tissue, mass transfer from deep layers of epidermis to the surface is determined by the gradient of chemical potential, which by definition is equal to the effort for transferring one mole of substance.

In general case, the expression for the difference in the chemical potential $\Delta \mu$, considering the effect of the differences in hydraulic pressure $\Delta P$, temperature $\Delta T$ and concentration $\Delta N$, is as follows:

$$\Delta \mu = RT \times \Delta N + V \times \Delta P - S \times \Delta T = \mu_0 + RT \times (N_{IN} - N_{UP}) + V \times (P_{IN} - P_{UP}) - S \times (T_{IN} - T_{UP}), \qquad (11)$$

where
$\Delta P$—is pressure difference,
$\Delta T$—is temperature difference,
$\Delta N$—is the difference between effective concentration of intercellular water.
$N_{IN}$—is the effective concentration of intercellular water in deep layer.
$N_{UP}$—is the effective concentration of intercellular water in the surface layer.
V—is the volume of tissue corresponding to the unit area of the surface layer,
$P_{IN}$—is hydraulic pressure in deep layer,
$P_{UP}$—hydraulic pressure in the surface layer,
S—is the entropy of intercellular substance in a unit volume of tissue,
$T_{IN}$—is temperature of tissue in the deep layer,
$T_{UP}$—temperature of tissue in the surface layer, The expression describing the power of mass transfer process J is determined by the gradient of chemical potential $\Delta \mu / \Delta X$ and by microflow of water j:

$$J = X_j \times j, \text{ where}$$

$X_j = \Delta \mu / \Delta X$—is a driving force of the process, equal to the gradient of the chemical potential at the thickness of the epidermis $\Delta X$.

The mass flow is equal to:

$$j = \Delta N \times \Delta X / \Delta t.$$

The expression describing the power of the mass transfer process has the form:

$$J = X_j \times j = (\Delta \mu / \Delta X) \times (\Delta N \times \Delta X / \Delta t) = \Delta \mu \times \Delta N / \Delta t, \qquad (12)$$

The external influences on the epidermis of living tissue and more particularly to external heat fluxes lead to a change in the gradient of the chemical potential (11), caused by the change in the water content in the intercellular space as a result of absorption of thermal power and, as a consequence, to the change in the power of the mass transfer process.

It should be noted that the effects of compression and expansion of the intercellular substance can also be stimulated, by using a constant electric field. Electrostatic field (constant electric current) leads to the appearance of electrokinetic phenomena in the epidermis of living tissue and more particularly to the phenomenon of electro-osmosis caused by a change in the equilibrium distribution of electrical ions of tissue fluid in tissue volume, which in turn leads to disruption of the system's mechanical equilibrium and to a change of water content in the intercellular space.

Method for Measuring the Thermal Effect and Metabolic Rate of Human Living Tissue Method of micro-calorimetric measurement of thermal effect of the of the local area metabolism of living tissue is to measure the temporal dynamics of transfer processes (heat and mass transfer) that occur in epidermis upon application (with a metered pressure) on the surface of the stratum corneum of heat and waterproof applicator, excluding heat transfer and evaporation of water from the local limited surface of epidermis into the environment and forming a closed thermodynamic system in the local volume of tissue under the applicator.

Figure 9:
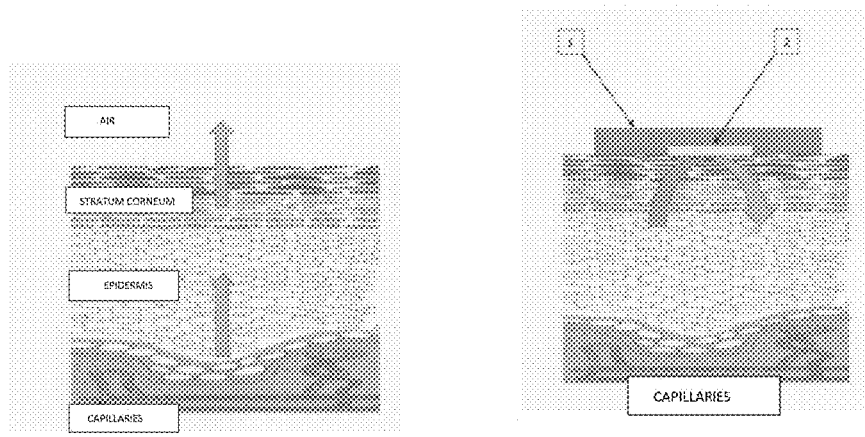
FIG. 9. Mode of operation of microcalorimeter of the thermal metabolic effect on the local area of human living tissue.

Microcalorimeter of thermal effect of the local part of living tissue metabolism is schematically represented in FIG. 9.

It is quite obvious that the epidermis of living tissue under natural conditions is an open system that is in thermal and diffusional contact with the environment. FIG. 9 (figure on the left) shows the direction of heat and water flows through the epidermis in natural unbalanced (nonequilibrium) stationary conditions. Driving forces of heat and mass fluxes through epidermis (from depth to surface) are the temperature and chemical potential gradients, respectively:

$$T_{skin} > T_{sc}; \mu_{skiin} > \mu_{sc}.$$

FIG. 9 (figure on the right) shows a closed system that is formed in the volume of tissue under the applicator, eliminating thermal and diffusional contact of living tissue with environment. The applicator (1) with diameter $D \gg L_{skin}$ (where $L_{skin}$ is a thickness of epidermis), impenetrable to heat and water, installed with a metered pressure on the surface of stratum corneum, forms a closed epidermal system (figure on the right) in thermal and diffusion contact with thermostat (a large reservoir of energy and particles), the role of which is performed by the microcirculation system (circulating water in a system of capillaries located in the deep layer of skin). The set of "system+vessel" presents a closed complex.

The temporal dynamics of transport processes (heat and water) in a closed epidermal system is controlled by sensors (2) of physiological parameters (temperature, osmotic pressure of intercellular substance, elastic pressure) located on the surface of the stratum corneum under the applicator.

It is quite obvious that changing the boundary conditions by imposing the applicator (with dosed pressure) on the surface of the stratum corneum, which eliminated heat and mass transfer, leads to disruption of the natural dynamic equilibrium in epidermis and also leads to the appearance of transient process, during which a spontaneous transition of epidermis tissue under the applicator from a less probable unbalanced to more probable steady (equilibrium) state, corresponding to the maximum entropy, which can be considered as a state of local thermodynamic equilibrium. After establishing the thermodynamic equilibrium in the volume of tissue under the applicator, temperature and chemical potential of the surface layer of epidermis become equal to the temperature and chemical potential of a deep layer (thermostat):

$$T_{sc}=T_{skin}; \mu_{sc}=\mu_{skin}.$$

It is quite obvious that in the state of local thermodynamic equilibrium in the volume of tissue under the applicator, equilibrium distributions of macroscopic parameters are being established (amount of water M, elastic pressure P, temperature T) in the volume of tissue under the applicator.

This implies an understanding of the important conclusion that values of variables of thermodynamic tissue state in the depth layer of tissue (in approximation of stationarity of physiological parameters) can be determined by measuring the temporal dynamics of these parameters in the stratum corneum surface under the applicator, forming a closed epidermal system.

Equation, describing heat balance of tissue under the applicator at the initial time, after changing the boundary conditions by applying an impenetrable applicator to the stratum corneum surface, can be obtained from phenomenological equation (5) and represented in the following form:

$$\Delta H/\Delta t = W_{MET}-(J+W_R+W_C+W_T)=W_{MET}-J-W_{SKIN}, \quad (14)$$

$W_{MET}$—heat production,
$W_R$—heat transfer by radiation (radiant heat exchange),
$W_C$—heat transfer by convection,
$W_T$—heat transfer from the epidermis surface by thermal conductivity,
J—convective heat transfer by evaporation in the process of imperceptible perspiration (steam cooling),
$W_{EXT}$—heat flow through the building envelope between the place of subject location and external environment,
H—enthalpy (heat content) of tissue.

It should be noted that, in contrast to equation (5), describing heat balance of living tissue in the unbalanced stationary state, heat transfer capacities $W_{SKIN}$ and mass transfer J are recorded in the equation (14) with a "+" sign.

In general case, the spontaneous transition of a closed thermodynamic system under the applicator from initial (less probable) unbalanced state to the final (more probable) steady state corresponding to the maximum entropy, can be described with the basic equation of thermodynamics, connecting the enthalpy of tissue with its natural state variables:

$$\Delta H = T \times \Delta S + S \times \Delta T + V \times \Delta P + \mu \times \Delta N, \text{ where}$$

H—enthalpy,
S—entropy,
T—temperature,
V—volume,
P—pressure,
μ—chemical potential,
N—amount of substance.

The process of transition of the closed system of tissue epidermis under the applicator from the initial unbalanced state to the final most potential state of local thermodynamic equilibrium can be described by the basic equation of thermodynamics connecting the enthalpy of tissue with its natural variables of the thermodynamic state, which can be written in the following form:

$$\Delta H = \Delta Q_{MET} + \Delta Q_{\Delta T} + K_M \times \Delta M + K_P \times \Delta P; \quad (15)$$

or $$\Delta H = \Delta Q_{MET} + K_T \times \Delta T + K_M \times \Delta M + K_P \times \Delta P; \quad (16)$$

ΔH—change in enthalpy, as a result of tissue transition in the region under the applicator into the local thermodynamic equilibrium state;
$\Delta Q_{MET}$—amount of heat entering the volume of tissue under the applicator in the process of metabolism,
$\Delta Q_{\Delta T}$—amount of heat entering the volume of tissue under the applicator during heat transition caused by the temperature gradient between the surface and depth;
ΔT—change in of the stratum corneum (SC) temperature, as a result of tissue transition in the area under the applicator to the local thermodynamic equilibrium state;
ΔM—change in the amount of water in tissue under the applicator during the mass transfer caused by the gradient of chemical potential between the surface and depth;
ΔP—change in the elastic pressure of tissue under the applicator during mass transfer;
$K_T$, $K_M$ и $K_P$—phenomenological constants, which are determined by calibration.

Let's consider the specific nature of time dynamics of the transient process of mass transfer under the applicator.

Method for measuring the water content in the epidermis is to measure the time dynamics of the mass transfer process that occurs when the waterproof applicator is applied (by metered pressure) to the stratum corneum surface, which excludes evaporation of water from the local surface of stratum corneum.

Water content in the intercellular space of epidermis can be determined using a method, which essence lies in continuous measurement of temporal dynamics of the amount of water in local volume of epidermis under the waterproof applicator.

One of the effective practical methods for determining the water content in the intercellular space of epidermis is to measure this parameter by recording the time dynamics of water amount in the stratum corneum surface (SC) of epidermis using water quantity sensor 2 (FIG. 9) located on the stratum corneum surface under the applicator 1. This method allows analyzing the dynamics of water amount and its equilibrium content in the intercellular space of deep layers in the skin and subcutaneous tissues by the nature of temporal dynamics of the amount of water in SC.

The waterproof applicator, which is superimposed on the SC surface with a metered pressure, eliminates the possibility of natural evaporation of water from the SC surface during the imperceptible perspiration. Modification of the natural boundary conditions that determine heat exchange between tissue and environment leads to disruption of the natural equilibrium of water and heat transfer processes—the resulting trans-capillary flux of water at the depth of dermis, flux of water entering the surface of epidermis from the dermis layers, in place of capillary vessels location, and by the flow of water evaporating from the stratum corneum (SC) surface. Violation of the natural balance of heat and mass fluxes leads to the emergence of a local swelling in the intercellular substance of epidermis in the volume of tissue under the applicator, which is accompanied by increase in the surface temperature caused by the absorption of heat in the local area beneath the applicator.

As the intercellular tissue is swelling, equalization of temperature and chemical potential occur through the epidermal thickness under the applicator.

Figure 10:
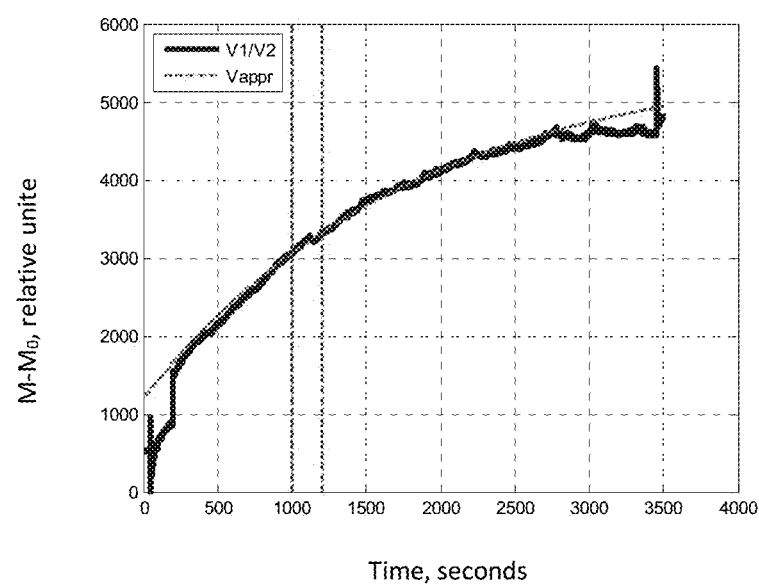
FIG. 10. Specific temporal dynamics of the amount of water in epidermis in relative units, caused by a change in the boundary conditions as a result of applying a waterproof applicator to the surface of stratum corneum of epidermis. Approximation of the time dynamics of the exponent is shown by a dashed line.

FIG. 10 shows the characteristic temporal dynamics of the amount of water in the epidermis during the mass transfer caused by the change in the boundary conditions as a result of applying the waterproof applicator to the SC surface, which excludes the transfer of water and heat from the surface of controlled body region.

As it follows from the graph, water content in the SC, which is equal to $M_{SC}(t_0)$ at the reference time, tends towards a new equilibrium level $M_{SC}(t=\infty)$ corresponding to the water content $M_0(t_0)$ in the deep layer of epidermis:

$$M_{SC}(t) \to M_0(t_0), \text{ at } t \to \infty.$$

In the simplest case, with constant values of blood sugar and climatic parameters, the temporal dynamics (swelling process) of the amount of water $M_{SC}(t)$ in the stratum corneum surface is described by one exponent:

$$M_{SC}(t)=M_{SC}(t=\infty)\times[1-\exp(-t/\tau_M)]=M_0(t_0)\times[1-\exp(-t/\tau_M)], \quad (17)$$

where $\tau_M$—time constant of the mass transfer process. The relationship between the amount of water $M_0(t=t_0)$ in the depth of epidermis and the power of mass transfer process $J_M(t_0)$ at the initial instant of time ($t=t_0$), corresponding to the moment of pressing the applicator to the stratum corneum (SC) surface can be determined by differentiating expression (14):

$$dM_{SC}(t_0)/dt = J_M(t_0) = M_0(t=t_0)/\tau_M. \quad (18)$$

Thus, temporal dynamics of the amount of water in epidermis can be controlled by measuring time dynamics of the amount of water in the stratum corneum surface by non-invasive method.

Different physical and chemical methods based on different physical principles are applicable to measure the amount of water in the stratum corneum. In particular, the following methods are usually used to measure the amount of water in the stratum corneum: electrometry methods, based on the measurement of electrophysical characteristics (electrical conductivity, dielectric permittivity); spectral methods based on ranging the spectral characteristics (reflection and absorption coefficients); opto-acoustic methods; thermophysical methods based on measurement of thermophysical characteristics (thermal conductivity, heat capacity); electrochemical methods, etc.

Figure 11:
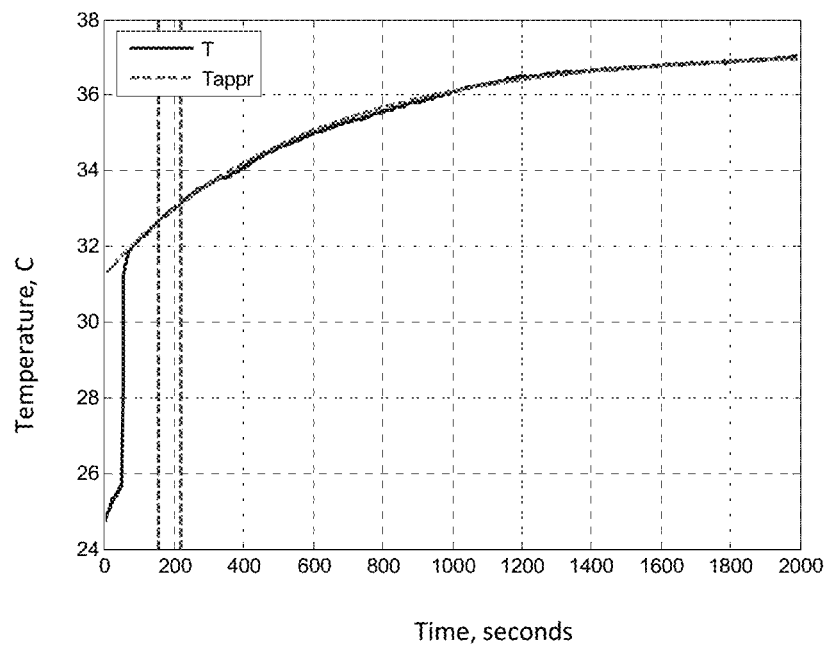
FIG. 11. Specific temporal dynamics of the stratum corneum surface temperature of human epidermis upon imposition of a heat-resistant applicator (blue curve). The exponential approximation of the temperature time dynamics is shown by a dashed line.

FIG. 11 shows the specific time dynamics of the SC temperature in the process of heat transfer caused by a change in the boundary conditions as a result of applying heat and waterproof applicator to the SC surface, excluding transfer of water and heat from the surface of the controlled area of the body.

Temporal dynamics of heat transfer (temperature and heat quantity) in tissue volume under the applicator, in the simplest case, with constant values of blood sugar and climatic parameters, can also be described by the exponent:

$$T_{SC}(t)=T_{SC}(t_0)+T_{PCЭ}(t=\infty)\times[1-\exp(-t/\tau_T)]=T_{SC}(t_0)+T_0(t_0)\times[1-\exp(-t/t_T)], \quad (19)$$

where
$T_{SC}(t_0)$—temperature of the stratum corneum under the applicator at the reference time (initial instant of time)
$T_{SC}(t)$—temperature of the stratum corneum under the applicator,
$T_0(t_0)$—temperature of tissue in the deep layer of epidermis beneath the applicator at the reference time.

The relation between temperature $T_0(t=t_0)$ in the depth of epidermis and rate of change in SC temperature at the initial instant of time $t=t_0$, corresponding to the moment of pressing the applicator to the SC surface, can be determined by differentiating expression (16):

$$dT_{SC}(t_0)/dt = T_0(t=t_0)/\tau_T.$$

Density of heat flux directed from depth to the surface, in the volume of tissue under the applicator, at the initial time $t_0$ is determined by the temperature gradient through the thickness of epidermis layer:

$$W_{SC}(t)/K_T = \Delta Q_{\Delta T}/\Delta t = T_0(t_0) - T_{SC}(t) = \tau_T \times [dT_{SC}(t_0)/dt] - T_{SC}(t_0).$$

Thus, values of macroscopic parameters of tissue in the depth layer under the applicator can be determined by measuring derivative of time dynamics of these parameters at the initial section.

This implies an understanding of the important conclusion that equation (16) can be written in the form of a differential equation connecting heat and mass fluxes in the volume of tissue under the applicator:

$$\Delta H/\Delta t = \Delta Q_{MET}/\Delta t + K_T \times \Delta T_{SC}/\Delta t + K_M \times \Delta M_{SC}/\Delta t + K_P \times \Delta P/\Delta t;$$

or $\Delta H/\Delta t = W_{MET} + W_{SKIN} + J_{SKIN} + K_P \times \Delta P/\Delta t.$ \quad (20)

The obtained equation (20) coincides, up to the member of equation $K_P \times \Delta P/\Delta t$, describing the change in tissue volume, with equation (14) describing heat balance in tissue volume under the applicator:

$$\Delta H/\Delta t \; W_{MET} + (J + W_R + W_C + W_T) = W_{MET} + J + W_{SKIN}. \quad (21)$$

Obviously, it is possible to define $W_{MET}$ metabolism rate from the last equation (21) by measuring the $J+W_{SKIN}$ fluxes, if the value of $\Delta H$ and enthalpy change rate $\Delta H/\Delta t$ can be measured or determined by any independent method. In a similar way, with the known value of change in enthalpy $\Delta H$ in a given time interval $\Delta t$, it is possible to determine the thermal effect of the $\Delta Q_{MET}$ metabolism from equation (16), which represents the integral form of equation (21), by measuring the amount of water $\Delta M$ and elastic pressure $\Delta P$ in the selected time interval.

In the course of experimental studies, performed by us, the dependence of thermodynamic characteristics of human epidermis on physiological and physical and climatic parameters were studied and it was established that heat content of tissue is determined by the amount of water in the intercellular space of epidermis.

The expression for the thermal function or heat content (enthalpy) in the deep layer of tissue, depending on climatic parameters, has the following form:

$$H=H_0(T_{skin},P_{sensor}) \times \Theta(T_{room}, T_{ext}, RH_{room}, P_{atm}), \quad (22)$$

$T_{skin}$—temperature of the depth layer under the applicator,
$P_{sensor}$—pressure of applicator on the epidermis surface,
$T_{room}$—temperature of the air in the measurement room,
$T_{ext}$—ambient air temperature behind the enclosing structure,
$RH_{room}$—relative humidity of the air in the measurements room,
$P_{atm}$—atmospheric pressure.

Figure 13:
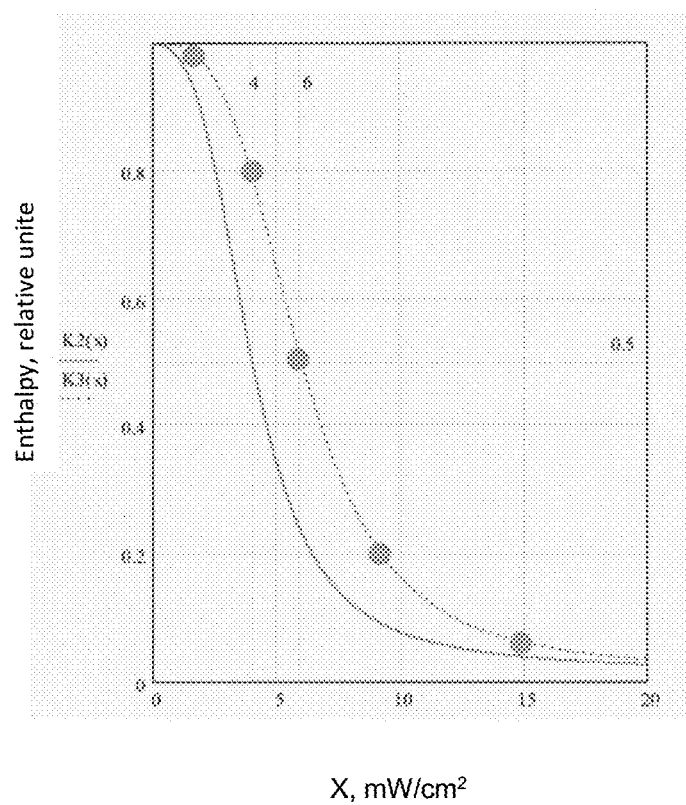
FIG. 13. The experimental dependence of the epidermis heat content (in relative units) on the value of external heat flux through the enclosing structure (in relative units).

FIG. 13 shows the experimental dependence of heat content of tissue on climatic parameters, for fixed physiological parameters.

During the transition of tissue under the applicator to the state of local thermodynamic equilibrium, the enthalpy of surface layer of epidermis (at steady-state climatic parameters, temperature of the deep layer of the epidermis $T_{skin}$, and contact pressure of applicator $P_{sensor}$) changes within the time interval of transition process $\tau_M$ from 0, in the surface layer of epidermis, to H value, equal to the enthalpy in the deep layer of epidermis, which is determined from the expression (22):

$$\Delta H = H - 0 = H_0(T_{skin}, P_{sensor}) \times \Theta(T_{room}, T_{ext}, RH_{room}, P_{atm}). \quad (23)$$

As it was shown above, for stationary values of physiological parameters of living tissue under the applicator, rate of change of thermodynamic parameter in the surface layer of epidermis is uniquely determined by the value of this parameter in the deep layer, wherein the capillary network of microcirculation system is located.

The relationship between enthalpy $H_0(t=t_0)$ in the deep layer of epidermis and rate of enthalpy change in the surface layer at the initial instant of time $t=t_0$, corresponding to the moment of pressing the applicator onto the SC surface, is determined by the expression:

$$\tau_M \times dH(t_0)/dt = H_0(t=t_0) \times \Theta(T_{room}, T_{ext}, RH_{room}, P_{atm}). \quad (24)$$

The method of micro-calorimetry of local tissue metabolism is reduced to real-time measurement of the temporal dynamics of physiological (internal) tissue parameters ($T_{SKIN}$ and $J_M$), characterizing heat transfer caused by a change in the boundary conditions as a result of applying the heat and waterproof applicator to the epidermis surface, as well as climatic (external) parameters of the environment ($T_{ROOM}$, $RH_{ROOM}$, $T_{EXT}$, $RH_{EXT}$, $P_{ATM}$), and calculation (with a known value of the constant $K_0$, which is a characteristic of the intercellular substance and determined by calibration) of the thermal effect and metabolic rate using equations (16) and (21).

Peculiarity of the method lies in the fact that along with the measurements of heat flux of heat exchange caused by the temperature gradient and heat flux due to evaporative cooling in the process of imperceptible perspiration and measurements of microclimate parameters (temperature and humidity, atmospheric pressure) of the measurements room, with the purpose of increasing accuracy by reducing the dependence of the measurement error on the influence of external conditions, ancillary measurements of the physical and climatic parameters of the environment affecting the characteristics of living tissue are carried out, measurement errors are determined from the known heat transfer of the local tissue from the physical and climatic factors of the environment and the instantaneous signal values of measured physiological parameters.

DESCRIPTION OF THE PREFERRED EMBODIMENT(S)

Figure 14A:
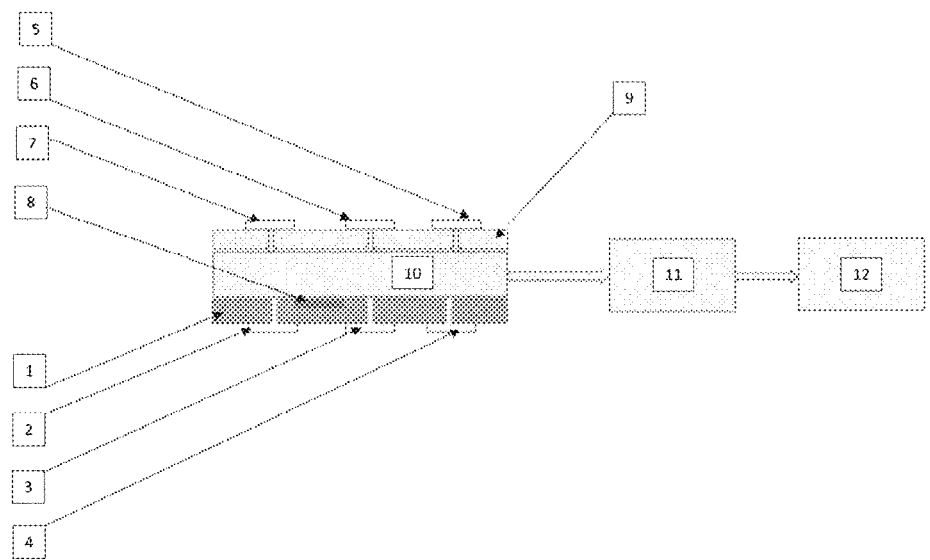
FIG. 14 (a). Multi-sensor device circuit for measurements in the "climate control" mode.
Figure 14B:
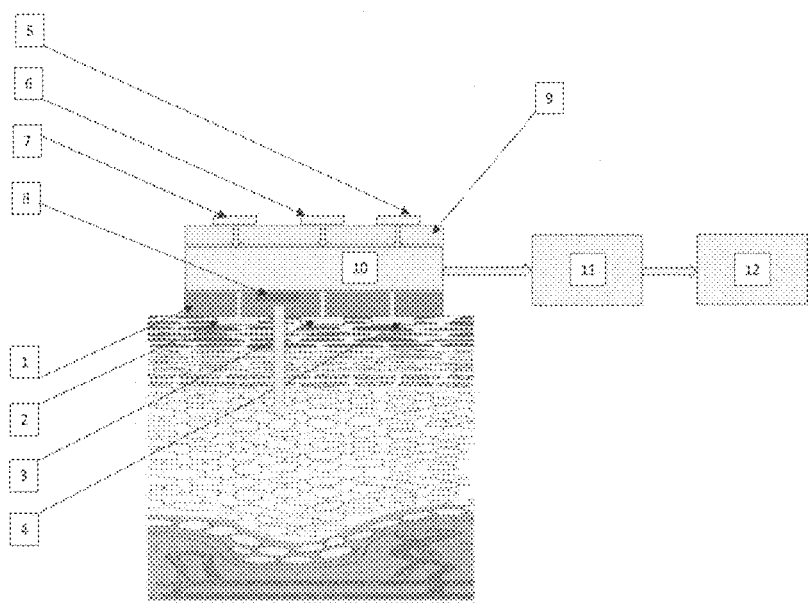
Figure 14:
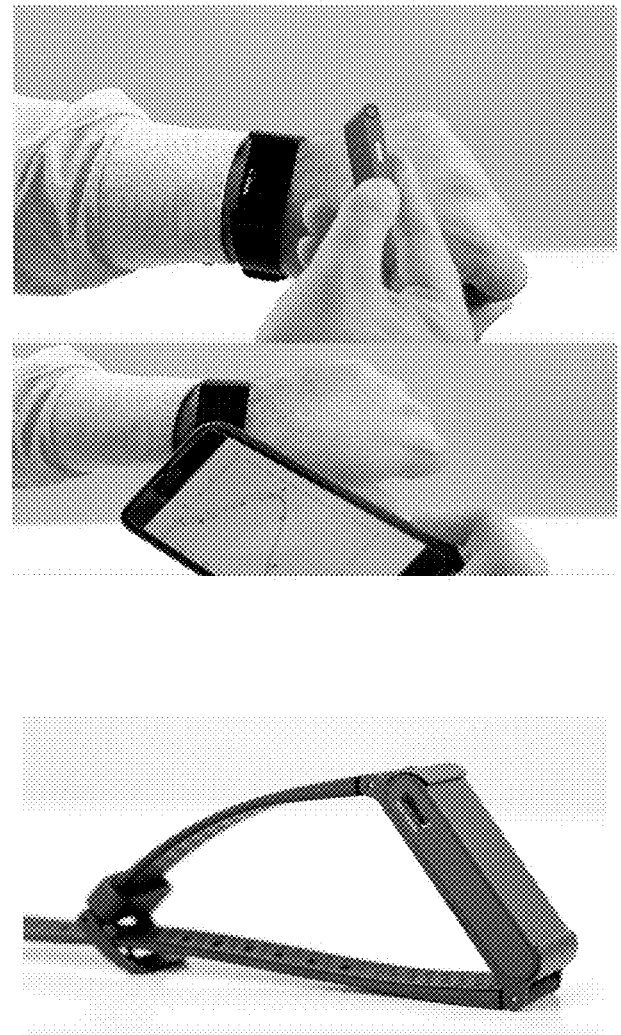

The proposed method for monitoring blood sugar by measuring thermal effect and metabolic rate of the local area of living tissue can be realized using a multi-sensor device, the schematic diagram of which is shown in FIG. 14.

The device contains two groups of sensors, one of which is designed to measure the physiological parameters of the local area of living tissue, and the second group of sensors to measure environmental climatic parameters.

The device includes an applicator 1 impermeable to heat and water, having an upper and a lower surface that is capable of being applied to the skin at a metered pressure, device 8 for creating a calibration effect on the controlled tissue site under the applicator, an installation platform 9 for securing the sensors of climatic parameters (made in the form of a printed circuit board located above the applicator), sensors of climatic parameters located on the mounted platform 9, sensors of physiological parameters located under the applicator, on the inner side of applicator on the stratum corneum surface, wherein the signals from the mentioned sensors are applied in series to the inputs of amplifier unit 10 and/or the analog-to-digital converter (further referred to as A/D converter) installed on the upper surface of the applicator 1; an information processing unit 11; and information display unit 12.

The microprocessor for real-time processing of signals from sensors of physiological parameters of the local tissue region under the applicator and sensors of environmental parameters is an information processing unit 11.

In one of the preferred embodiments, information processing unit 11 is located on the upper surface of the applicator 1, in the other—it is remote and is wired with AD converter.

The information display unit 12 is a smartphone or a personal computer. In this connection, communication of the multi-sensor device with the information display unit 12 can be in various embodiments, both wireless and wired (via USB channel).

At least water quantity (osmotic pressure) sensor 2, which helps determining the amount of water in the intercellular space of tissue in the local volume under the applicator at a controlled depth on which the local thermodynamic equilibrium is being achieved; sensor 3 of the stratum corneum temperature, which allows determining the temperature of skin surface under applicator, sensor 4 of the elastic pressure of tissue under applicator are used as sensors for measuring the dynamics of physiological parameters of the local tissue area under applicator.

At least temperature sensors 5, detecting air temperature in the measurements room, relative air humidity sensor 6 in the room where measurements are taken, heat flow sensor 7 through the enclosing structure between the room and external environment is used as sensors of environmental climatic parameters. The heat flow sensor is located on the installation platform.

In an alternative embodiment of the method, time variations of heat flux through the enclosing structure between the room and the external environment can be easily controlled by accurately measuring two parameters—the room air temperature and the outside temperature behind the wall. In this case, the air temperature in the room is determined by measuring with a temperature sensor located on the installation platform, and its current value corresponding to the published weather station data that is entered into the program for calculation is taken for ambient air temperature.

Peculiarity of the proposed multisensory device is that the measuring method provides for the possibility of operating the device in two different modes:
- in the "climate control" mode for measuring climatic parameters of the environment;
- in the "microcalorimeter" mode for measuring the thermal effect and intensity of metabolism of a local area of living tissue.

Circuit of the multi-sensor device for performing measurements in the "climate control" mode is shown in FIG. 14a. In this mode, signals from the ambient climate sensors (temperature sensors 5 and room humidity 6, external heat flow sensor 7 between the measurement room and the external environment) located on the mounting platform 9 are fed to the inputs of the instrument amplifiers and/or (block 10) located on the outside of the applicator 1, after which they enter the information processing unit (11) connected to the information display device (12), on the screen of which in real time, the current values of the climatic parameters of the environment are displayed.

The diagram of the multi-sensor device for performing measurements in the "microcalorimeter" mode is shown in FIG. 14 (b). In the time interval before the start of measurements in the "microcalorimeter" mode, the device operates in the "climate control" mode and registers in real time the current values of the climatic parameters that are recorded in the microprocessor's memory and are used later in the process of processing the signals of physiological sensors.

In the "microcalorimeter" mode, the signals of the physiological sensors (the water quantity sensor 2, the temperature sensor 3 and the pressure sensor 4) located on the inner surface of the applicator 1, are fed to the inputs of instrument amplifiers and/or an analog-to-digital converter (block 10), after which come to the information processing unit 11, wherein the processing of the signals of the sensors of physiological parameters is performed taking into account the indications of the climatic parameters sensors.

Processed information is transmitted to the display device 12, on the screen of which in real time the current values of the measured parameters and/or metabolic rate of the parameters are displayed.

It should be noted that with the help of the multi-sensor device described above, simultaneous real-time measurements can carry out both physiological parameters and climatic parameters. In this case, inputs of instrument amplifiers and/or analog-to-digital converter 11 receive signals from all sensors of the multi-sensor device and the current values of climatic parameters are used to process the signals of physiological parameters.

For practical implementation of the multi-sensor device, industrial certified sensors for measuring climatic parameters, as well as certified sensors for measuring the temperature of the stratum corneum and the elastic pressure of the epidermis can be used.

For example, Honeywell sensors can be used as a sensor for measuring the temperature of the stratum corneum.

For example, Sensirion sensors can be used as a sensor for measuring climatic parameters of temperature and humidity.

Sensors based on a piezoelectric element can be used as a sensor for measuring elastic pressure.

The amount of heat flow through the enclosing structure between the room and the external environment can be measured with conventional heat flow sensors based on measuring the air temperature gradient towards the wall surface (enclosing structure). The heat flow sensor is located on the installation platform.

Water quantity sensor (2), which registers the dynamics of water transfer in the epidermis by recording the temporal dynamics of the water content in the stratum corneum of the epidermis, can be based on different physical and chemical methods based on different physical principles. In particular, the following methods are applicable to measure the amount of water in the stratum corneum-electrometry methods based on measuring the electrophysical characteristics of SC (electrical conductivity, dielectric constant); spectral methods based on measurement of spectral characteristics (reflection and absorption coefficients); optical-acoustic methods; thermophysical methods based on measurement of thermophysical characteristics (thermal conductivity, heat capacity); electrochemical methods, etc. Also, water quantity sensor can be based on measuring the hydraulic pressure in the microcirculation system, on measuring the elastic pressure.

Devices for measuring the amount of water in the epidermis are described in the patent [27].

In case of using an electrometric sensor, the amount of water in the epidermis can be determined by measuring electrical characteristics (electrical conductivity and/or permittivity) of the stratum corneum on alternating or direct current. In particular, temporal dynamics of the process of swelling of the intercellular substance can be recorded from the temporal dynamics of the transverse electrical resistance of the stratum corneum of the epidermis. An increase in the amount of water in the intercellular space leads to an increase in its quantity in the stratum corneum, which leads to an increase in the electrical conductivity of the surface layer of the epidermis. Typical dynamics of the transverse electric resistance, measured in this way, is shown in FIG. 10. In natural conditions, in the absence of a measuring electrode on the surface of the body, these streams are balanced and ensure the transfer of heat generated in the process of cellular metabolism from the deep layers of tissue to the surface of the body. Physical mechanism of the processes of transport of water and heat from depth to surface was considered above in the section "Intercellular water transfer through epidermis".

If spectral sensor is used, the amount of water in epidermis can be determined by measuring the spectral characteristics (reflection coefficient and/or absorption coefficient) of the stratum corneum for electromagnetic radiation with a wavelength near the absorption line due to water content in the SC. In particular, temporal dynamics of the process of swelling of intercellular substance can be recorded according to the temporal dynamics of the coefficient of reflection of the stratum corneum of epidermis. Increase in the amount of water in the intercellular space leads to a change in the spectral characteristic of the stratum corneum (SC), caused by a change in the amount of water in the SC.

The dosage calibration action is selected from the group consisting of external pressure, local decompression, heating, cooling, electric current or voltage and magnetic field.

For example, device that generates pulses of electrical voltage or current through stratum corneum can be used as a device for creating a calibration effect, such device can determine current value and direction of microcurrents of tissue fluid in the intercellular substance in the deep layer of epidermis, by measuring the kinetic characteristics of mass transfer caused by electro-kinetic phenomena and more particularly toby electro-osmosis.

In alternative embodiments, device for generating calibration action is a thermal power source made in the form of a resistor or Peltier element, or a device for creating a metered pressure on the surface of the applicator.

In one embodiment, the applicator is flat, in the other, in the form of a measuring hermetic capsule forming a closed cavity with diffusion and thermal contact with the skin. In this case, working surface of said capsule facing the skin is made in the form of a rigid membrane, permeable or semi-permeable to water and heat. In one of the embodiments, cavity is filled with water absorbing material. With such alternate embodiments of the applicator structure, respectively, a sensor for the amount of water in the intercellular space of the local tissue volume may be in the form of a water vapor concentration sensor or a water vapor pressure sensor or a sensor based on spectrometric or thermophysical methods for measuring water vapor characteristics.

Applicator (1) impenetrable for water and heat with water level sensors (intercellular osmotic pressure 2) fixed to its lower surface, temperature 3 and elastic pressure of the epidermis on the applicator 4, is fixed on the surface of the stratum corneum of the epidermis, for example, on the surface of the hand, with external dosage pressure and is attached in one embodiment using straps. It follows that the measurement can be made on any part of the surface of the human body, free from the hair, with the exception of the areas of the body where the sweat glands are located, which are activated as a result of emotional impact. Palms of hands are the example of such area.

Figure 15:
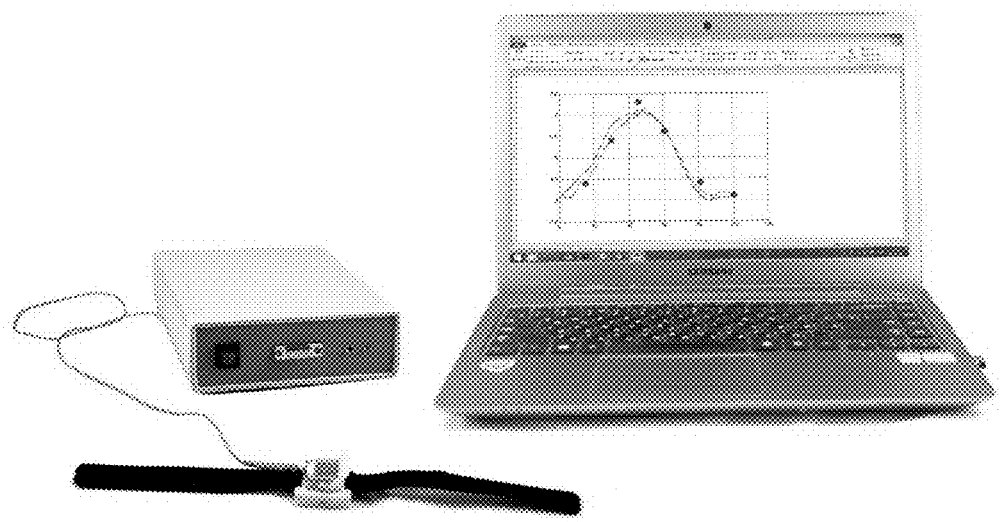
FIG. 15 (a). A photograph of the exterior of prototype microcalorimeter for noninvasive measurement of blood sugar level and rate of local tissue metabolism. b) Photograph of a prototype of a multi-sensor microcalorimeter for bloodless measurement of blood sugar. Sensor of the microcalorimeter is fixed on the hand surface and is attached by straps provided with "Velcro".
Figure 15:
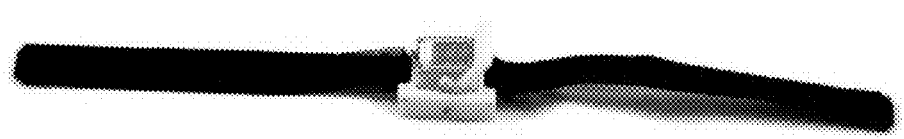

The expected size, appearance and design of the multitouch device are shown in FIG. 14 (c). FIG. 15 shows photos of the prototype microcalorimeter.

Process of measuring (signals recording) starts immediately at the moment of pressing at least one heat- and waterproof applicator to the SC surface or with 10-50 seconds delay from the moment of pressing.

Temporal dynamics of physiological parameters in the local closed tissue area under the applicator is measured in the "microcalorimeter" mode after applying the applicator to the skin surface, in particular, at least the following parameters are being measured—heat flow through the epidermis area under the applicator or surface temperature of the skin under the applicator, elastic pressure of tissue under the applicator, pressure created by the applicator on the surface of the skin, amount of water in the intercellular space of tissue at a controlled depth at the local thermodynamic equilibrium level. Heat flux is measured through a patch of epidermis under the applicator or a temperature at a controlled depth of $T_{skin}$, wherein local thermodynamic equilibrium is established, at a fixed pressure of $P_{sensor}$ applicator. This temperature can be determined by radiothermometric methods, or by changing the temporal dynamics of skin surface temperature under the applicator and heat flux through the epidermis to the surface. Upon which the instantaneous value of enthalpy is being calculated $H_0(T_{skin}, P_{sensor})$.

At the same time, before the beginning of measurement of physiological parameters or simultaneously with them in the regime of "climate control", the time dynamics of the climatic parameters of the environment, namely, at least atmospheric pressure $P_{atm}$, room temperature $T_{room}$ and relative humidity $RH_{room}$ in the room where the measurement is made, the temperature of the external environment $T_{ext}$ or external heat flow through the enclosing structure between the room and the external environment.

Measured data is delivered to the information processing unit 11, wherein the signals of the physiological parameters sensors are processed considering the indications of the climatic parameters sensors, in particular, the enthalpy of tissue is calculated taking into account the influence of climatic parameters, measuring the dynamics of the climatic factor $\Theta(T_{room}, T_{ext}, P_{atm}, RH_{room})$, depending on the value of the external heat flow at fixed values of the relative humidity of the air $RH_{room}$ and atmospheric pressure $P_{atm}$ and measuring the dependence of the enthalpy of tissue on external heat flux at different temperature values at a controlled depth of $T_{skin}$ at fixed values of the relative air humidity $RH_{room}$ and atmospheric pressure $P_{atm}$ according to the formula:

$$H=H_0(T_{skin}, P_{sensor}) \times \Theta(T_{room}, T_{ext}, P_{atm}, RH_{room}).$$

Where after, value of the thermal effect of $\Delta Q_{MET}$ metabolism of a local area of living tissue is calculated using the basic equation of thermodynamics, which connects the enthalpy of tissue with the variables of the thermodynamic state.

$$\Delta H = \Delta Q_{MET} + \Delta Q_{\Delta T} + K_M \times \Delta M + K_P \times \Delta P;$$

$$H_0(T_{skin}, P_{sensor}) \times \Theta(T_{room}, T_{ext}, RH_{room}, P_{atm}) = W_{MET} + W_{\Delta T}(T_{skin} - T_{room}) + J;$$

where
J—mass transfer power
$W_{\Delta T}$—power of heat flux due to temperature drop at a controlled depth wherein local thermodynamic equilibrium is established.

Thereafter, relative changes in blood glucose level are measured, proportional to the value of the thermal metabolism of the local area of living tissue.

To calculate blood glucose level, calibration procedure is performed, and the calibration parameters are determined in order to determine the constant coefficients necessary for calculating heat effect of metabolism of a local site of living tissue and calculate blood glucose level proportional to the value of the thermal metabolism of the local area of living tissue.

Number of sensors of the multi-sensor device described above can be increased by including additional sensors and sensors in the device that characterize the metabolism of a local area of living tissue and more particularly to blood biochemical parameters (for example, lactate in the blood), blood acidity, frequency of cardiovascular contractions. Additional sensors for through-cut measurements can be installed on the inside of the applicator and integrated with the physiological and climatic parameters sensors described above into a single measuring circuit as part of a multisensor device.

Method for Determining the Content of Biochemical Components of Blood by their Content in the Stratum Corneum of the Epidermis Content of any biochemical component in blood can be determined by measuring its content in a bloodless manner in the stratum corneum surface using the method described in the section "Method for measuring the thermal effect and metabolic rate of local tissue," by analogy with the method for determining the amount of water in the intercellular space of the epidermis. The content of biochemical component in the stratum corneum is determined by means of an electrochemical biosensor or by any other possible means. After applying an applicator to the SC surface with a dosed pressure in tissue volume, mass transfer occurs under the applicator due to change in boundary conditions as a result of applying the applicator to the SC surface, which eliminates transfer of water and heat and biochemical component from the surface of the controlled area of body.

The content of an arbitrary biochemical component (substance) (for example, glucose G) in SC, equal to $M_{GSC}(t_0)$ at the initial time ($t=t_0$), tends towards new equilibrium level of $M_{GSC}(t=\infty)$ corresponding to blood glucose level $M(t_0)$: $M_{GSC}(t) \to M_{0G}(t_0)$ at $t \to \infty$.

In the simplest case, with a constant content of biochemical component (substance) G in blood and climatic parameters, temporal dynamics of the amount of $M_{GSC}(t)$ substance in the stratum corneum surface of epidermis is described by a single exponent:

$$M_{GSC}(t) = M_{GSC}(t=\infty) \times [1-\exp(-t/\tau_X)] = M_0(t_0) \times [1-\exp(-t/\tau_G)],$$

where $\tau_G$—time constant of the process of glucose mass transfer (controlled substance).

The relationship between the amount of substance $M_{0G}(t=t_0)$ in the depth of epidermis and power of mass transfer process $J_{GM}(t_0)$ at the initial moment of time ($t=t_0$), corresponding to the moment of pressing the applicator to SC, can be determined with by the following expressions: $dM_{GPCS}(t_0)/dt = J_{GM}(t_0) = M_{0G}(t=t_0)/\tau_G.$

Method for Measuring Blood Pressure in the Microcirculation System

Method of measuring the amount of water in tissue described above allows the determination of values of parameters characterizing the state of intercellular tissue and microcirculation of a local tissue site in a mode of continuous measurement in real time. In particular, method makes it possible to determine the values of osmotic pressure of the intercellular tissue and hydraulic pressure in the microcirculation system.

In addition, this method allows quantifying the values of the following parameters: the maximum pressure in the micro circulation system (pressure in the arterial end of the capillary), the minimum pressure in the micro circulation system (pressure in the venous end of the capillary), osmotic pressure of the intercellular substance (tissue pressure), colloid osmotic (oncotic) pressure of blood plasma, the magnitude of the trans-capillary flows (resulting, filtration and absorption), coefficient of filtration of the intercellular tissue, the water content in the intercellular tissue, the magnitude of the hydraulic resistance of the capillary vessels.

Method is based on measuring a parameter characterizing the state of a local tissue site with different values of the external pressure on the surface of the controlled area. For example, density of water flow through the SC, tissue pressure (osmotic pressure of the intercellular substance), amount of water in the intercellular substance act as such parameters characterizing the state of local tissue site.

Method of measuring the above parameters of microcirculation and intercellular tissue, based on measuring the density of water flow through the stratum corneum, involves the following stages:

1) measuring the density of water flow through the local section of the SC and climatic parameters (temperature and humidity of the ambient air, heat flow through the external envelope or air temperature behind the building envelope);

2) measure the dependence of water flow density through the stratum corneum on the external pressure exerted on the local controlled tissue site;

3) determine the microcirculation parameters of the local tissue site according to the nature and kinks, obtained according to item 2) of the dependence.

Another method is based on measuring the amount of water in the deep layer of human flesh. Method of measuring the above parameters of microcirculation and intercellular substance involves the following stages:

1) measure the amount of water in the intercellular substance in the continuous monitoring mode;

2) determine the dependence of the amount of water in the intercellular substance on the external pressure exerted on the controlled local tissue site;

3) determine the parameters of microcirculation and intercellular substance by the nature and kinks obtained according to item 2) of the dependence.

FIG. 19. shows a characteristic plot of the amount of water in the epidermis versus the magnitude of external pressure. Values of the external pressure at which characteristic kinks are detected correspond to the minimum and maximum pressure in the microcirculation system. The average pressure value, determined by the maximum and minimum pressures, is equal to the average value of the capillary pressure. Slope of linear dependence at the initial and final sections allows us to determine the filtration coefficient of the intercellular tissue for water. The point of intersection of the final linear section with the pressure axis corresponds to the difference between osmotic pressure of the intercellular tissue and colloid-osmotic (oncotic) pressure of blood plasma.

The possibilities for measuring various parameters of microcirculation of a local tissue site, in particular the possibility of measuring the amount of water in the stratum corneum and in intercellular space of the skin, and possibility of measuring the coefficients of filtration of the intercellular tissue for water, allow adaptation of this method in cosmetology to assess the effectiveness of cosmetic creams, as well as in dermatology for diagnostics of pathological conditions of the skin (in particular, for diagnosis and monitoring of psoriasis).

Method for Measuring the Osmotic Pressure of the Intercellular Substance

FIG. 19. shows the dependence of the amount of water in the intercellular tissue on external pressure. Point of intersection of the initial section of this dependence with the abscissa axis (the value of the external pressure on tissue surface, in mm of mercury) determines the amount of excess hydraulic pressure (the driving force of the volumetric flow of water through the epidermis). Relationship shown in FIG. 19 also makes it possible to determine the absolute value of the osmotic pressure of the intercellular substance in its native state.

FIG. 12. shows the dependence of the amount of water in intercellular tissue on the magnitude of the external heat flux incident on the surface of the local body region. Point of intersection of the initial section of this dependence with X (abscise) axis (density of the external heat flux directed to the surface of the body, in power units—$mW/cm^2$) determines the absolute value of the water flux density through the stratum corneum or power of evaporative cooling process. Dependence, shown in FIG. 12 also makes it possible to determine the absolute value of the excess amount of water $M-M_0$ (where $M_0$ is the amount of water in the intercellular substance at the osmotic pressure equal to zero) or the amount of water that determines the intercellular substance swelling in its native state.

The absolute value of the density of water flow through the epidermis, determined from the graph shown in FIG. 12, and the absolute value of driving force of the volumetric water flow, determined from the graph in FIG. 19, allow to get the value of filtration coefficient of intercellular tissue for water.

The described method of measurement allows both—to determine the absolute value of water in the intercellular tissue, and to normalize this physiological parameter according to climatic parameters and blood sugar level. Possibility of such a normalization let us to determine the deviations of measured physiological parameter characterizing the state of the intercellular substance from the norm.

Method for measuring excess water (quantity of water in the intercellular substance that determines the swelling of intercellular substance in its native state) involves the following stages:

1) measure the amount of water in the intercellular substance by the previously described methods;

2) measure the dependence of quantity of water in the intercellular substance on the external heat flux (and/or external pressure) and to determine the amount of excess water (the amount of water, which initiates swelling of the intercellular tissue in its native state);

3) measure blood sugar and climatic parameters;

4) normalize the obtained value of the amount of water in the intercellular substance to the sugar content in the blood in the norm (5 mmol/L), considering the climatic parameters.

5) determine deviation of the amount of water in intercellular tissue from its normal amount.

The described method allows to determine changes in the state of the intercellular substance by measuring the amount of water in the intercellular tissue and comparing the obtained value with the norm value.

Determination of the Physiological Norm

In the section "Physics of intercellular substance", it was shown that the self-organization of transfer processes of heat and matter (mutually agreed functioning of the microcirculation and cell metabolism) of the local area of the living tissue is due to the peculiarities of the physical properties of the intercellular substance, due to the peculiarities of the thermodynamic behavior of the intercellular substance under normal physiological conditions.

As it was shown, the negative physiological state of living tissue can be realized only in the three-phase region of thermal function, in which all three phases of the intercellular substance (tangle, liquid phase, globule) are in thermodynamic equilibrium. The normal physiological temperature and normal atmospheric pressure, at which the physiological state of living tissue is realized, correspond to the triple point of intercellular substance, in which the thermodynamic equilibrium between all three phases of intercellular substance is realized.

In the section "Osmotic pressure of intercellular substance" the method of practical measurement of parameters characterizing the physical phase state of intercellular substance is considered above. Such parameters, which characterize the thermodynamic phase state of the intercellular substance, are osmotic pressure and water content, which determines the swelling of the intercellular substance in its native state.

In practice, the measurement of the absolute value of the amount of water in the intercellular substance allows to determine the physical state of the intercellular substance, which determines the physiological state of the local area of living tissue. The deviation of the physical phase state of intercellular substance from the norm leads to deviations of the physiological state of living tissue from the norm.

The physiological norm can be defined as follows. The physiological state of the local area of the living tissue corresponds to the physiological norm, in that case, if the intercellular substance is in a three-phase equilibrium with the coexistence of all three phases of intercellular substance (tangle, liquid phase, globule).

The amount of water that determines the swelling of the intercellular substance, and the magnitude of the driving force of the intercellular micro fluidics are indicators that are sensitive to various external influences and diseases. The described method allows to quantify with high accuracy deviations from the norm of the thermodynamic state of the intercellular substance of the local tissue area, and as a consequence, to determine deviations from the norm of the physiological state of the local area of living tissue. Another way to diagnose the physiological state of living tissue: deviations of the physiological state of living tissue from the physiological norm can be determined by measuring the parameters of microcirculation (maximum and minimum pressure in the microcirculation, filtration coefficient) using the method described in the method of measuring blood pressure in the microcirculation.

Another way to diagnose the physiological state of living tissue: deviations of the physiological state of living tissue from the physiological norm can be determined by measuring the parameters of microcirculation (maximum and minimum pressure in the microcirculation system, filtration coefficient) using the method described in the method of measuring blood pressure in the microcirculation. The physiological state of living tissue corresponds to the norm, if the parameters of microcirculation correspond to the norm.

In particular, the method can be used in cosmetology to assess the effectiveness of the impact of cosmetic creams, as well as in dermatology for the diagnosis of pathological conditions of the skin (in particular, for the diagnosis and monitoring of psoriasis).

Method for Managing a Tissue Fluid Transport and Lymph Drainage.

Method for managing a tissue fluid transport is based on the possibility of changing a volume flow of the tissue fluid circulating in the intercellular space by affecting the intercellular substance with weak effects of physical and chemical nature. External pressure, heat flow, a constant magnetic field, direct electric current and others relate to the external physical effects using which managing the tissue liquid transport is possible.

In FIGS. 12, 19 are presented the experimental study results of the effects of different physical factors on a local tissue—external thermal flux and external pressure. The experimental results presented in these figures prove the possibility of changing a local water content in the intercellular substance using physical effects of a weak intensity and they thereby prove the possibility of efficient managing the tissue fluid transport using external physical and chemical effects.

By changing external pressure (FIG. 19), one can change swelling degree of the intercellular substance (water content in the intercellular substance) and, as a sequence, the tissue fluid volume flow in the intercellular substance and in the capillary vascular system. An excessive external pressure on a local body surface leads to swelling the intercellular substance and a local decompression (vacuum), on the contrary, results in compression of the intercellular substance. In such method of compressing the intercellular substance, there occur increase in capillary vascular lumen and increase in the lumen of the channels through which the tissue fluid circulates. Such local effect results in a raised volume flow rate through the capillary vessels and a volume flow of the tissue fluid circulating in the intercellular substance. In the experiments with the effect of local decompression it was found that local reduction of pressure, relative to atmospheric, has the effect of reducing the water content in the intercellular substance caused by the effect of compression of the intercellular substance. A local pressure lowering relative to atmospheric pressure is seen to lead to the effect of a diminished water content in the intercellular substance caused by the effect of the intercellular substance compression effect. A local decompression in these experiments was affected, using the local decompression apparatus Alodec—4ak. The body surface is locally affected using a special vacuum applicator (a specific "cup") inside which a dosed decompression regimen is maintained.

Such method of a local pulsing effect on a tissue results in periodic pulsations of osmotic and elastic pressure of the intercellular substance as well as hydraulic pressure in the capillary vascular system in a tissue volume under the vacuum applicator. Such effect leads to volume pulsations of the intercellular substance characterized by the occurrence of pulsating liquid flows circulating in the system: "the blood circulation capillaries—the intercellular space—the lymphatic drainage system". Such method using an external effect provides for managing a tissue liquid transport and lymphatic drainage of a local tissue site.

A physiotherapeutic effect of such exposure becomes clear if one takes into consideration that a volume flow of the tissue fluid provides for delivery of nutrients and oxygen to tissue cells and draining products of cellular metabolism into the blood circulation system and the lymphatic system. This process initiated by an external effect results in beginning an efficient supply of a tissue with sugars, nutrients and oxygen. As a natural sequence, the processes of cellular metabolism and general metabolism are accelerated: metabolism rate of tissue cells is growing that is a stimulating growth factor of cells and regeneration of tissues.

A smooth regulation of a vacuum degree in the applicator allows for regulating and establishing a tissue layer depth wherein the drainage effect stimulated by an external effect is caused. The drainage effect "X" is interrelated with the negative pressure "P" by the following equation:

$P=F(P_0,X,L_0)$ where $P_0$ is a tissue pressure.

$L_0$ is a thickness (depth) of a tissue volume under the applicator.

A value of a tissue pressure $P_0$ can be determined by measuring water amount in the intercellular substance or blood pressure. A thickness (depth) of a tissue volume under the applicator can be determined by measuring a circle perimeter of the controlled body site.

A smooth regulation of the rate and porosity of pneumo pulses allows for regulation and establishment of a volume flow value of tissue fluid and lymph drainage.

A similar effect is achievable by change in external temperature or cooling (heating). A local cooling of the body surface causes contraction of the intercellular substance and heating a tissue leads to swelling thereof. FIGS. 19 and 20 present the experimental results on studying the effect of external heat flows on the intercellular substance state. A local effect of heat flow on the body surface is seen to result in increased water content in the intercellular substance of a local site caused by swelling the intercellular substance. On the contrary, a local cooling the body surface reads to diminishing water content in the intercellular substance resulting from contraction of the intercellular substance.

The effects of contraction and swelling a tissue can be stimulated also using a weak direct electric current and a constant magnetic field. A mechanical equilibrium of the system "the intercellular substance—a capillary" which determines water content in the intercellular substance proved to be also sensitive to weak constant electric and magnetic fields.

The mechanism of such sensitivity becomes clear if one takes into consideration that a constant electric field (constant electric current) leads to the appearance of electro-kinetic phenomena in the epidermis of living tissue, in particular the phenomenon of electro-osmosis, due to a change in the equilibrium distribution of electrical ions of tissue fluid in the tissue volume, that in its turn results in disorder of the system of mechanical equilibrium and in change in water content in the intercellular space. Electric current directed from inside toward the skin surface results in the effect of swelling the intercellular substance. On the contrary, change in direction of electric current results in a contraction effect of the intercellular substance.

The mechanism of sensitivity to a constant magnetic field is based on the fact that transfer of charged ions in a tissue volume effected by flows of intercellular fluid and a constant magnetic field leads to redistribution of these flows and to disorder of the system's mechanical equilibrium.

Thus, method for managing a tissue fluid transport and lymph drainage is based on the effect on a tissue using different physical factors, which cause reversible changes in water content in the intercellular space. To the number of the physical factors using which managing a tissue fluid transport is possible relate the following: a local superficial cooling (heating) or a thermal electromagnetic radiation; local decompression and excessive pressure; direct electric current and a constant magnetic field; acoustic fluctuations (a law frequency vibration, ultrasound etc.) and other factors.

Local effects of a low intensity as a rule lead to the effects described above. Typical powers and values of physical effects are as follows: electromagnetic radiations 0-20 $mW/cm^2$; local decompression values 0-100 mm Hg; direct electric current values 0-100 nA; values of a constant magnetic field intensity 0-50 milli tesla.

Method for managing a tissue fluid transport described above may be used in treating different diseases. Different diseases may lead to different typical changes in the intercellular substance state.

Diseases accompanied by swelling the intercellular substance state exceeding the norm (the "tissue edema" state) may be treated and prevented using the effects which cause a local contraction of the intercellular substance (a local decompression, cooling).

Diseases accompanied by a lowered water content in the intercellular substance may be treated and prevented using the effects which cause a local a local increase in swelling degree of the intercellular substance (a local compression, heating). The method for managing a tissue fluid transport stipulates the following steps:
1) measuring water content in the intercellular substance of a local tissue site;
2) determining the intercellular substance state by water content in the intercellular substance;
3) determining a method of external effect and regimen of the effect by the state of the intercellular substance;
4) external effecting;
5) controlling efficacy of exposure by measuring water content in the intercellular substance.

To the number of such diseases which can be efficiently treated using the instant method relate the following:
vertebral diseases, in particular osteochondrosis;
sexual disorders, in particular erectile dysfunction; articular diseases;
the disease known as "the orange skin disease" and other diseases;
diseases of internal organs.

Method allows for stimulating cellular growth of the breast tissue, it leads to increase in elasticity of the facial tissue and other body parts.

Method for managing a tissue fluid transport given consideration above is also applicable for treating and preventing type 2 diabetes.

Method for Diagnostics of Cardiovascular Disorders.

In the section "Physics of intercellular substance" the physical characteristics of the intercellular substance and the mechanisms determining an unequivocal relationship between a biochemical composition of the blood and climatic parameters, have been given a detailed consideration.

In particular, a distribution of the intravascular hydraulic pressure in fixed values of climatic parameters was shown to be unequivocally determined by blood sugar concentration.

In a general case, hydraulic pressure in the blood circulation system is lineally proportionally dependent on blood sugar level and climatic parameters. In practice, by measuring climatic parameters and blood sugar concentration, one can unequivocally determine through calculation a hydraulic pressure in different parts of the circulation system.

For example, at blood sugar concentration equal to 4.5 mM/L, pressure distribution in the circulation system is characterized by the following values (in mm Hg):

a mean blood pressure is 100, pressure at a capillary arterial end is 54, a mean capillary pressure is 25, pressure at a capillary venous end is 7.

Method allows for determining the following parameters of the cardio-vascular system by measuring climatic parameters and blood sugar level: typical hydraulic pressure values in the circulation system; arterial, venous and capillary hydraulic resistance; values of trans-capillary flows (a resulting, filtration and absorption ones); heart rate and power of cardiac contractions. Under normal conditions at fixed climatic parameters, changes in blood sugar level lead to lineally proportional changes in the blood circulation system pressure. The other parameters characterizing a state of the cardiovascular system, are also functions of blood sugar level.

Method for diagnosing cardiovascular disorders stipulates the following steps:

1) measuring air temperature and blood sugar level;

2) determining by calculation a value of a controllable parameter characterizing the cardiovascular system by values of air temperature and blood sugar level using the technique described in the section "Biophysical fundamentals: physics of the intercellular substance". As such parameter, hydraulic pressure in the circulation system may be for example chosen;

3) determining by measurement a value of a controllable parameter characterizing the cardiovascular system; 4) determining a deviation of a value of a controllable parameter obtained be measurement, from a value thereof determined by calculation by measurements of blood sugar level and air temperature and determining a character and a reason of deviation of the parameter from the norm.

The technique allows for determining parameters of the cardiovascular system by the known values of climatic parameters and blood sugar level. The following ones belong to a number of such parameters: a mean capillary pressure; pressure at venous and arterial capillary end; arterial, venous and capillary hydraulic resistance; a resulting trans-capillary flow.

A deviation of the parameters' values obtained by direct measurement from these parameters determined by measuring temperature and blood sugar level ("the norm") is a direct indication to pathological disorders in the cardiovascular system. In particular, the described method for diagnosis allows for diagnosing pathological conditions of the cardiovascular system, which are characterized by elevated blood pressure (hypertension) and conditions, which are characterized by a lowered blood pressure (hypotension).

Thus, deviations of a pressure value in the cardiovascular system from the pressure, which is determined by calculation originating from the values of blood sugar level and climatic parameters allows for diagnosing disorders of the cardiovascular system, in particular, determining states with elevated and lowered pressure.

Method for Diagnostics of Cardiovascular Disorders: Monitoring Condition of the Cardiovascular System in Patient with Diabetes.

The method for diagnostics described in the previous section "Method for diagnostics of cardiovascular disorders" allows for performing diagnostic monitoring of the blood circulation system's condition in patients with diabetes. Diabetic condition is known to be accompanied by disorders of the cardiovascular system. In diabetes, the both peripheral and central blood circulation systems are known to be subjected to pathological changes.

Elevated blood sugar level is a cause of pathological changes occurring in the blood circulation system. Elevated blood sugar level leads to elevated values of pressure in the blood circulation system. The biophysical mechanism determining an unequivocal relationship between pressure in the microcirculation system and blood sugar level has been given a detailed consideration in the section "Physics of the intercellular substance". A prolonged maintenance of an elevated pressure exceeding the norm in the blood circulation system is accompanied by an increased load on cardiac and vascular work and as a sequence, it leads to the development of pathological cardiovascular disorders.

For the indicated reason, monitoring the condition of circulation in diabetic patients is by now an actual and burning task. Such monitoring will allow patients with diabetes to timely correct therapy and to avoid the development of chronic cardiovascular diseases, which are currently the main cause of lethal outcomes in patients with diabetes. In particular, the described method allows for early diagnosis and monitoring the disease known as "a diabetic foot".

Method for Diagnostics of a Functional (Physiological) State of a Local Living Tissue Site.

In the section "Physics of the intercellular substance" distribution of hydrostatic pressure in the microcirculation system as well as distribution of osmotic pressure of the intercellular substance in a tissue volume between blood capillaries are shown to be determined by a thermodynamics phase state of the intercellular substance. On the other hand, a physical state of the intercellular substance is an unequivocal function of biochemical blood composition and climatic parameters. Synchronization of volume flows of a substance and heat are effected due to specific physical characteristics of the intercellular substance. Intensity of a substance and heat flows such as flows of a tissue liquid, glucose and other dissolved substances and heat transfer flow to the body surface are equivocal functions of a phase state of the intercellular substance.

Change in physical characteristics of the intercellular substance of a tissue local site resulting from the development of pathological disorders of different nature, leads to disorders and deviations of a mutually adjusted (synchronous) functioning of the system: a blood capillary—the intercellular substance—a tissue cell.

The method for measuring the parameters characterizing a physical state of the intercellular substance described in the section "Method for measuring osmotic pressure of the intercellular substance" opens principally new possibilities for diagnosing a functional (physiological) state of a local live tissue site. The method for diagnostics stipulates the following steps:

1) measuring a value of a parameter characterizing a state of the intercellular substance, for example, water amount in the intercellular substance, osmotic pressure or a resulting trans-capillary flow;

2) measuring air temperature and blood sugar level;

3) determining a calculated value of a parameter characterizing a state of the intercellular substance;

4) determining a deviation of a value of a parameter obtained be measurement, from a value thereof determined by calculation by measurements of air temperature and blood sugar level;

5) determining by the deviation value (section 4) a character of the deviation and a degree of a pathological state of a local site intercellular substance.

Another method for diagnosing a functional sate of a local tissue level is based on an on-line recording a dynamic reaction of a parameter characterizing a state of the intercellular substance in response to a weak external effect. Hereinafter, under a dynamic reaction a time course of change in a parameter characterizing a tissue state in response to an external effect is meant. Effects of different nature (physical, physiological or chemical) belong to the effect leading to change in a state of the intercellular substance. For example, external heat flow, external pressure etc. belong to external physical effects.

By changing external temperature or heating (cooling) the body surface, one can change swelling degree of the intercellular substance or water amount in the intercellular space. Similar effect can be achieved due to change in external pressure relative atmospheric pressure. A local decompression (vacuum) causes compression of the intercellular substance and an excessive pressure, on the contrary, leads to swelling thereof.

The effects described above are a sequence of physical characteristics of the intercellular substance. For this reason, by value and character of a dynamic reaction of the parameter characterizing a state of the intercellular substance, one can determine possible deviations of the intercellular substance properties from the norm and to diagnose a physiological state of a tissue local site. For example, a local thermal effect of electromagnetic radiation (infrared or optic) on the body surface leads in a real time to a typical local reaction of the parameters characterizing a state of the intercellular substance of a local controllable site. In such effect, osmotic pressure of the intercellular substance changes that results in rise in hydraulic pressure in the microcirculation system and as a sequence, elevation of a resulting trans-capillary flow and water flow density through a local site of the ECL occurs. A typical specificity of a reaction corresponding to a physiological norm in response to an external thermal effect is that change in steam cooling power determinable by change in water flow density through the ECL, appears to be exactly equal to a heat effect power. A thermal effect with the power 1 mW/cm$^2$ leads to increase in a resulting trans-capillary flow value and water flow density through the ECL (determining intensity of a steam cooling process), which increase is equivalent to rise in steam cooling intensity by 1 mW/cm$^2$. A typical time constant of forming such reaction is several seconds. Change in the intercellular substance properties occurring as a result of disorders and pathologies of different nature, leads to change in a typical reaction in response to a weak effect of a physical nature. The typical experimental results on studying the effect of heat flows on a state of the intercellular substance are presented in FIGS. 18 and 19.

Method for diagnostics supposes the following steps:

1) a real-time measuring a value of the parameter characterizing a state of the intercellular substance (for example, water amount in the intercellular substance);

2) a local dosed effect on a tissue using physical factors of a weak intensity (examples of physical factors: an external thermal effect, external pressure, a direct electric current and a constant magnetic field);

3) a real-time measurement of a dynamic reaction of a recorded parameter in response to an external effect (for example, a heat flow) and determining water flow density value through the epidermis;

4) determining a physiological state deviation of a local tissue site from the norm and diagnosing a functional state by water flow density value through the epidermis and by a dynamic reaction character (intensity of reaction, time delay, time course character).

Another possibility of a functional diagnosis of a local tissue site is described in the section "Method for measuring osmotic pressure of the intercellular substance" and it is based on measuring relationship between water amount in the intercellular substance and an external effect.

5) Measuring water amount in the intercellular substance depending on external thermal effect (FIG. 19) allows for determining the amount of water, which determines swelling the intercellular substance. The described method allows for not only determining water amount in the intercellular substance, but also normalizing this parameter by air temperature and blood sugar level. The possibility of such normalization allows for determining deviation from the norm of the measurable parameter characterizing the state of the intercellular substance.

In a similar way, the intercellular substance state is diagnosed using effects (physical and physiological) of a different nature. To the number of such physical effects also relate an external pressure, a local decompression, a direct electric current, a constant magnetic field and others. Examples of physiological effects are a sugar test and different medicaments exerting effect on the intercellular substance characteristics.

Method for measuring water amount in the intercellular substance determining swelling the intercellular substance, supposes the following steps:

6) measuring water amount in the intercellular substance using the methods described above;

7) measuring relationship between water amount in the intercellular substance and an external heat flow (or an external pressure) and measuring water amount determining swelling the intercellular substance;

8) measuring blood sugar level and air temperature;

9) normalizing the obtained water amount value in the intercellular substance to a room temperature (20° C.) and the normal blood sugar level (5 mmol/L);

10) determining a deviation of water amount value in the intercellular substance from the normal amount thereof.

The described method allows for determining changes in the intercellular substance state by measuring water amount in the intercellular substance and comparing the obtained value with the normal values.

Method for measuring an excessive water amount (or the water amount determining swelling the intercellular substance) admits a simple qualitative determination of the physiological state of a local tissue site through the notion of the intercellular substance physical sate.

Determination of the physiological norm is given consideration in the section "Determining the physiological norm". The physiological state of the local area of living tissue corresponds to the physiological norm if the thermodynamic (physical) state of the intercellular substance corresponds to the three-phase state in which all three phases of the intercellular substance (tangle, liquid phase, globule) coexist.

The excessive water amount determining swelling the intercellular substance and the value of the volume flow moving force ate indicator that is sensitive to different external effects and diseases. The described method allows for quantitatively determining deviations from the norm with a high accuracy of the physiological sate of the intercellular substance of a local tissue site.

Methods of diagnostics described above, may be used for early diagnosing different diseases the development of which is accompanied by a change in the intercellular substance characteristics. The following diseases relate to such diseases:

malignant tumors the development of which is accompanied by the typical changes in localized tissue sites;

the disease known as "an orange skin" and the development of which is accompanied by the typical changes in the skin and the subcutaneous cellular tissue:

different stages of obesity;

type 1 and 2 diabetes accompanied by the typical changes in the intercellular substance characteristics (for example, tissue sensitivity to insulin) and microcirculation;

some cardiovascular diseases the development of which is accompanied by the typical changes in the intercellular substance and many other diseases.

Furthermore, the described method of diagnosing pathological states of the intercellular substance may be used in cosmetology and esthetic medicine to assess a functional state of the skin as well as to visualize and to assess the effect on the skin of different cosmetic creams and medicaments. To embody "Method for diagnosing a functional (physiological) state of a local tissue site" described in the present section, a device for measuring water amount in the intercellular substance is used. For measuring water amount in the intercellular substance the accuracy of which exceeds 1%, is described above. This method can be individually used in practice for example, to measure a local humid content in the skin tissue to assess the effect of cosmetic creams.

Method for Determining a Tissue Sensitivity to Insulin. Diagnostics of Prediabetic State.

Figure 16:
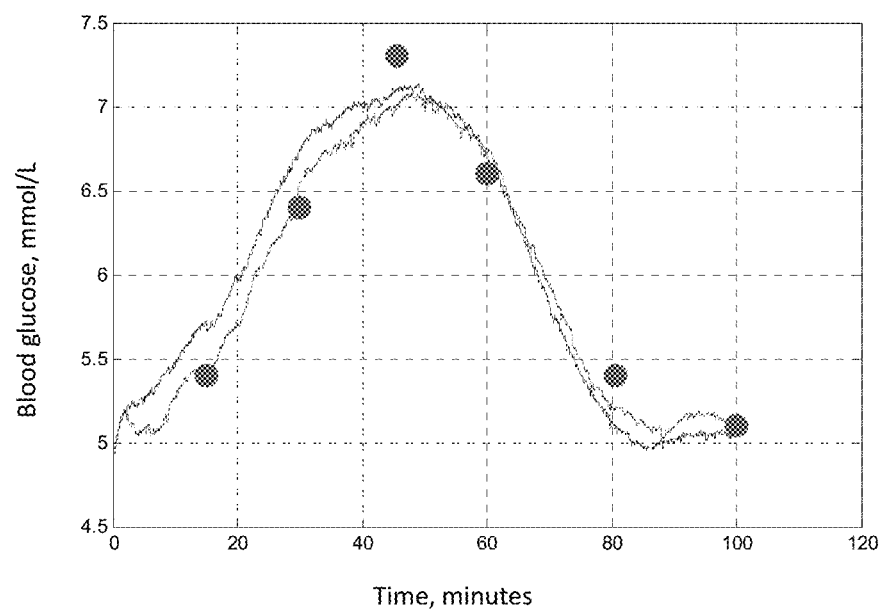
FIG. 16. Monitoring blood sugar of a healthy patient (58 years, male) during the day. Temporal dynamics of blood sugar in the morning on an empty stomach. Temporal dynamics of blood sugar level in a practically healthy patient (55 years old, male) in the process of sugar loading (sugar curve), recorded by a two-channel non-invasive microcalorimeter. Y axis contains values of the microcalorimeter signal in of mmol/liter units; X axis is the time in minutes. Sugar test (200 ml of 5% glucose solution) is taken by the patient on the 16th minute of the experiment. The results of invasive measurements, performed with the certified industrial meter "Accu-Chek active" of Roche-Diagnostics, are shown on the graph by circles. Absolute values of invasive measurements in units of mmol/liter are 5.4 (15 minutes), respectively; 6.4 (30 minutes); 7.3 (46 minutes); 6.6 (60 minutes); 5.4 (80 minutes) and 5.1 (100 minutes). The air temperature in the room is 22.0 C.
Figure 17A:
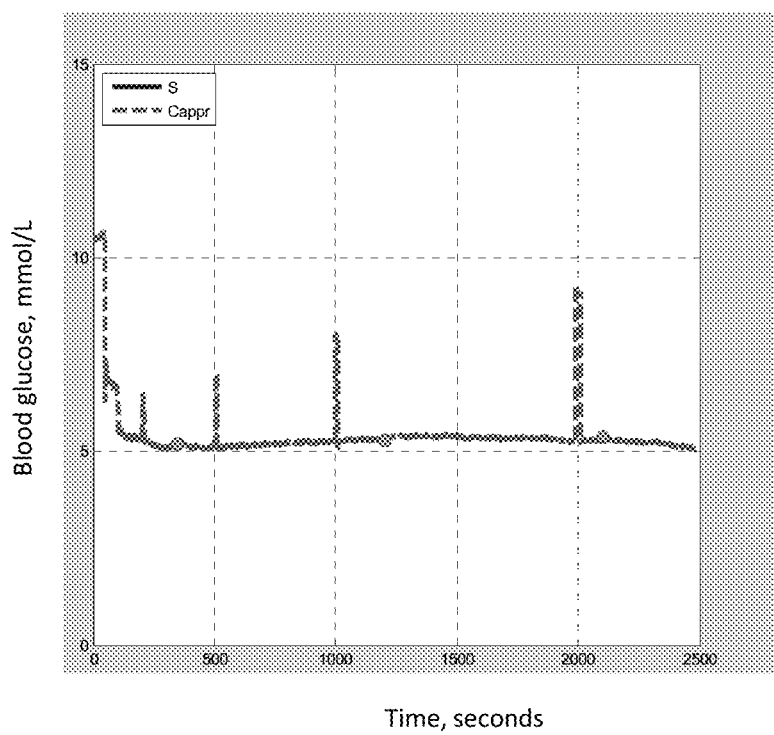
FIG. 17 (a). Monitoring blood sugar of a healthy patient (58 years, male) during the day. Temporal dynamics of blood sugar in the morning on an empty stomach.
Figure 17B:
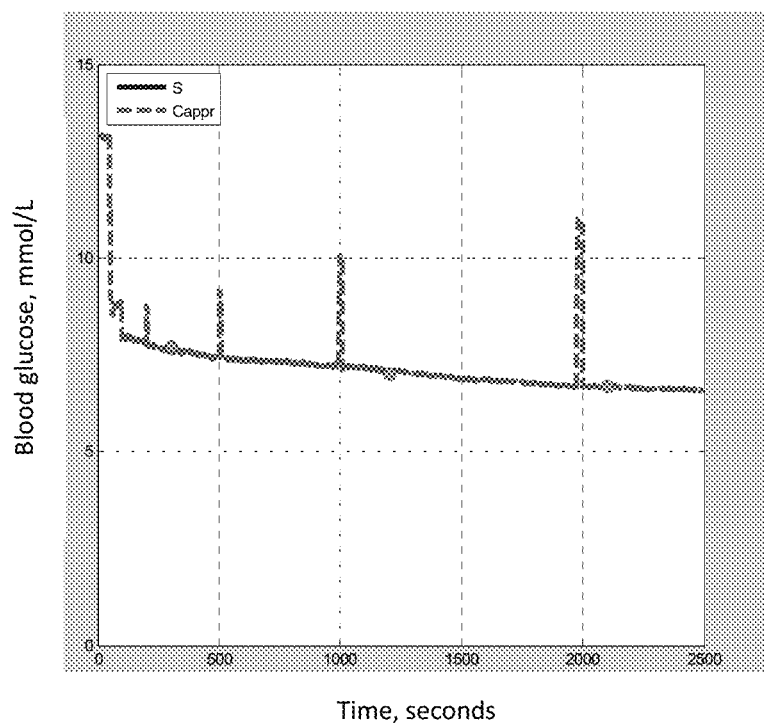
Figure 17C:
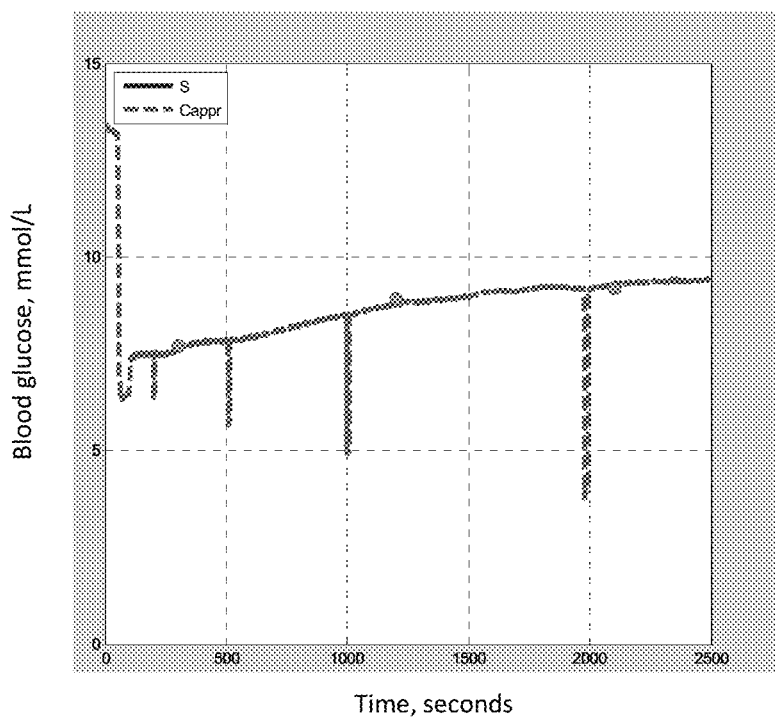
Figure 17D:
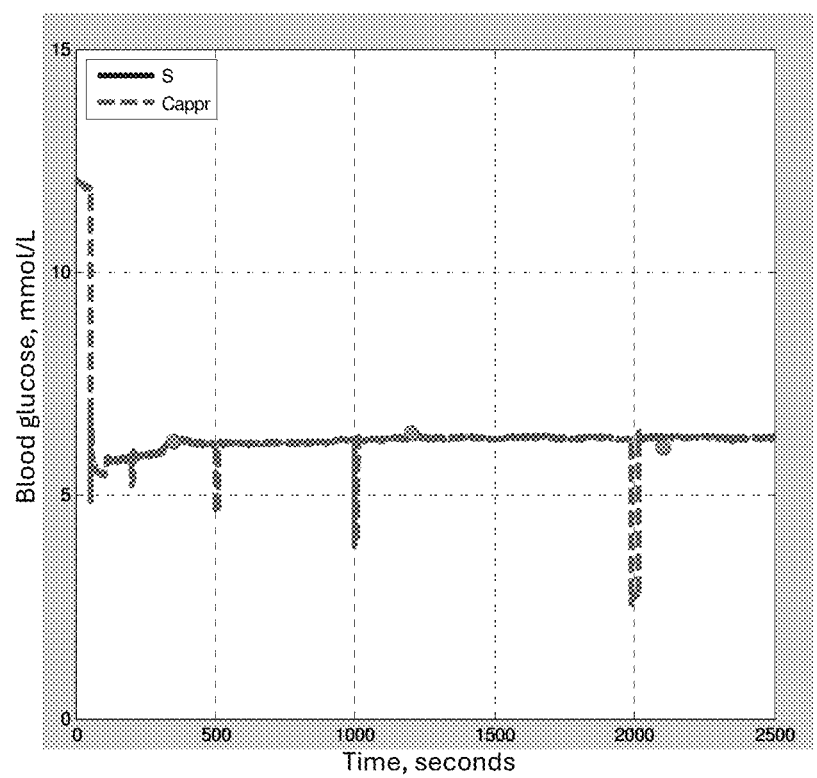

Method for measuring blood sugar level described above allows for determining blood sugar level time dynamics by monitoring osmotic pressure or water content of the intercellular substance of a local tissue and climatic parameters. The given method allows for conducting recording blood sugar level in a continuous monitoring regimen (one measurement every 1 to 10 seconds). FIG. 16 shows the results of the continuous monitoring blood sugar level under the conditions of conducting the standard glucose tolerance test ("a continuous sugar curve"). For comparison, the modem manuals determine as "a sugar curve" several measurements (as a rule, 3 to 4) performed by finger prick measurements with an interval between measurements of about 30 minutes. The experimental results presented in FIG. 16, were obtained using the pilot device experimental which is presented in FIG. 15. The noninvasive real time intercellular osmotic pressure monitoring technique based on monitoring of a local parameter, characterizing the intercellular substance state of a local tissue, opens novel opportunities for early diagnoses of pre-diabetic state and insulin resistance of local living tissue.

Disorder of Glucose Tolerance.

Modern manuals on medicine determine disorder of glucose tolerance (DGT) as blood glucose concentrations during the oral glucose tolerance test lying in the interval between normal and diabetic values (which are between 7.8 and 11.0 mmol/L in 2 hours after administering 75 g glucose). DGT may probably be given consideration as to a pre-diabetic state, while not all subjects with DGT develop diabetes. In USA every tenth adult individual has DGT the rate thereof increasing with age achieving every fourth among persons aged from 65 to 74 years. The epidemiological studies carried out in different countries indicate to a close relation between DGT and obesity. For example, the study carried out in the USA, has found that a mean EBW (excessive body weight) in persons, who consequently developed DGT, was significantly higher than in individuals with a normal EBW. The study carried out in Israel has established that a history of a high EBW was accompanied by a raised frequency of DGT development over a 10-year period.

Method for monitoring of osmotic pressure of intercellular substance described above, allows for determining DGT in a continuous monitoring regimen with a higher accuracy. In particular, the method is efficient for determining type 2 pre-diabetic state.

Method for Determining a Tissue Sensitivity to Insulin.

Method of continuous registration of the time dynamics of the rate of local tissue metabolism (rate of absorption of glucose by the local tissue site), described above, allows to determine the sensitivity of tissue to insulin by the characteristics of the time dynamics of the living tissue metabolism rate. Method is based on continuous recording of the time dynamics (monitoring) of the tissue metabolism rate.

The osmotic pressure (or water content) of the intercellular substance of the local tissue is continuously measured and changes in time dynamics as a result of external influences leading to characteristic changes in tissue sensitivity to insulin are recorded. As is known, the impact of some external factors, physiological and physical, on the tissue leads to reversible changes in tissue sensitivity to insulin. These factors include, in particular, muscle load and temperature effects [2]. To external effects, which cause reversible changes in tissue sensitivity to insulin, belong the effects which lead to reversible changes in a phase state of the intercellular substance. The external physical parameters, which determine a phase state of the intercellular substance, have been given consideration in the section "Physics of intercellular substance".

To the number of such external physical factors belong the following: an external pressure; a local decompression; an external temperature; electromagnetic radiation causing volume heating of a tissue; a weak direct electric current; a constant magnetic field; a local muscular load to a tissue and others.

Method for determining tissue sensitivity to insulin supposes the following steps.

1) measuring a local tissue metabolism (sugar absorption rate by a tissue) in a continuous monitoring regimen during a standard sugar load (oral administration of 75 g glucose) by monitoring osmotic pressure (or water content) of the intercellular substance and climatic parameters;

2) exerting external physical effect that causes a reversible change in tissue sensitivity to insulin on a controllable local tissue site;

3) determining tissue sensitivity to insulin by the characteristics of a local metabolism time dynamics.

In tests with muscular load, it was found that the load leads to characteristic changes in time dynamics: reduction in the recorded parameter occurs and growth thereof after a typical time interval equal to 1 to 2 minutes begins. Such character of water content changes in the intercellular substance is associated with the typical blood sugar level changes under the muscular load conditions. Reduction in the intercellular substance water content after beginning the load, is caused by reduction in local blood sugar and the intercellular fluid content. Dropping the intercellular fluid sugar level at the initial section of the temporal dynamics line is associated with rise in a local tissue sensitivity in response to muscular load. A subsequent rise in the intercellular substance water content leading to increase in water content in the ECL is caused by sugar content rise in the tissue fluid resulting from glycogen cleavage comprised in muscular cells.

Method for Diagnosing a Pathological State of Internal Organs.

The method for diagnosing consists in a real-time recording spatial-temporal distribution of a parameter characterizing the intercellular substance state of a local superficial site. The parameters characterizing the intercellular substance state of a local superficial site are for example osmotic pressure of the intercellular substance, water content in the intercellular substance, a value of a resulting trans-capillary water flow.

A spatial-temporal distribution is recorded using a multi-channel system the sensors of which are positioned on the controllable body site surface or using a scanning system.

The possibility of diagnosing the state of internal organs by measuring water content in the intercellular substance of the body superficial layer is based on the intercellular substance characteristics and peculiarities of a non-diffuse heat transfer mechanism from depth to surface. The intercellular substance characteristics and the heat transfer mechanism have been given consideration in the sections "Physics of intercellular substance".

Under normal physiologic conditions, temperature of an internal organ (37° C.) is as a rule higher than temperature of superficial tissues (30° C.). Such temperature difference leads to difference in osmotic pressure values of the intercellular substance and hydraulic pressure in the intercellular substance "channels" by which tissue fluid is transported. Tissue fluid is transported from depth to surface resulting from difference of hydraulic pressure. This process provides for heat transfer generated as a result of cellular metabolism from depth to surface and simultaneously maintains a steam cooling process (a non-perceived perspiration).

The development of an internal organ pathological state is accompanied by change in the intercellular substance state of this organ. For example, in case when a chronic disease of an internal organ is characterized by a lowered level of organ metabolism, osmotic pressure of the intercellular substance and pressure in the microcirculation system are also lowered. Tissue fluid circulation rate toward the surface is accordingly lowered. Eventually, this process results in the appearance a spatial non-uniformity of water content in the intercellular substance and rate and density of water flow through the ECL.

Thus, spatial-temporal mapping of water content in the intercellular substance allows for diagnosing pathological state of internal organs and determining a deviation of organic metabolism from the norm.

Method for diagnosing stipulates the following steps:
1) recording spatial-temporal distribution of water content in the intercellular substance;
2) localizing a problem site by a character of spatial-temporal distribution non-uniformity;
3) determining a differential drop value by measurements of water content in the intercellular substance in the following two points (sites, zones) of the body surface: one directly coinciding with the spatial non-uniformity region and another outside this region;
4) diagnosing by the differential drop in a controllable parameter value in the two surface points. Method for diagnosing may be also based on comparing values of the parameters obtained by direct measurements with their values obtained originating from blood sugar level measurements and air temperature. Such diagnosing stipulates the following additional steps:
5) measuring climatic parameters and blood sugar level;
6) determining a calculated value of the parameter characterizing the intercellular substance state;
7) determining a deviation of the parameter value obtained by measurements form the value of this parameter obtained by calculation (by the values of air temperature and blood sugar level);
8) determining character and degree of an internal organ's pathological state by the deviation value (section 7) of the controlled parameter.

Method of measurement described in the section "Method for determining osmotic pressure of the intercellular substance" allows for practical realization of "Method for diagnosing a pathological state of internal organs" described above, by the different method. Such method stipulates the following steps:
1) real-time recording a spatial-temporal distribution of water content in the intercellular substance;
2) localizing a problem site by a character of the spatial-temporal distribution and characteristics of water content in the intercellular substance over time;
3) measuring air temperature and blood sugar level;
4) determining by calculation using the measured values of temperature and blood sugar level, values of the microcirculation parameters and the intercellular substance;
5) measuring the parameters characterizing a state of a local tissue site using the method described in the section "Method for determining osmotic pressure of the intercellular substance".
6) diagnosing a state of an internal organ by deviations of values of the parameters obtained by measurements from the values of these parameters obtained by calculation.

Diagnosis using physiological tests and external effects is a variant of the method for diagnosing given consideration above. The method for diagnosing using external effects and physiological loads essentially do not differ from the method described in the section "Method for diagnosing a pathological state of the intercellular substance".

Physiological tests may be local and general. To the number of physiological tests relate thermal effect, external pressure, local decompression, electric current, local muscular load. An example of a general physiological load is for example a standard sugar load used in performing a glucose tolerance test.

Under the conditions of the mentioned physiological effect the typical reaction of a local metabolism of a superficial tissue site will as a rule be non-uniform in disorders of organ metabolism. A physiological load allows for visualizing internal body regions which are characterized by a disordered tissue metabolism.

Methods for diagnosing described above, allow for diagnosing a pathological state of internal organs as well as diagnosing diseases the development of which is accompanied by formation of local regions with modified tissue characteristics. To the number of such diseases relate malignant masses or cancer tumors. In particular, the method allows for detecting breast cancer at early stages of development thereof practically at any depth.

Method for Diagnosing Breast Cancer.

The process of formation and growth of breast cancer is known to be accompanied by typical physiological changes in tissue in the tumor location region as well as by changes in tissue in a superficial region determined by projection of the tumor region to the surface.

The following typical changes can relate to the number of physiological changes occurring in the region of cancer tumor localization:

Elevated level of glucose metabolism characterized by a raised rate of sugar absorption by cancer tissue recorded using a positron-emission tomography;

a high multiplication rate of cancer cells which is not typical for a normal tissue;

a typical tissue condensation recorded by X-ray methods;

typical changes in microcirculation recorded by optic methods.

Typical physiological changes occur also in superficial tissues localization of which is determined by a tumor region projection to the surface. To the number of such changes relate changes in microcirculation characterized by changes in surface temperature recorded using thermo-vision methods.

As cancer tumor grows, a gradual involvement of the surface tissue located over the tumor region inside the breast occurs. Malignant tumors have an elevated level of glucose metabolism and enhanced tissue sugar consumption and as a sequence, elevated level of heat production.

Among the known methods of breast cancer diagnoses a "gold standard" is an X-ray mammography which allows for detecting and determining localization of a cancer tumor with a high probability. However, the radiographic method does not allow for identification a cancer tumor and distinguishing a cancer tumor from a malignant tumor. In clinical practice, for these purposes a biopsy method is used which is expensive and painful.

Positron-emission tomography is a method, which allows for detection and identification of malignant neoplasms. Regions of cancer tissue which are characterized by an increased sugar absorption rate, are detected with a high spatial resolution using a positron-emission tomography (PET). However, a practical use of the PET for early diagnostics and screening breast cancer is limited, since the equipment is expensive.

Analysis and judging characteristic physiological changes occurring during the development of a cancer tumor which were carried bout based on comprehension of physical properties of the intercellular substance given consideration in the section "Physics of intercellular substance", allow for explaining the mechanism of the main changes occurring in the breast tissue affected by cancer.

In the breast tissue affected by cancer a local lowering tissue pressure and contraction of the intercellular substance in the tumor region occur. This process leads to a gradual tissue condensation in the tumor region. Contraction of the intercellular substance leads to increase in the lumen of capillary vessels and channels in the intercellular space along which tissue fluid circulates in the intercellular space and increase in volume flow of tissue fluid. As a result, increase in delivery rate of sugars to a cancer cell occurs. Sugar absorption by the cell and metabolism rate in a local tissue region increase. Such changes probably maintain multiplication process of cancer cells.

Typical changes in tissue also occur in the tissue volume located between the tumor region and projection thereof to the surface. Lowering osmotic pressure of the intercellular substance in the tumor region results in lowering (or leveling) osmotic pressure gradient of the intercellular substance in a direction from the tumor toward the surface. As a sequence, water transport through the epidermis and water content in the intercellular substance of superficial layers, in particular the skin and the ECL, significantly diminish. Reduced intensity of steam cooling with concurrent rise in glucose metabolism rate and heat production, leads to the tissue temperature elevation in the tumor region as well as to rise in a superficial region temperature determined by projection of the tumor region to the surface. Development and growth of the tumor is accompanied by a gradual contraction of the intercellular substance in the region between the tumor and projection thereof to the surface. This process leads to elastic strain occurrence in the direction from the body surface toward the tumor region, which results in a gradual inward traction of the tumor as it grows.

Methods of measurement described above open principally new possibilities for early diagnosis of breast cancer. These methods allow for performing diagnostics in the two possible practical modifications:

1) Additional diagnostics. In this variant the method is used as an additional method to the standard X-ray method;

2) Main diagnostics. In this variant the method is used as independent one on the other methods, individual method for diagnostics.

Method for early diagnosing breast cancer according to the variant "Additional diagnostics" supposes the following steps:

1) Detecting and localization of the tumor using the X-ray method;

2) measuring value of the parameter characterizing a state of the intercellular substance, for example, water amount in the intercellular substance, osmotic pressure or a resulting transcapillary flow. Measurement is performed in two points (sites, zones) of the body surface—one immediately coinciding with the tumor projection region to the surface and another outside this region;

3) performing diagnostics by a differential drop value of the parameter in the two surface points.

The method for diagnostics may be also based on comparing values of the parameters obtained by measurements with the values thereof obtained by calculation. Such diagnostics stipulates the following additional steps:

4) measuring air temperature and blood sugar level;

5) determining a calculated value of the parameter characterizing a state of the intercellular substance;

6) determining a values' deviation of the parameters obtained my measurements from values of these parameters obtained by calculation by the values of air temperature and blood sugar level;

7) determining a character and degree of a pathological sate of the local site's intercellular substance by typical deviations of the parameters' values.

Physiological changes occurring in a tissue during the development of cancer tumor lead also to a change in the character of dynamic reactions of the intercellular substance in response to different physiological effects. In particular, a reaction of the intercellular substance to the effect of weak thermal flows and external pressures is modified. A local tissue reaction in response to a sugar load is also modified. These features open additional possibilities for diagnosing breast cancer. Such diagnostics is based on recording a time course of the parameter characterizing a state of the intercellular substance under the conditions of various physiological effect and it stipulates the following additional or independent steps:

5) a real-time measuring a value of the parameter characterizing a state of the intercellular substance (for example, water amount in the intercellular substance);

6) a local dosed effect on a tissue using physical factors of a weak intensity (examples of physical factors are an external thermal effect, external pressure, a direct electric current and a constant magnetic field, a sugar load);

7) a real-time measurement of a dynamic reaction of a recorded parameter in response to an external effect (for example, to a heat flow effect);

8) diagnosing a pathological state (intensity of reaction, time delay, time dynamics character by a character of the dynamic reaction.

Method for early diagnostics of breast cancer according to the variant "the main diagnostics", unlike the variant "the additional diagnostics", instead of the step 1) stipulates the following step:

1) a real-time recording a spatial-temporal distribution of the parameter characterizing a state of the intercellular substance. The methods of dynamic mapping are described in the section "A method for diagnosing a pathological state of internal organs".

A real-time recording the parameter characterizing a state of the intercellular substance allows for localizing (at the first step) a region with modified tissue characteristics. Following a spatial localizing a problematic surface region, breast cancer is diagnosed using the subsequent steps described above.

Microcalorimeter technique described above allows to monitor with high accuracy heat generation of living tissue metabolism. The technique allows to detect small changes in tissue heat generation with accuracy 0,002 milli calories/sec·cm$^2$. High sensitivity and spatial detection ability of method allows using the technique in early diagnosis and prevention of cancer.

Method for Visualization of a Therapeutic Effect.

Methods for measuring a tissue local metabolism rate and micro circulation parameters of a local tissue site open principally new possibilities for visualizing therapeutic effects as well as allow for a real-time determining efficacy of therapeutic procedures.

Method for visualization of a therapeutic effect stipulates the following steps:

A therapeutic effect is exerted in the regiment of a continuous monitoring the parameter characterizing a state of a local tissue site (microcirculation and metabolism rate) and a real-time recording the reaction of the controlled parameter is performed. Efficacy of a therapeutic effect is determined by typical characteristics of a time course of a recorded parameter (reaction or response to the effect). The described method is applicable for visualizing practically all kinds of therapeutic effects including the both drug effects and such effects as physiotherapeutic effects, the effect of acupuncture methods, homeopathy and others. The method is applicable for visualizing the both systemic effect on a whole body and local effects on different regions of the body tissues.

In particular, the instant method allows for visualizing the effects of the traditional physiotherapy which now includes such methods of physiotherapeutic effect as a local decompression, a constant magnetic field, electric current, ultrasound, electromagnetic radiation of optic and infrared range and others.

The described method provides for the possibility of not only visualizing a therapeutic effect but also optimizing regimens and doses of therapeutic effect in order to optimize a therapeutic effect in the real-time feedback regimen.

Examples of Practical Use

The appearance of the experimental instrument, the operation principle of which is described above, is shown in FIG. 15. The block diagram of multi-sensor device is shown in FIG. 14. The developed technology allows for diminishing electronic components of the instrument down to the dimensions of one integral micro scheme and by this, to diminish dimensions of the instrument supposed for a practical use down to the dimensions not exceeding a wristwatch dimension. Proposed design of commercial device shown in FIG. 14.

Examples of Practical Use. Laboratory Tests Results

In order to confirm the concept of the method, more than 150 test experiments, with an average duration of 40 minutes each, and with 3 invasive average measurements in one test were performed in February-July 2015.

Measurements were carried out with the aid of an experimental instrument in the continuous monitoring mode (one measurement per second) with a duration of experiments of 30 to 150 minutes.

Calibration of the test device was carried out individually for each patient according to 2 measurements made on blood samples from fingers. The number of control measures for blood samples from the fingers during each experiment was from 2 to 9 measurements. Control measurements for blood samples from the finger were carried out using the Accu-Chek Active meter (Roche Diagnostics GmbH, Roche Group). In total, more than 150 experiments were conducted with a total of more than 600 control measurements. Results of the comparative experiments are presented in FIGS. 16, 17 (a, b, c, d) ("Results of the study in a practically healthy patient") and FIGS. 18 (a, b) ("Results of the study in patients with diabetes").

Examples of Practical Use

Results of Studies on Practically Healthy Patients

FIG. 16 shows the temporal dynamics of the blood sugar level of a practically healthy patient (55 years old, male) is presented during the sugar loading (sugar curve), recorded by a two-channel non-invasive microcalorimeter. Y axis contains values of the microcalorimeter signal in of mmol/liter units; X axis is the time in minutes. Sugar test (200 ml of 5% glucose solution) is taken by the patient on the 16th minute of the experiment. Results of invasive measurements, performed with the certified industrial meter "Accuchec active" from Roche-Diagnostics, are shown on the graph in circles. Absolute values of invasive measurements in units of mmol/liter are 5.4 (15 minutes), respectively; 6.4 (30 minutes); 7.3 (46 minutes); 6.6 (60 minutes); 5.4 (80 minutes) and 5.1 (100 minutes). The air temperature in the room is 22.C.

FIG. 17 a) shows the temporal dynamics of blood sugar in the morning on an empty stomach, recorded during the monitoring of blood sugar of a healthy patient (58 years old, male) during the day. X-axis represents the time in seconds, the Y-axis shows the meter reading in mmol/liter.

Calibration pulses (at times 200, 500, 1000, 2000) are imposed on the time dynamics of the instrument readings. Results of invasive measurements in mmol/liter are shown in green circles: 52 (350); 53 (1200); 54 (2100). Time in seconds (from the start of recording) is indicated in parentheses.

Values of air parameters inside the room (humidity H, temperature T, atmospheric pressure P) at the time of the first invasive measurement: HTP=25.6/21.5/1007.7. Climatic parameters: −1, 85%, 754, 3.0 m/s, at the beginning of the experiment; −1, 88%, 757, 2.0 m/s, at the end of the experiment.

FIG. 17 b) presents the temporal dynamics of blood sugar is presented 1 hour after breakfast, recorded during the monitoring of blood sugar of a healthy patient (58 years old, male) during the day. Temporal dynamics of blood sugar after 1 hour after breakfast. X-axis represents the time in seconds, the Y-axis shows the meter reading in mmol/liter.

Calibration pulses (at times 200, 500, 1000, 2000) are imposed on the time dynamics of the instrument readings. The results of invasive measurements in mmol/liter are shown by circles: 7.7 (350); 7.0 (1200); 6.7 (2100). Time in seconds (from the start of recording) is indicated in parentheses.

Values of air parameters inside the room (humidity H, temperature T, atmospheric pressure P) at the time of the first invasive measurement:
HTP=23.8/22.2/1009.1
Climatic parameters:
−2.85%, 756, 6.0 m/s, at the beginning of experiment.
−3.84%, 756, 5.0 m/s, at the end of the experiment Temporal dynamics of blood sugar after 1 hour after lunch, recorded during monitoring of blood sugar of a healthy patient (58 years old, male) during the day is presented in FIG. 17 c).

X-axis represents the time in seconds, the Y-axis shows the meter reading in mmol/liter. Calibration pulses (at times 200, 500, 1000, 2000) are imposed on the time dynamics of the instrument readings. The results of invasive measurements in mmol/liter are shown by circles: 7.7 (300); 8.9 (1200); 9.0 (2100). Time in seconds (from the start of recording) is indicated in parentheses.

Values of air parameters inside the room (humidity H, temperature T, atmospheric pressure P) at the time of the first invasive measurement:
HTP=23.8/22.3/1010.2
Climatic parameters:
−3/84/757/3.0 m/s, at the beginning of experiment
−3/78/757/3.0 m/s, at the end of experiment Temporary dynamics of blood sugar in 2.5 hours after afternoon, recorded in course of monitoring of blood sugar of a healthy patient (58 years old, male) during the day is shown in FIG. 17 d).

X-axis represents the time in seconds, the Y-axis shows the meter reading in mmol/liter. Calibration pulses (at times 200, 500, 1000, 2000) are imposed on the time dynamics of the instrument readings. The results of invasive measurements in mmol/liter are shown by circles: 6.2 (350); 6.4 (1200); 6.1 (2100). Time in seconds (from the start of recording) is indicated in parentheses.

Values of air parameters inside the room (humidity H, temperature T, atmospheric pressure P) at the time of the first invasive measurement:
CHTP=23.0/21.7/1011.6
Climatic parameters:
−3/78/757/4.0 m/s, at the beginning of experiment
−3/78/757/4.0 m/s, at the end of experiment

Examples of Practical Use. Results of Studies on Patients with Diabetes

The studies were performed in a clinic on 4 patients with type 2 diabetes (male and female) aged 40-89 years.

Measurements were carried out with the aid of experimental instrument in the mode of continuous monitoring with a duration of experiments from 30 to 60 minutes. Number of control measurements for blood samples taken from hands fingers during each experiment included from 2 to 3 measurements.

Control measurements on blood samples from the fingers were performed using the Accu-Chek Active meter (Roche Diagnostics GmbH, Roche Group). Specific results of these experiments are shown in FIG. 12 (a, b).

Temporal dynamics of blood sugar in patient D with type 2 diabetes (68 years old, male) before dinner is shown on the FIG. 18 (a).

X-axis represents the time in seconds, the Y-axis shows the meter reading in mmol/liter. Calibration pulses (at times 400, 1000, 1800) were superimposed on the temporal dynamics of the device readings. The results of invasive measurements in mmol/liter are shown by circles: 6.3 (450); 6.5 (1250). Time in seconds (from the start of recording) is indicated in parentheses.

Values of air parameters inside the room (humidity H, temperature T, atmospheric pressure P) at the time of the first invasive measurement:
CHTP=30.3/26.3/720.0

Figure 18B:
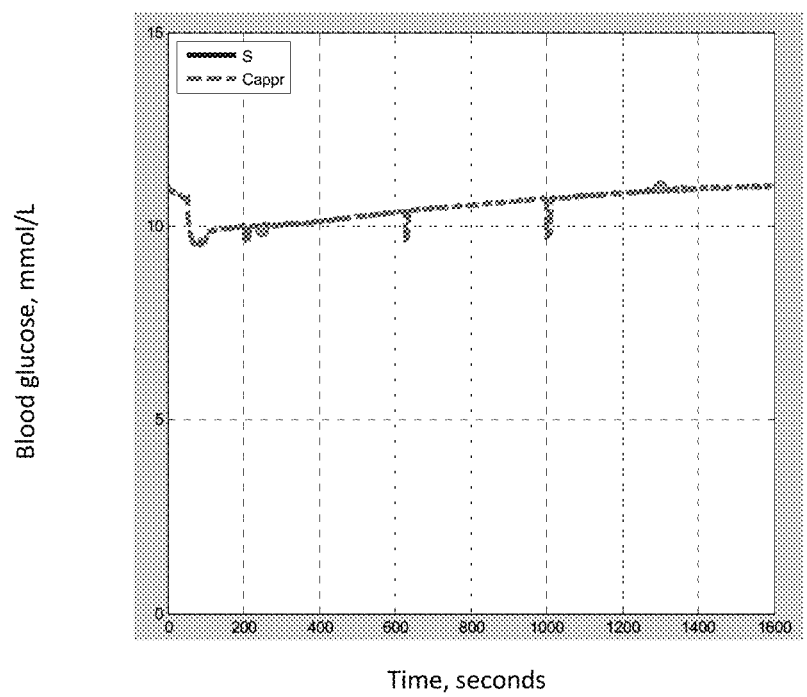

Temporal dynamics of blood sugar of patient D with type 2 diabetes (68 years old, male) 1 hour after lunch is shown in FIG. 18b).

X-axis represents the time in seconds, the Y-axis shows the meter reading in mmol/liter. Calibration pulses (at times 200, 650, 1000) were superimposed on the temporal dynamics of the device readings. The results of invasive measurements in mmol/liter are shown by circles: 9.9 (250); 11.0 (1300). Time in seconds (from the start of recording) is indicated in parentheses.

Values of air parameters inside the room (humidity H, temperature T, atmospheric pressure P) at the time of the first invasive measurement:
CHTP=29.3/26.5/718.0

BIBLIOGRAPHY

1. Edsall J. T., Gutfreund H. Biothermodynamics. The Study of Biochemical Processes at Equilibrium. John Willey & Sons, 1983.
2. Kendysh I. N. Regulation of carbohydrate metabolism. Izdatelstvo "Meditsina", Moskva, 1985 (In Russian).
3. Leonardo P. Concepts in Bioenergetics. Peusner Biomedical Associates, Prentice—Hall, Inc., Englewood Cliffs, N.J., 1974.
4. Lehninger A. L. Biochemistry. The John Hopkins University, School of Medicine. Worth Publishers, Inc., New York, 1972.
5. Atkins P. W. The second law. Scientific American Library, New York, 1984.
6. Musin R. F. Patent RF No 2087128. (In Russian).
7. Musin R. F., Morozov V. A, Godik E. E, Gulyaev Y. V. Electric properties of man's epidermis horny layer and water transport in it. Biophysics, 31(3): 478-481, 1986.
8. Forbath N., Hetenui C. Glucose dynamics in normal subjects and diabetic patients before and after a glucose load.—Diabetes, 1966, vol. 15, #11, p. 778-789.
9. Hall S. E. H., Saunders J., Sonksen P. H. Glucose and free acid turnover in normal subjects and diabetic patients before and after insulin treatment.—Diabetology, 1979, vol. 16, #5, p. 297-306.
10. Musin R. F., Godik E. E., Gulyaev Y. V., Morozov V. A. Natural water diffusion through the stratum corneum of the human body epidermis and its electrical properties/—3 International conference on water and ions in biological systems. Bucharest, Romania, 1984, p. 34.

11. Musin R. F., Ivanova N. Yu., Martynov V. A., Morozov V. A., Godik E. E., Gulyaev Y. V.: On the sensitivity of human skin to infrared heat fluxes. Reports of the USSR Academy of Sciences 289 (3): 718-720, 1986.
12. Gulyaev Y. V., Godik E. E., Musin R. F., Morozov V. A., Martynov V. A., Valiev I. V. (1989). The thermal threshold of skin sensitivity to electromagnetic radiation. Sensor systems, tom 3, No 2, p. 209-212. (In Russian).
13. Godik E. E., Morozov V. A., Musin R. F. (1985). On the dynamics of relaxation of triboelectric charge on the surface of the stratum corneum of the skin epidermis.—Biophysics, 30 (2): 309-312 (In Russian).
14. Musin R. F., Godik E. E., Gulyaev Yu. V., Morozov V. A., Sudarev A. M. Membrane mechanisms of water transport in epidermis. 4th International conference on water and ions in biological systems. Bucharest, Romania, 1988, pp. 167-172.
15. Musin R. F., Morozov V. A., Sudarev A. M. (1990). On the mechanism of water transport in the epidermis.—Biophysics, 35(4):653-656 (In Russian).
16. Yas Kuno. (1959). Human Perspiration. Charles & Thomas Publ., Springfield, Ill., USA.
17. A. V. Korobkov, S. A. Chesnokova. (1986). Atlas of normal physiology. M.: Bbscmauaa IKona, 1986.—351 p. (In Russian).
18. Gomeostaz. Pod red. P. D. Gorizontova.—M., "Meditsina", 1976, 464 s. (In Russian).
19. U.S. Pat. No. 5,795,305, Aug. 18, 1998, Cho et al. Process and device for non-invasive determination of glucose concentration in parts of human body.
20. U.S. Pat. No. 5,823,966, October 1998, Buchet. Non-invasive continuous blood glucose monitoring.
21. U.S. Pat. No. 5,890,489, Apr. 6, 1999, Elden. Method for non-invasive determination of glucose in body fluids.
22. U.S. Pat. No. 5,924,996, Jul. 20, 1999, Cho eta l. Process and device for detecting the exchange of heat between the human body and the invented device and its correlation to the glucose concentration in human body.
23. U.S. Pat. No. 6,522,903, Feb. 18, 2003, Berman et al. Glucose measurement assessment utilizing non-invasive assessment methods.
24. U.S. Pat. No. 6,517,482, Feb. 11, 2003, Elden et al. Method and apparatus for non-invasive determination of glucose in body fluids.
25. U.S. Pat. No. 5,040,541, Aug. 20, 1991, Poppendiek. Whole body calorimeter.
26. U.S. Pat. No. 4,386,604, Jun. 7, 1993, Herchey. Determination of the basal metabolic rate of humans with a whole-body calorimeter.
27. RU#2,396,897, Apr. 20, 2009, Musin R. F. A method and a device for microcalorimetric measurement of local tissue metabolism rate, intercellular substance water content, blood concentration of biochemical ingredients and pressure in the cardiovascular system.
28. John L. Smith. The Pursuit of Noninvasive Glucose: "Hunting the Deceitful Turkey". Fourth Edition, 2015.
29. E. Calvet, H. Prat, Microcalorimetrie. Applications physico-chimiques et biologiques. Masson, 1956.

The invention claimed is:
1. A method for monitoring blood glucose levels, the method comprising:
applying at least one heat and waterproof applicator to a skin surface with a dosed pressure, forming a closed system in a local area of living tissue under the applicator;
exerting an external physical effect on the local area of the tissue under the applicator, including the dosed pressure;
measuring temporal dynamics of physiological parameters in the local area of the living tissue under the applicator, including at least the temporal dynamics of:
osmotic pressure of an intercellular substance and/or an amount of water in an intercellular space of the tissue under the applicator;
temperature of a dermis under the applicator via radio thermometry or heat flow through a skin area under the applicator via a heat detector; and
elastic pressure of the tissue under the applicator,
measuring values of environmental climatic parameters before beginning the measurement of the temporal dynamics of the physiological parameters, including at least:
room temperature and relative humidity in a measurement room; and
atmosphere pressure,
measuring an external environment temperature or external heat flow through an enclosing structure between the measurement room and an external environment;
calculating a value of enthalpy, H, in a layer of the tissue under the applicator accounting for an influence of the climatic parameters, according to the formula:

$$H = H_0(T_{skin}, P_{sensor}) \times \theta(T_{room}, T_{ext}, RH_{room}, P_{atm}),$$
where $T_{skin}$ is the temperature of the dermis,
$P_{sensor}$ is the dosed pressure of the applicator on the skin surface,
$T_{room}$ is the room temperature,
$T_{ext}$ is an ambient air temperature behind the enclosing structure,
$RH_{room}$ is the relative humidity in the measurement room, and
$P_{atm}$ is the atmospheric pressure; and
calculating changes in blood glucose level based on a thermodynamics equation that connects the enthalpy with thermodynamic variables or variables of a thermodynamic state.

2. The method according to claim 1, wherein calibration parameters are determined in order to determine phenomenological constants used in the calculating of the changes in the blood glucose level.

3. The method according to claim 2, wherein the calibration parameters are determined individually for each patient by invasive blood glucose measurements.

4. The method according to claim 3, wherein the calibration parameters are determined by a calibration procedure comprising measuring a continuous glucose level in blood under conditions of a glucose tolerance test and determining tissue-to-insulin sensitivity.

5. The method according to claim 1, wherein the temperature of the dermis under the applicator is determined by measuring temporal dynamics of a skin surface temperature under the applicator.

6. The method according to claim 1, wherein the amount of water and its equilibrium content in the intercellular space of the tissue under the applicator includes temporal dynamics of the amount of water and its equilibrium content in the intercellular space of predetermined layers of the skin and subcutaneous tissues under the applicator, wherein the predetermined layers include the layer, and wherein the amount of water and its equilibrium content in the intercellular space of the predetermined layers of the skin and the subcutaneous tissues under the applicator is determined by measuring an amount of water in the stratum corneum under the applicator.

7. The method according to claim 6, wherein a change in the amount of water in the local area of the tissue under the applicator is determined by measuring electrical characteristics of the stratum corneum.

8. The method according to claim 6, wherein a change in the amount of water in the local area of the tissue under the applicator is determined by measuring spectral characteristics of the stratum corneum.

9. The method according to claim 6, wherein a change in the amount of water in the local area of the tissue under the applicator is determined by measuring thermophysical characteristics of the stratum corneum.

10. The method according to claim 6, further comprising making an additional measurement of a dependence of a change in the amount of the water in the intercellular space under the applicator on the external physical effect, and calculating a quantity of water that ensures swelling of the intercellular substance in a predetermined state.

11. The method according to claim 10, wherein the external physical effect further includes local decompression, heating, cooling, exposure to electric current, or magnetic field.

12. The method according to claim 11, wherein additional parameters are measured to determine a state of the intercellular substance, and wherein the additional parameters are selected from a group consisting of: blood pressure and acidity.

13. The method according to claim 1, wherein the local area of the living tissue is located on a hand.

14. The method according to claim 1, further comprising calculating a heat generation rate in metabolism of the local area of the living tissue.

15. The method according to claim 1, further comprising calculating an intensity of metabolism of the local area of the living tissue.

16. The method according to claim 15, wherein the calculation of the intensity of the metabolism of the local area of the living tissue is a calculation of basal metabolism intensity of the local area of the living tissue.

17. The method according to claim 16, further comprising measuring additional physiological and biochemical parameters to characterize the metabolism of the local area of living tissue.

18. The method according to claim 17, wherein at least one of the additional physiological and biochemical parameters is selected from a group consisting of: at least one biochemical parameter of blood, partial pressure of oxygen in the blood, partial pressure of carbon dioxide in the blood, heart rate, and blood pressure.

19. The method according to claim 18, wherein another of the additional physiological and biochemical parameters is selected from blood acidity, blood lactate concentration, and glucocorticoid hormone.

20. The method according to claim 19, wherein a concentration of the another of the additional physiological and biochemical parameters is calculated by measuring dynamics thereof in the stratum corneum.

21. The method according to claim 19, wherein a concentration of the another of the additional physiological and biochemical parameters is calculated by measuring dynamics thereof in a sweat solution of a sweat gland under the applicator.

22. The method according to claim 17, wherein another of the additional physiological and biochemical parameters is an electrophysiological parameter.

23. The method according to claim 1, wherein the layer of the tissue under the applicator for which the value of enthalpy is calculated is a deep layer of the skin.

24. The method according to claim 1, wherein the thermodynamics equation that connects the enthalpy with the thermodynamic variables or the variables of the thermodynamic state is $\Delta H = \Delta Q_{MET} + \Delta Q_{\Delta T} + K_M \times \Delta M + K_P \times \Delta P$, where:

$\Delta H$ is a change in the enthalpy resulting from tissue transition in the tissue under the applicator into a local thermodynamic equilibrium state;

$\Delta Q_{MET}$ is an amount of heat entering the tissue under the applicator during mass transfer;

$\Delta Q_{\Delta T}$ is an amount of heat entering the tissue under the applicator during heat transition caused by a temperature gradient between the skin surface and a depth;

$K_M$ and $K_P$ are constants;

$\Delta M$ is a change in the amount of water in the tissue under the applicator during mass transfer caused by a chemical potential gradient between the skin surface and the depth; and $\Delta P$ is a change in the elastic pressure of the tissue under the applicator during the mass transfer.

25. The method according to claim 1, wherein the amount of water and its equilibrium content in the intercellular space of predetermined layers of the skin and subcutaneous tissues under the applicator are determined by temporal dynamics of the amount of water in the local area of the tissue under the applicator, wherein the predetermined layers include the layer.

26. A device for monitoring blood glucose levels, comprising:

a heat and waterproof applicator having upper and inner surfaces and adapted to be applied on skin with a dosed pressure so as to form a closed system in a local area of living tissue under the applicator, sensors configured to measure physiological parameters, sensors configured to measure climatic parameters, a device configured to calibrate on a tissue site under the applicator, an installation platform for fixing the climatic parameters sensors, fixed over the applicator, at least one of an amplifier and an analog-digital converter installed on the upper surface of the applicator, and a processor, wherein the sensors configured to measure the climatic parameters are located on the installation platform, and the sensors configured to measure the physiological parameters are placed under the applicator, wherein the device is configured such that signals from the sensors configured to measure the physiological parameters and the sensors configured to measure the climatic parameters are sequentially applied to inputs of the at least one of the amplifier and the analog-digital converter;

wherein the processor is configured to perform operations comprising:

measuring temporal dynamics of the physiological parameters in the local area of the living tissue under the applicator, including at least the temporal dynamics of:

osmotic pressure of an intercellular substance and/or an amount of water in an intercellular space of the tissue under the applicator;

temperature of a dermis under the applicator via radio thermometry or heat flow through a skin area under the applicator via a heat detector; and elastic pressure of the tissue under the applicator, measuring values of environmental climatic parameters before beginning the measurement of the temporal dynamics of the physiological parameters, including at least:

room temperature and relative humidity in a measurement room; and atmosphere pressure, measuring an external environment temperature or external heat flow through an enclosing structure between the measurement room and an external environment;

calculating a value of enthalpy, H, in a layer of the tissue under the applicator accounting for an influence of the climatic parameters, according to the formula:

$$H=H_0(T_{skin}, P_{sensor})×θ(T_{room}, T_{ext}, RH_{room}, P_{atm}),$$

where $T_{skin}$ is the temperature of the dermis, $P_{sensor}$ is the dosed pressure of the applicator on a skin surface, $T_{room}$ is the room temperature, $T_{ext}$ is an ambient air temperature behind the enclosing structure, $RH_{room}$ is the relative humidity in the measurement room, and $P_{atm}$ is the atmospheric pressure; and calculating changes in blood glucose level based on a thermodynamics equation that connects the enthalpy with thermodynamic variables or variables of a thermodynamic state.

27. The device according to claim 26, further comprising a resistor or Peltier element configured to provide thermal power, an electric current, voltage, or electromagnetic radiation source; and a device configured to create the dosed pressure for the applicator.

28. The device according to claim 26, further comprising at least one sensor configured to measure the amount of water in the intercellular space of the tissue under the applicator by measuring water content in the stratum corneum.

29. The device according to claim 28, wherein the at least one sensor configured to measure the amount of water in the intercellular space of the tissue under the applicator is configured to measure electrical characteristics of the stratum corneum.

30. The device according to claim 29, wherein the at least one sensor configured to measure the electrical characteristics of the stratum corneum comprises at least one base electrode and at least one measuring electrode, a device for creating the dosed pressure, a power supply, and a measuring unit, wherein at least one of the base and measuring electrodes is made in a form of a dry waterproof design.

31. The device according to claim 30, wherein an area of the at least one base electrode is larger than an area of the at least one measuring electrode.

32. The device according to claim 31, wherein the area of the at least one measuring electrode satisfies the following condition: S (mm$^2$)>2P (mm)* 0.4 (mm).

33. The device according to claim 31, wherein a working surface of the at least one base electrode is provided with means for increasing conductivity of the skin at a point of contact therewith.

34. The device according to claim 33, wherein the means for increasing conductivity of the skin includes electrically conductive paste.

35. The device according to claim 30, wherein the at least one base electrode and the at least one measuring electrode are aligned disks with a total area defined by a diameter larger than a predetermined size.

36. The device according to claim 35, wherein the at least one base electrode and the at least one measuring electrode are formed as reciprocally coaxial discs.

37. The device according to claim 30, wherein the measuring unit is configured to measure transverse electroconductivity of the stratum corneum at a constant current or at a frequency current below a threshold.

38. The device according to claim 30, wherein the measuring unit is configured to measure the dielectric constant of the stratum corneum at frequencies below a threshold.

39. The device according to claim 28, wherein a the at least one sensor configured to measure the amount of water in the intercellular space of the tissue under the applicator is configured to measure spectral characteristics of the stratum corneum.

40. The device of claim 28, wherein the at least one sensor configured to measure the amount of water in the intercellular space of the tissue under the applicator is configured to measure thermophysical characteristics of the stratum corneum.

41. The device according to claim 28, wherein the at least one sensor configured to measure the amount of water in the intercellular space of the tissue under the applicator is configured to measure tissue pressure or the osmotic pressure of the intercellular substance.

42. The device according to claim 28, wherein the at least one sensor configured to measure the amount of water in the intercellular space of the tissue under the applicator is configured to measure hydraulic pressure in a microcirculation system.

43. The device according to claim 28, wherein the at least one sensor configured to measure the amount of water in the intercellular space of the tissue under the applicator is configured to measure the elastic pressure.

44. The device according to claim 28, wherein the sensors configured to measure physiological parameters comprises an additional sensor for measuring metabolism, wherein the additional sensor is selected from a group consisting of blood biochemical parameters sensors and sensors for parameters of an acid-base state.

45. The device according to claim 44, wherein the sensors for the parameters of the acid-base state include a blood lactate sensor.

46. The device according to claim 44, wherein the sensors for the parameters of the acid-base state include a blood acidity sensor.

47. The device according to claim 44, wherein the additional sensor is a blood cortisol sensor.

48. The device according to claim 44, wherein the additional sensor is a heart rate sensor.

49. The device according to claim 44, wherein the additional sensor is an electrophysiological parameter sensor.

50. The device according to claim 26, wherein at least an air temperature sensor, a relative air humidity sensor in the measurement room, and a heat flow sensor configured to measure the heat flow through the enclosing structure between the measurement room and the external environment are used as the sensors configured to measure climatic parameters.

51. The device according to claim 26, wherein the applicator is designed as a measuring capsule forming a closed cavity with diffusion and thermal contact with the skin surface.

52. The device according to claim 51, wherein the closed cavity of the measuring capsule is hermetically sealed, and a working surface of the cavity for contacting the skin is made of a rigid membrane that is permeable or semi-permeable for water and heat.

53. The device according to claim 51, wherein the closed cavity of the measuring capsule lacks a mechanical contact for contacting with the skin.

54. The device according to claim 51, wherein the closed cavity of the measuring capsule serves as a water quantity sensor.

55. The device according to claim 54, wherein the water quantity sensor is a water vapor pressure sensor.

56. The device according to claim 54, wherein the water quantity sensor is a water vapor concentration sensor.

57. The device according to claim 56, wherein the water vapor concentration sensor is based on spectroscopy.

58. The device according to claim 54, wherein the water quantity sensor is configured to sense thermophysical characteristics of water vapor.

59. The device according to claim 54, wherein the water quantity sensor is configured to sense heat capacity or thermal conductivity of water vapor.

60. The device according to claim 26, further comprising pneumatic, mechanical, piezoelectric, electromagnetic, vacuum, or hydraulic means for creating the dosed pressure.

* * * * *